(12) United States Patent
Luker et al.

(10) Patent No.: US 8,163,727 B2
(45) Date of Patent: Apr. 24, 2012

(54) BIPHENYLOXYACETIC ACID DERIVATIVES FOR THE TREATMENT OF RESPIRATORY DISEASE

(75) Inventors: Timothy Jon Luker, Loughborough (GB); Timothy Nicholas Birkinshaw, Loughborough (GB); Rukhsana Tasneem Mohammed, Loughborough (GB)

(73) Assignee: AstraZeneca AB, Södertälje (SE)

( * ) Notice: Subject to any disclaimer, the term of this patent is extended or adjusted under 35 U.S.C. 154(b) by 0 days.

(21) Appl. No.: 12/642,244

(22) Filed: Dec. 18, 2009

(65) Prior Publication Data
US 2010/0160285 A1 Jun. 24, 2010

Related U.S. Application Data

(62) Division of application No. 11/574,076, filed as application No. PCT/GB2005/003255 on Aug. 22, 2005, now Pat. No. 7,737,135.

(30) Foreign Application Priority Data

Aug. 24, 2004 (GB) ................................. 0418830.6

(51) Int. Cl.
| | |
|---|---|
| A61K 31/19 | (2006.01) |
| A61K 31/5375 | (2006.01) |
| A61K 31/40 | (2006.01) |
| A61K 31/397 | (2006.01) |
| A61K 31/445 | (2006.01) |
| C07C 53/08 | (2006.01) |
| C07C 317/02 | (2006.01) |
| C07D 265/28 | (2006.01) |
| C07D 207/00 | (2006.01) |
| C07D 205/04 | (2006.01) |
| C07D 211/00 | (2006.01) |

(52) U.S. Cl. ............... 514/210.17; 514/571; 514/239.5; 514/423; 514/330; 544/158; 548/539; 562/429

(58) Field of Classification Search .............. None
See application file for complete search history.

(56) References Cited

U.S. PATENT DOCUMENTS

| | | | |
|---|---|---|---|
| 3,278,524 A | 10/1966 | Johnson et al. |
| 3,920,846 A | 11/1975 | Hanauye et al. |
| 3,954,852 A | 5/1976 | Shen et al. |
| 3,985,779 A | 10/1976 | Tanaka et al. |
| 4,234,742 A | 11/1980 | Cognacq et al. |
| 4,248,618 A | 2/1981 | Serban et al. |
| 4,670,566 A | 6/1987 | Walsh et al. |
| 5,145,790 A | 9/1992 | Mattingly et al. |
| 5,411,972 A | 5/1995 | Komoto et al. |
| 5,413,891 A | 5/1995 | Matsuura et al. |
| 5,532,371 A | 7/1996 | Komoto et al. |
| 5,703,099 A | 12/1997 | Hamanaka et al. |
| 6,057,408 A | 5/2000 | Winter et al. |
| 6,150,413 A | 11/2000 | Bernardon et al. |
| 6,376,546 B1 | 4/2002 | Shoda et al. |
| 6,417,212 B1 | 7/2002 | Brooks et al. |
| 7,056,942 B2 | 6/2006 | Hildesheim et al. |
| 7,067,507 B2 | 6/2006 | Pulley et al. |
| 7,737,135 B2 | 6/2010 | Luker et al. |
| 8,003,703 B2 | 8/2011 | Bonnert et al. |
| 8,008,350 B2 | 8/2011 | Luker et al. |
| 8,022,248 B2 | 9/2011 | Bonnert et al. |
| 2004/0029933 A1 | 2/2004 | Zhao et al. |
| 2004/0097555 A1 | 5/2004 | Ohkawa et al. |
| 2004/0220237 A1 | 11/2004 | Fu et al. |
| 2005/0239881 A1 | 10/2005 | Dunn et al. |
| 2006/0211765 A1 | 9/2006 | Pairaudeau et al. |
| 2006/0264435 A1 | 11/2006 | Bonnert et al. |
| 2006/0293352 A1 | 12/2006 | Bonnert et al. |
| 2007/0249686 A1 | 10/2007 | Bonnert et al. |
| 2008/0114002 A1 | 5/2008 | Bonnert et al. |
| 2008/0132480 A1 | 6/2008 | Luker et al. |
| 2008/0255150 A1 | 10/2008 | Luker |
| 2008/0293775 A1 | 11/2008 | Bonnert et al. |
| 2009/0012151 A1 | 1/2009 | Bonnert et al. |
| 2009/0036535 A1 | 2/2009 | Luker et al. |
| 2009/0149448 A1 | 6/2009 | Alcaraz et al. |
| 2009/0192163 A1 | 7/2009 | Luker et al. |
| 2010/0160285 A1 | 6/2010 | Luker et al. |

(Continued)

FOREIGN PATENT DOCUMENTS

CH 432119 9/1967

(Continued)

OTHER PUBLICATIONS

Petrillo et al., Tetrahedron, (1990), vol. 46(23), p. 7977-7990.*
AstraZeneca AB: WO03066046 & WO03066047, "The use of indole-3-acetic acids as CRTH2 receptor antagonists", Expert Opin. Ther. Patents 14(1):125-128 (2004).
Berhenke et al., "Some Aryloxyaliphatic Acids", Journal of the American Chemical Society 73:4458 (1951).
Burger, "Isosterism and bioisosterism in drug design", in Progress in Drug Research 287-328 (Ernst Jucker, ed., Birkhauser Verlag, 1991).
Chemical abstract 123:213132 in CAS (or JP07140725), 1995.
Chemical abstract 123:22081 in CAS (or EP622690), 1994.

(Continued)

Primary Examiner — Yong Chu

(57) ABSTRACT

The invention relates to substituted phenoxyacetic acids of formula (I), where the variables are as defined in claim 1, as useful pharmaceutical compounds for treating respiratory disorders, pharmaceutical compositions containing them, and processes for their preparation.

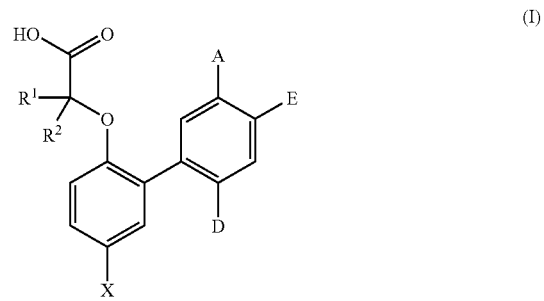

9 Claims, No Drawings

U.S. PATENT DOCUMENTS

2011/0152374 A1    6/2011    Luker et al.

FOREIGN PATENT DOCUMENTS

| | | |
|---|---|---|
| EP | 0006789 | 1/1980 |
| EP | 0114734 | 8/1984 |
| EP | 0455058 | 11/1991 |
| EP | 0540165 | 5/1993 |
| EP | 0622690 | 11/1994 |
| EP | 0622816 | 11/1994 |
| EP | 0839808 | 5/1998 |
| EP | 1012142 | 6/2000 |
| EP | 1170594 | 1/2002 |
| EP | 1211513 | 6/2002 |
| EP | 1471057 | 10/2004 |
| GB | 690816 | 4/1953 |
| GB | 1 356 834 | 6/1974 |
| GB | 1 464 977 | 2/1977 |
| GB | 1 469 687 | 4/1977 |
| GB | 2 031 408 | 4/1980 |
| GB | 2 041 363 | 9/1980 |
| GB | 1 585 963 | 3/1981 |
| JP | 07140725 | 6/1995 |
| JP | 2003-508389 | 3/2003 |
| JP | 2006-521382 | 9/2006 |
| JP | 2006-522117 | 9/2006 |
| WO | WO 93/12086 | 6/1993 |
| WO | WO 97/08126 | 3/1997 |
| WO | WO 98/03164 | 1/1998 |
| WO | WO 99/11605 | 3/1999 |
| WO | WO 99/11627 | 3/1999 |
| WO | WO 01/16120 | 3/2001 |
| WO | WO 01/60807 | 8/2001 |
| WO | WO 01/81312 | 11/2001 |
| WO | WO 01/92224 | 12/2001 |
| WO | WO 03/064387 | 8/2003 |
| WO | WO 03/066047 | 8/2003 |
| WO | WO 03/068744 | 8/2003 |
| WO | WO 03/097042 | 11/2003 |
| WO | WO 03/097598 | 11/2003 |
| WO | WO 03/101961 | 12/2003 |
| WO | WO 2004/007451 | 1/2004 |
| WO | WO 2004/048314 | 6/2004 |
| WO | WO 2004/058164 | 7/2004 |
| WO | WO 2004/089884 | 10/2004 |
| WO | WO 2004/089885 | 10/2004 |
| WO | WO 2004/094386 | 11/2004 |
| WO | WO 2004/096777 | 11/2004 |
| WO | WO 2005/018529 | 3/2005 |
| WO | WO 2005/044260 | 5/2005 |
| WO | WO 2005/105727 | 11/2005 |
| WO | WO 2005/115382 | 12/2005 |
| WO | WO 2006/005909 | 1/2006 |
| WO | WO 2006/021759 | 3/2006 |
| WO | WO 2006/037982 | 4/2006 |
| WO | WO 2006/056752 | 6/2006 |
| WO | WO 2006/125596 | 11/2006 |
| WO | WO 2007/039736 | 4/2007 |
| WO | WO 2007/039741 | 4/2007 |
| WO | WO 2007/052023 | 5/2007 |
| WO | WO 2007/068894 | 6/2007 |

OTHER PUBLICATIONS

Chemical abstract 116:123167 in CAS (or EP455058), 1993.
Chemical abstract 85:56485 in CAS or Parli et al., "The relation between the metabolism of 2,4-dichloro-6-phenylphenoxyethylamine (DPEA) and related compounds and their activities as microsomal mono-oxygenase inhibitors", Drug Metabolism and Disposition 1(4):628-33 (1973).
Chemical abstract 69:93942 in CAS or Cheng et al., "Phenylphenol derivatives with biological activity. III. Fungistatic activity of phenylphenol derivatives", Agricultural and Biological Chemistry 32(9):1162-74 (1968).
Chemical abstract 49:86470 in CAS or Mel'nikov et al., "Structure and physiological activity of alkyl- and aryl-phenoxyacetic acids and their derivatives", Fiziologiya Rastenii 2:267-70 (1955).
Chemical abstract 35:37645 in CAS or Hazlet et al., "The Bromination of 2-Phenylphenyl Acetate", Journal of the American Chemical Society 63:1890-2 (1941).
Chiu et al., "Derivation and Properties of Recombinant Fab Antibodies to Coplanar Polychlorinated Biphenyls", *J. Agric. Food Chem.* 48:2614-2624 (2000).
Coxworth, "Synthesis of Chlorinated 2-(3-Benzofuranyl)Phenols", *Canadian Journal of Chemistry* 44:1092-1096 (1966).
"DialogWeb Records", http://www.dialogweb.com/cgi/document?req=1284661379410, accessed Sep. 16, 2010.
Ebenezar et al., "Prostaglandins in the patent literature", *Expert Opin. Ther. Patents* 17(9):1131-1145 (2007).
Fromageot et al., "Photodecarboxylation of 2-(2'-carboxymethoxy-5'-methylphenyl)-benzotriazole", *Journal of Photochemistry and Photobiology, A: Chemistry* 44(1):93-98 (1988).
Hazlet et al., "The Bromination of 2-Phenylphenyl Acetate", *Journal of the American Chemical Society* 63:1890-1892 (1941).
Manske et al., "Synthesis and Reactions of Some Dibenzoxepins", *Journal of American Chemical Society* 72:4797-4799 (1950).
Ono Pharm. Co. Ltd: WO03022813 & WO03022814, "The use of prostaglandin $D_2$ receptor antagonists to treat allergic rhinitis", *Expert Opin. Ther. Patents* 13(10):1657-1661 (2003).
Patani et al., "Bioisosterism: A Rational Approach in Drug Design", *Chem. Rev.* 96:3147-3176 (1996).
Ram et al., "Potential Hypolipidemic Agents Part VI: Synthesis and Biological Activity of Some New 4-Chloro/Methyl-2-pyrazolylphenoxy Alkanoates", *Indian Drugs* 29(6), 258-262 (1992).
Ueda et al., "The Synthesis of 10-(4-Methylpiperazino)dibenzo[$b,f$] thiepin and Related Compounds. Neurotropic and Psychotropic Agents", *Chem. Pharm. Bull.* 23(10):2223-2231 (1975).
Wermuth, "Molecular Variations Based on Isosteric Replacements", The Practice of Medicinal Chemistry, 1996, chapter 13, pp. 203-237.
Preventing Asthma Symptoms [online] [retrieved on Apr. 23, 2010 from the internet] URL:http://www.webmd.com/asthma/guide/asthma-prevention.
Allergic Rhinitis—Prevention [online] [retrieved on Apr. 23, 2010 from the internet] URL:http://www.webmd.com/allergies/tc/allergic-rhinitis-prevention.
COPD Treatments: Improving Your Quality of Life [online] [retrieved on Apr. 23, 2010 from the internet] URL:http://www.webmd.com/lung/copd/copd-treatments-improving-your-quality-of-life.
Database Beilstein chemical extract accession No. 6722243, Jan. 2010.
Database Beilstein chemical extract accession No. 6722682, Jan. 2010.
Database Beilstein chemical extract accession No. 3532059, Jan. 2010.
Database Beilstein chemical extract accession No. 2533336, Jan. 2010.
Database Beilstein chemical extract accession No. 2537173, Jan. 2010.
Database Beilstein chemical extract accession No. 3385275, Jan. 2010.
Database Beilstein chemical extract accession No. 3386554, Jan. 2010.
USPTO Office Action in U.S. Appl. No. 10/552,082, mailed Jan. 7, 2010, 12 pages.
Fish & Richardson P.C., Amendment in Reply to Action of Jan. 7, 2010 in U.S. Appl. No. 10/552,082, filed Jul. 2, 2010, 8 pages.
USPTO Notice of Allowance in U.S. Appl. No. 10/552,082, mailed Sep. 15, 2010, 12 pages.
Fish & Richardson P.C., Amendment in Reply to Action of Dec. 7, 2009 in U.S. Appl. No. 10/551,783, filed Mar. 8, 2010, 17 pages.
USPTO Office Action in U.S. Appl. No. 10/551,783, mailed Apr. 23, 2010, 9 pages.
Fish & Richardson P.C., Amendment in Reply to Action of Apr. 23, 2010 in U.S. Appl. No. 10/551,783, filed Jul. 2, 2010, 23 pages.
USPTO Notice of Allowance in U.S. Appl. No. 10/551,783, mailed Sep. 7, 2010, 6 pages.

Fish & Richardson P.C., RCE and IDS in reply to Notice of Allowance of Sep. 7, 2010 in U.S. Appl. No. 10/551,783, filed Dec. 6, 2010, 4 pages.
USPTO Notice of Allowance in U.S. Appl. No. 10/569,065, mailed Jan. 28, 2010, 9 pages.
Fish & Richardson P.C., RCE and IDS in Reply to Notice of Allowance of Jan. 28, 2010 in U.S. Appl. No. 10/569,065, filed Mar. 31, 2010, 5 pages.
USPTO Notice of Allowance in U.S. Appl. No. 10/569,065, mailed May 13, 2010, 10 pages.
Fish & Richardson P.C., RCE and IDS in Reply to Notice of Allowance of May 13, 2010 in U.S. Appl. No. 10/569,065, filed Aug. 2, 2010, 4 pages.
USPTO Notice of Allowance in U.S. Appl. No. 10/569,065, mailed Sep. 1, 2010, 9 pages.
Fish & Richardson P.C., RCE and IDS in Reply to Notice of Allowance of Sep. 1, 2010 in U.S. Appl. No. 10/569,065, filed Nov. 8, 2010, 5 pages.
USPTO Notice of Allowance in U.S. Appl. No. 10/569,065, mailed Dec. 2, 2010, 10 pages.
Fish & Richardson P.C., RCE and IDS in Reply to Notice of Allowance of Dec. 2, 2010 in U.S. Appl. No. 10/569,065, filed Feb. 15, 2011, 5 pages.
USPTO Notice of Allowance in U.S. Appl. No. 10/569,065, mailed Apr. 8, 2011, 10 pages.
USPTO Office Action in U.S. Appl. No. 11/571,707, mailed Mar. 12, 2010, 16 pages.
Fish & Richardson P.C., Amendment in Reply to Action of Mar. 12, 2010 in U.S. Appl. No. 11/571,707, filed Sep. 3, 2010, 14 pages.
USPTO Notice of Allowance in U.S. Appl. No. 11/571,707, mailed Nov. 22, 2010, 12 pages.
Fish & Richardson P.C., Response to Notice of Allowance of Nov. 22, 2010 in U.S. Appl. No. 11/571,707, filed Feb. 18, 2011, 12 pages.
Fish & Richardson P.C., RCE, Petition to Withdraw from Issue, and IDS in U.S. Appl. No. 11/571,707, filed Apr. 13, 2011, 7 pages.
USPTO Decision Granting Petition under 37 CFR 1.313(c)(2) in U.S. Appl. No. 11/571,707, mailed Apr. 14, 2011, 1 page.
USPTO Notice of Allowance in U.S. Appl. No. 11/571,707, mailed May 6, 2011, 11 pages.
USPTO Office Action in U.S. Appl. No. 11/574,076, mailed Oct. 27, 2008, 23 pages.
Fish & Richardson P.C., Amendment in Reply to Action of Oct. 27, 2008 in U.S. Appl. No. 11/574,076, filed Apr. 27, 2009, 21 pages.
USPTO Final Office Action in U.S. Appl. No. 11/574,076, mailed Aug. 18, 2009, 7 pages.
Fish & Richardson P.C., RCE and Amendment in Reply to Action of Aug. 18, 2009 in U.S. Appl. No. 11/574,076, filed Dec. 18, 2009, 13 pages.
USPTO Notice of Allowance in U.S. Appl. No. 11/574,076, mailed Feb. 3, 2010, 12 pages.
Fish & Richardson P.C., Response to Notice of Allowance of Feb. 3, 2010 in U.S. Appl. No. 11/574,076, filed Apr. 30, 2010, 2 pages.
Fish & Richardson P.C., Amendment in Reply to Action of Jul. 22, 2009 in U.S. Appl. No. 11/576,372, filed Jan. 22, 2010, 18 pages.
USPTO Final Office Action in U.S. Appl. No. 11/576,372, mailed May 7, 2010, 7 pages.
Fish & Richardson P.C., Reply to Action of May 7, 2010 in U.S. Appl. No. 11/576,372, filed Aug. 9, 2010, 10 pages.
USPTO Office Action in U.S. Appl. No. 11/576,372, mailed Sep. 2, 2010, 7 pages.
Fish & Richardson P.C., RCE, IDS and Amendment in Reply to Action of Sep. 2, 2010 in U.S. Appl. No. 11/576,372, filed Dec. 2, 2010, 16 pages.
USPTO Office Action in U.S. Appl. No. 11/719,832, mailed Apr. 30, 2010, 20 pages.
Fish & Richardson P.C., Amendment in Reply to Action of Apr. 30, 2010 in U.S. Appl. No. 11/719,832, filed Aug. 30, 2010, 18 pages.
USPTO Office Action in U.S. Appl. No. 11/719,832, mailed Oct. 6, 2010, 12 pages.
Fish & Richardson P.C., RCE, IDS and Amendment in Reply to Action of Oct. 6, 2010 in U.S. Appl. No. 11/719,832, filed Apr. 6, 2011, 27 pages.

USPTO Office Action in U.S. Appl. No. 12/089,275, mailed Jan. 26, 2011, 25 pages.
USPTO Notice of Allowance in U.S. Appl. No. 12/089,276, mailed Jan. 4, 2010, 6 pages.
Fish & Richardson P.C., RCE and IDS in Reply to Notice of Allowance of Jan. 4, 2010 in U.S. Appl. No. 12/089,276, filed Mar. 31, 2010, 7 pages.
USPTO Notice of Allowance in U.S. Appl. No. 12/089,276, mailed Apr. 21, 2010, 11 pages.
Fish & Richardson P.C., RCE and IDS in Reply to Notice of Allowance of Apr. 21, 2010 in U.S. Appl. No. 12/089,276, filed Jul. 21, 2010, 5 pages.
USPTO Notice of Allowance in U.S. Appl. No. 12/089,276, mailed Sep. 21, 2010, 9 pages.
Fish & Richardson P.C., RCE and IDS in Reply to Notice of Allowance of Sep. 21, 2010 in U.S. Appl. No. 12/089,276, filed Dec. 20, 2010, 6 pages.
USPTO Notice of Allowance in U.S. Appl. No. 12/089,276, mailed Jan. 4, 2011, 11 pages.
Fish & Richardson P.C., RCE and IDS in Reply to Notice of Allowance of Jan. 4, 2011 in U.S. Appl. No. 12/089,276, filed Apr. 4, 2011, 4 pages.
USPTO Notice of Allowance in U.S. Appl. No. 12/089,276, mailed Apr. 12, 2011, 9 pages.
Fish & Richardson P.C., Amendment in Reply to Action of Aug. 4, 2009 in U.S. Appl. No. 12/092,431, filed Feb. 3, 2010, 15 pages.
USPTO Final Office Action in U.S. Appl. No. 12/092,431, mailed May 4, 2010, 13 pages.
Fish & Richardson P.C., RCE, IDS and Amendment in Reply to Action of May 4, 2010 in U.S. Appl. No. 12/092,431, filed Sep. 7, 2010, 16 pages.
Fish & Richardson P.C., Amendment in Reply to Action of Nov. 2, 2009 in U.S. Appl. No. 12/167,513, filed Feb. 2, 2010, 19 pages.
USPTO Final Office Action in U.S. Appl. No. 12/167,513, mailed Apr. 22, 2010, 22 pages.
Fish & Richardson P.C., Amendment in Reply to Action of Apr. 22, 2010 in U.S. Appl. No. 12/167,513, filed Oct. 22, 2010, 22 pages.
Dalal et al., "Synthetic insecticides. I. Synthesis of α, α-bis(aryl)-β, β, γ-trichlorobutanes", STN Accession No. 1950:35789, Document No. 44:35789, Abstract of Journal of the Indian Chemical Society 26:549-52 (1949).
Gavezzotti, "Are Crystal Structures Predictable?", Acc. Chem. Res. 27:309-314 (1994).
Golub et al., "Molecular Classification of Cancer: Class Discovery and Class Prediction by Gene Expression Monitoring", Science 286:531-537 (1999).
Hazlet et al., "Bromination of 2-phenylphenyl acetate", STN Accession No. 1941:37645, Document No. 35:37645, Abstract of Journal of the American Chemical Society 63:1890-2 (1941).
Ly et al., "Small-molecule CRTH2 antagonists for the treatment of allergic inflammation: an overview", Expert Opin. Invest. Drugs 14(7):769-773 (2005).
Morissette et al., "High-throughput crystallization: polymorphs, salts, co-crystals and solvates of pharmaceutical solids", Advanced Drug Delivery Reviews 56:275-300 (2004).
Rhinitis [online] retrieved on Nov. 12, 2008. Retrieved from URL; http://www.healthline.com/galecontent/rhinitis?print=true.
RN 110624-55-0, retrieved from CAPLUS; retrieved on Apr. 7, 2008.
Ulven et al., "Targeting of the Prostaglandin $D_2$ Receptors DP and CRTH2 for Treatment of Inflammation", Current Topics in Medicinal Chemistry 6:1427-1444 (2006).
USPTO Office Action in U.S. Appl. No. 10/552,082, mailed Oct. 29, 2007, 6 pages.
Fish & Richardson P.C., Amendment in Reply to Action of Oct. 29, 2007 in U.S. Appl. No. 10/552,082, filed Feb. 29, 2008, 18 pages.
USPTO Final Office Action in U.S. Appl. No. 10/552,082, mailed Jun. 9, 2008, 18 pages.
Fish & Richardson P.C., Amendment in Reply to Action of Jun. 9, 2008 in U.S. Appl. No. 10/552,082, filed Sep. 9, 2008, 11 pages.
USPTO Office Action in U.S. Appl. No. 10/552,082, mailed Dec. 4, 2008, 23 pages.
Fish & Richardson P.C., Amendment in Reply to Action of Dec. 4, 2008 in U.S. Appl. No. 10/552,082, filed Apr. 6, 2009, 8 pages.

USPTO Notice of Allowance in U.S. Appl. No. 10/552,082, mailed Jul. 1, 2009, 9 pages.
Fish & Richardson P.C., RCE and Interview Summary in response to Notice of Allowance of Jul. 1, 2009 in U.S. Appl. No. 10/552,082, filed Sep. 30, 2009, 2 pages.
USPTO Office Action in U.S. Appl. No. 10/551,783, mailed Dec. 7, 2009, 15 pages.
USPTO Office Action in U.S. Appl. No. 10/569,065, mailed May 4, 2007, 12 pages.
Fish & Richardson P.C., Amendment in Reply to Action of May 4, 2007 in U.S. Appl. No. 10/569,065, filed Aug. 3, 2007, 14 pages.
USPTO Final Office Action in U.S. Appl. No. 10/569,065, mailed Oct. 17, 2007, 4 pages.
Fish & Richardson P.C., Amendment in Reply to Action of Oct. 17, 2007 in U.S. Appl. No. 10/569,065, filed Jan. 17, 2008, 9 pages.
USPTO Office Action in U.S. Appl. No. 10/569,065, mailed Apr. 16, 2008, 14 pages.
Fish & Richardson P.C., Amendment in Reply to Action of Apr. 16, 2008 in U.S. Appl. No. 10/569,065, filed Jul. 16, 2008, 38 pages.
USPTO Office Action in U.S. Appl. No. 10/569,065, mailed Oct. 28, 2008, 15 pages.
Fish & Richardson P.C., Amendment in Reply to Action of Oct. 28, 2008 in U.S. Appl. No. 10/569,065, filed Jan. 27, 2009, 7 pages.
USPTO Office Action in U.S. Appl. No, 10/569,065, mailed May 13, 2009, 10 pages.
Fish & Richardson P.C., Amendment in Reply to Action of May 13, 2009 in U.S. Appl. No. 10/569,065, filed Jul. 14, 2009, 9 pages.
USPTO Notice of Allowance in U.S. Appl. No. 10/569,065, mailed Oct. 23, 2009, 10 pages.
Fish & Richardson P.C., RCE and IDS in Reply to Notice of Allowance of Oct. 23, 2009 U.S. Appl. No. 10/569,065, filed Nov. 5, 2009, 3 pages.
USPTO Office Action in U.S. Appl. No. 11/576,372, mailed Jul. 22, 2009, 19 pages.
USPTO Office Action in U.S. Appl. No. 12/089,276, mailed Jun. 17, 2009, 28 pages.
Fish & Richardson P.C., Amendment in Reply to Action of Jun. 17, 2009 in U.S. Appl. No. 12/089,276, filed Sep. 22, 2009, 10 pages.
USPTO Office Action in U.S. Appl. No. 12/092,431, mailed Aug. 4, 2009, 8 pages.
USPTO Office Action in U.S. Appl. No. 12/167,513, mailed Nov. 2, 2009, 19 pages.
Amin et al., "The Fries Reaction: Part VI—the rearrangement of aryl p-toluene-sulphonates & a convenient method for synthesis of hydroxy-diarylsulphones", *Journal of Scientific Industrial Research*, vol. 13B, 1954, pp. 181-183.
Atkinson et al., "Substituted (2-Phenoxyphenyl)acetic Acids with Antiinflammatory Activity", *J. Med. Chem.*, vol. 26, 1983, pp. 1353-1360.
Baliah et al., "Fries rearrangement of the benzenesulphonates of xylenols", *Recueil des Travaux Chimiques des Pays-Bas*, vol. 80, 1961, pp. 139-148.
Bartl et al., "Thioxanthene Derivatives of Pharmacological Interest: 1,2,4-Trichloro and 2,4,5,6-Tetrachloro Derivatives of 9-(3-Dimethylaminopropylidene)Thioxanthene", *Collection Czechoslov. Chem. Commun.*, vol. 49, 1984, pp. 2295-2308.
Brown et al., "Some Chlorinated Hydroxyphenoxyacetic Acids", *Journal of the Chemical Society*, 1955, pp. 3681-3687.
Budavari, S., "The merck Index, 13$^{th}$ edition", p. 3106, monograph 3108, XP-002347170, 2001.
Cavill et al., "The chemistry of plant-growth regulators. Part I. 2:4-dichloro-6-hydroxyphenoxyacetic acid and related compounds", *Journal of the Chemical Society*, 1954, pp. 565-569.
*Cecil Textbook of Medicine*, 20$^{th}$ ed. (1996), vol. 2, pp. 1992-1996.
*Cecil Textbook of Medicine*, 20$^{th}$ ed. (1996), vol. 2, pp. 2050-2057.
Clemo et al., "Strychnine and brucine. Part II", *Journal of the Chemical Society*, vol. 125, 1924, pp. 1751-1804, XP008053173.
Cocco et al., "Annulation of functionalized hexadienones as an efficient regioselective approach to N-Aryl-2-(trifluoromethyl)-4-pyridinamines", *Tetrahedron Letters*, vol. 40, No. 23, 1999, pp. 4407-4410.

FDA mulls drug to slow late-stage Alzheimer's [online], [retrieved Sep. 24, 2003]. Retrieved from the Internet, URL; http://www.cnn.com/2003/HEALTH/conditions/09/24/alzheimers.drug.ap/index.html>.
Gallo et al., "Spirodioxolanonarenones. II. Synthesis of a halogenated 1,4-dioxaspiro[4,5]deca-7,9-diene-2,6-dione", *Journal of Chemistry*, vol. 30, No. 5, 1965, pp. 1657-1658.
Gaunt et al., "Metabolism of 4-chloro-2-methylphenoxyacetate by a soil pseudomonad", *Biochem. J.*, vol. 122, 1971, pp. 519-526.
Hazeldine et al., "Design, Synthesis and Biological Evaluation of Analogues of the Antitumor Agent, 2-{4-[(7-Chloro-2-quinoxalinyl)oxy]phenoxy}propionic Acid (XK469)", *J. Med. Chem.*, vol. 44, 2001, pp. 1758-1776.
Huston et al., "Chloro derivatives of *o*- and *p*-benzyl phenols. II. Some monochloro, dichloro and trichloro derivatives of ortho and para benzyl phenols", *Journal of the American Chemical Society*, vol. 55, No. 11, 1933, pp. 4639-4643.
Inukai et al., "*ortho*-Disubstituted *F*-benzenes. III. Preparation of (*F*-benzo)heterocyclic compounds from *F*-benzoic acid and *F*-phenol, and the reactions of some intermediary *F*-benzoyl- and F-phenoxy compounds", *Bull. Chem. Soc. Jpn.*, vol. 54, No. 11, 1981, pp. 3447-3452.
Janczewski et al., "Effect of Molecular Structure on Optical Properties of Sulfoxide Systems. *o*-Phenoxyphenylsulfinylacetic Acid and some of Their Derivatives. Part II", *Polish Journal of Chemistry*, vol. 62, No. 1-3, 1964, pp. 91-105, XP008053171.
Kmonicek et al., "(Tert-Amino)-11-(4-Methylpiperazino)Dibenzo[*bf*]Thiepins and their 10,11-Dihydro Derivatives; Synthesis and Neuroleptic Activity", *Collection Czechoslov. Chem. Commun.*, vol. 52, 1987, pp. 792-803, XP-002347166.
Litvak et al., "Synthesis and $S_NAr$ reactions of new dioxins and predioxins", *Chemosphere*, vol. 43, No. 4-7, 2001, pp. 493-495.
Lupus erythematosus [online], [retrieved Dec. 28, 2006]. Retrieved from the Internet, URL; http://en.wikipedia.org/wiki/Lupus_erythematosus>.
Maeda et al., "Studies on the Synthesis and Analgesic and Anti-inflammatory Activities of 2-Thiazolylamino- and 2-Thiazolyloxy-arylacetic Acid Derivatives", *Chem. Pharm. Bull.*, vol. 31, No. 10, 1983, pp. 3424-3445, XP-002347167.
Manoury et al., "Synthesis and Analgesic Activities of Some (4-Substituted phenyl-1-piperazinyl)alkyl 2-Aminobenzoates and 2-Aminonicotinates", Journal of Medicinal Chemistry, vol. 22(5), pp. 554-559 (1979).
Meunier et al., "Photochemical behaviour of dichlorprop [(±)-2-(2,4-dichlorophenoxy)propanoic acid] in aqueoud solution", *Pest Management Science*, vol. 58, No. 8, 2002, pp. 845-852.
Moser et al., "Synthesis and Quantitative Structure—Activity Relationships of Diclofenac Analogues", *J. Med. Chem.*, vol. 33, 1990, pp. 2358-2368, XP-001024801.
Moshchitskii et al., "Smiles rearrangement of tetrachloropyridyl methyl-hydroxyphenyl sulfone", *Chemistry of Heterocyclic Compounds*, vol. 15, No. 7, 1979, pp. 1085-1088.
Ong et al., "Synthesis and Analgesic Activity of Some Spiro[dibenz[*bf*]oxepin-10,4'-piperidine] Derivatives", *J. Med. Chem.*, vol. 22, No. 7,1979, pp. 834-839, XP-002347163.
Rajsner et al., "Fluorinated tricyclic Neuroleptics: Synthesis and Pharmacology of 8-Fluoro-4-(4-Methylpiperazino)-4,5-Dihydrothieno[2,3-*b*]-1-Benzothiepin", *Collection Czechoslov. Chem. Commun.*, vol. 44, 1979, pp. 2997-3007, XP-002347164.
Selvi et al., "Vilsmeier cyclization of 2-amino phenoxyacetic acid", *Synthetic Communications*, vol. 31, No. 14, 2001, pp. 2199-2202.
Sindelar et al., "Synthesis of 3-Chloro-5-(4-Methylpiperazino)-6,7-Dihydro-5*H*-Dibenzo[*b,g*]Thiocin, An Eight-Membered Ring Homologue of The Neuroleptic Agent Octoclothepin", *Collection Czechoslov. Chem. Commun.*, vol. 45, 1980, pp. 491-503, XP-002347160.
Sindelar et al., "Fluorinated Tricyclic Neuroleptics with Prolonged Action: 3-Fluoro-8-Trifluoromethyl Derivatives of 10-(4-Methylpiperazino)- and 10-[4-(2-Hydroxyethyl)Piperazino]-10,11-Dihydrodibenzo-[*b,f*]Thiepin", *Collection Czechoslov. Chem. Commun.*, vol. 46, 1981, pp. 118-140, XP-002347168.

Sindler-Kulyk et al., "Synthesis of New 3-(Phenoxyphenyl)sydnones", *J. Heterocyclic Chem.*, vol. 29, No. 2, 1992, pp. 1013-1015, XP-002347161.
Stokker et al., "3-Hydroxy-3-methylglutaryl-coenzyme A Reductase Inhibitors. 5. 6-(Fluoren-9-yl)- and 6-(Fluoren-9-ylidenyl)-3,5-dihydroxyhexanoic Acids and Their Lactone Derivatives", *J. Med. Chem.*, vol. 29, 1986, pp. 852-855.
Thuillier, G., "Derives des acides 24 aryloxyacetiques a activite neurotrope", *Chimique Therapeutique*, vol. 1, No. 2, 1966, pp. 82-86.
Walsh et al., "Antiinflammatory Activity of N-(2-Benzoylphenyl)alanine Derivatives", *J. Med. Chem.*, vol. 27, 1984, pp. 1317-1321, XP-002347162.
Wheatley et al., "2-Benzylphenol Derivatives. III. Basic Ethers", *Journal of American Chemical Society*, vol. 71, No. 11, 1949, pp. 3795-3797.
Database CA [Online] Chemical Abstracts Service, Columbus, Ohio, US; XP002372494 retrieved from STN Database accession No. 1956:16264 abstract & OTT, Donald G. et al: "A carbon-14 tracer study of the alkaline rearrangement of chlorophenanthraquinones" *Journal of the American Chemical Society*, vol. 77, 2325-2329 CODEN:JACSAT; ISSN:0002-7863, 1955.
Database CAPLUS [Online] Chemical Abstracts Service, Columbus, Ohio, US; 1992, XP002372495 retrieved from STN Database accession No. 1992:255529 abstract & RAM, Bhagat et al: "Potential hypolipidemic agents part VI: synthesis and biological activity of some new 4-chloro/methyl-2-pyrazolylphenoxy alkanoates", *Indian Drugs*, vol. 29, No. 6, 1992, pp. 258-262.
Database WPI 1-3, 5, Section Ch, Week 200365 19, 20, Derwent Publications Ltd., London, GB, AN 2003-689635 XP-002301315, WO03068744A1, Ishihara Sangyo Kaisha, Ltd., Aug. 21, 2003.
STN International, File CAPLUS, CAPLUS accession 1-10, No. 1987:597776, document No. 107:197776, Otsuka Pharmaceutical Factory, "Preparation of aminophenol derivatives as anticoagulants, analgesics, hypotensives, and diuretics", JP, A2, 62108859, 19870520.
STN International, File CAPLUS, CAPLUS accession 1-5, 10, No. 1979:186607, document No. 90:186607, Ciba-Geigy, "Phenoxyphenoxyalkanecardoxylic acid derivatives", DE, A1, 2832435, 19790208.
STN International, File CAPLUS, CAPLUS accession 1-5, 10, No. 1971:53748, document No. 74:53748, Walker et al., "Synthesis of 5-phenyl-2,3,4,5-tetrahydro-1,4-benzoxazepines and corresponding 3-ones", & *Journal of Organic Chemistry* (1970), 36(2), 305-308.
STN International, File CAPLUS, CAPLUS accession 1-3, 5, 10, No. 1992:407796, document No. 117:7796, Tokuyama Soda Co., Ltd., "Preparation of thienyloxphenoxy group-containing carboxylic acids as microbicides", JP, A2, 04021677, 19920124.
STN International, File CAPLUS, CAPLUS accession 1-3, 5, 10, No. 1975:402045, document No. 83:2045, Shiley et al., "Fungicidal activity of some fluoroaromatic compounds", *Journal of Fluorine Chemistry* (1975), 5(4), 371-376.
STN International, File CAPLUS, CAPLUS accession 1, 3, 5, 10, No. 1972:405106, document No. 77:5106, Oniscu et al., "Monoethanolaminosulfonyl-,diethanolaminosulfonyl- and morpholinosulfonyl-phenoxyacetic derivatives", Buletinul Institutului Politehnic din Iasi, (1971), 14(3-4), 101-114.

STN International, File CAPLUS, CAPLUS accession 1, 3, 5, 10, No. 1961:22702, document No. 55:22702, Takano, K., "Condensation products of furfuryl alcohol. IV. Condensation products of furfuryl alcohol with cresols", Nippon Kagaku Zasshi (1959), 80, 678-681.
STN International, File CAPLUS, CAPLUS accession 1, 3-5, 10, No. 1958:25331, document No. 52:25331, Landa et al., "Properties of sulfide catalysts. V. Preparation of alkylphenols", Chemicke Listy pro Vedu a Prumysl (1957), 51, 1851-1857.
STN Intenational, File CAPLUS, CAPLUS accession 1, 3, 5, 10, No. 1971:498288, document No. 75:98288, Botez et al., "Phenoxybutyric acid sulfamides. 1. Sulfamide derivatives of the α-phenoxy-, α-cresoxy-, and α-xylenoxybutyric acids", Buletinul Institutului Politehnic din Iasi (1970), 16(1-2), 161-172.
STN International, File CAPLUS, CAPLUS accession 1-7, 10, No. 1986:109631, document No. 104:109631, Yoshitomi Pharmaceutical Industries, Ltd., "Imidazole derivatives", JP, A2, 60142965, 19850729.
Vippagunta et al., "Crystalline solids", *Advanced Drug Delivery Reviews* 48:3-26 (2001).
Inflammatory Bowel Disease [online]{retrieved on Apr. 7, 2008 from the internet} {URL:http://www.emedicinehealth.com/script/main/art.asp?articlekey=59121&pf=3&page=8}.
Rheumatoid arthritis [online] {retrieved on Apr. 7, 2008 from the internet} {URL:http://www.nlm.nih.gov/medlineplus/ency/article/000431.htm}.
Asthma [online] [retrieved on May 30, 2008] retrieved from the Internet URL:http://www.nlm.nih.gov/medlineplus/ency/article/000141.htm.
Lehmler et al., "Synthesis of hydroxylated PCB metabolites with the Suzuki-coupling", *Chemosphere* 45:1119-1127 (2001).
USPTO Office Action in U.S. Appl. No. 10/551,783, mailed May 17, 2011, 8 pages.
Fish & Richardson P.C., Response to Notice of Allowance of Apr. 8, 2011 in U.S. Appl. No. 10/569,065, filed Jul. 7, 2011, 2 pages.
USPTO Restriction Requirement in U.S. Appl. No. 13/190,881 mailed Oct. 28, 2011, 11 pages.
Fish & Richardson P.C., Response to Notice of Allowance of May 6, 2011 in U.S. Appl. No. 11/571,707, filed Aug. 3, 2011, 3 pages.
USPTO Non-Final Office Action in U.S. Appl. No. 11/576,372, mailed Dec. 5, 2011, 13 pages.
Fish & Richardson P.C., Amendment in Reply to Action of Jan. 26, 2011 in U.S. Appl. No, 12/089,275, filed Jul. 26, 2011, 19 pages.
USPTO Notice of Allowance in U.S. Appl. No. 12/089,275, mailed Nov. 7, 2011, 18 pages.
Fish & Richardson P.C., Response to Notice of Allowance of Apr. 12, 2011 in U.S. Appl. No. 12/089,276, filed Jul. 11, 2011, 2 pages.
USPTO Non-Final Office Action in U.S. Appl. No. 12/973,395, mailed Oct. 13, 2011, 19 pages.
USPTO Non-Final Office Action in U.S. Appl. No. 12/092,431, mailed Aug. 17, 2011, 13 pages.
USPTO Non-Final Office Action in U.S. Appl. No. 12/096,557, mailed Nov. 15, 2011, 30 pages.

* cited by examiner

BIPHENYLOXYACETIC ACID DERIVATIVES FOR THE TREATMENT OF RESPIRATORY DISEASE

CROSS-REFERENCE TO RELATED APPLICATIONS

This application is a divisional of U.S. application Ser. No. 11/574,076, filed on Feb. 22, 2007, now U.S. Pat. No. 7,737,135 which is the U.S. National Stage of International Application No. PCT/GB2005/003255, filed Aug. 22, 2005, which in turn claims the benefit of Great Britain Application Serial No. 0418830.6, filed on Aug. 24, 2004; each of these prior applications is incorporated herein by reference in its entirety.

The present invention relates to substituted phenoxyacetic acids as useful pharmaceutical compounds for treating respiratory disorders, pharmaceutical compositions containing them, and processes for their preparation.

EPA 1 170 594 discloses methods for the identification of compounds useful for the treatment of disease states mediated by prostaglandin D2, a ligand for orphan receptor CRTH2. GB 1356834 discloses a series of compounds said to possess anti-inflammatory, analgesic and antipyretic activity. It has been found that certain phenoxyacetic acids are active at the CRTH2 receptor, and as a consequence are expected to be potentially useful for the treatment of various respiratory diseases, including asthma and COPD.

In a first aspect the invention therefore provides a compound of formula (I) or a pharmaceutically acceptable salt thereof:

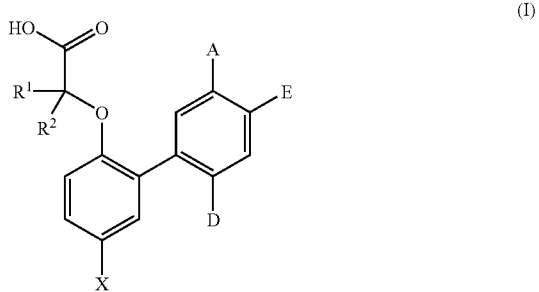

in which:

X is halogen, or $C_{1-2}$ alkyl which is substituted by one or more halogen atoms;

A and E are independently selected from halogen, $SO_2NR^3R^4$, $SO_nR^5$ (n=1 or 2), $CONR^3R^4$, or $C_{1-3}$ alkyl which can be optionally substituted by one or more halogen atoms;

D is hydrogen or fluorine;

$R^1$ and $R^2$ independently represent a hydrogen atom, or a $C_{1-3}$ alkyl group;

or $R^1$ and $R^2$ together can form a 3-8 membered ring optionally containing one or more atoms selected from O, S, $NR^6$ and itself optionally substituted by one or more $C_1$-$C_3$ alkyl;

$R^3$ and $R^4$ independently represent hydrogen, $C_3$-$C_7$ cycloalkyl or $C_{1-6}$alkyl, the latter two groups being optionally substituted by one or more substituents independently selected from halogen, $C_3$-$C_7$ cycloalkyl, $OR^6$ and $NR^7R^8$;

or $R^3$ and $R^4$ together with the nitrogen atom to which they are attached can form a 3-8 membered saturated heterocyclic ring optionally containing one or more atoms selected from O, S(O)$_n$ (where n=0, 1 or 2), $NR^8$, and itself optionally substituted by halogen or $C_{1-3}$ alkyl;

$R^5$ is $C_1$-$C_6$ alkyl or $C_{3-7}$ cycloalkyl, which may be optionally substituted by halogen atoms;

$R^6$ is hydrogen or $C_1$-$C_6$ alkyl;

$R^7$ and $R^8$ independently represent hydrogen, $C_{1-6}$ alkyl or $C_{3-7}$ cycloalkyl or $R^7$ and $R^8$ together with the nitrogen atom to which they are attached can form a 3-8 membered saturated heterocyclic ring as defined above for $R^3$ and $R^4$.

In the context of the present specification, unless otherwise indicated, an alkyl group or an alkyl moiety in a substituent group may be linear or branched.

Heterocyclic rings as defined for $R^3$ and $R^4$ or $R^7$ and $R^8$ means saturated heterocycles, examples include morpholine, azetidine, pyrrolidine, piperidine and piperazine.

Preferably X is trifluoromethyl, chloro or fluoro.

Preferably A and E independently represent trifluoromethyl, $C_{1-3}$alkyl, halogen, $SOR^5$, $SO_2R^5$, $CONR^3R^4$, or $SO_2NR^3R^4$. More preferably A and E independently represent trifluoromethyl, methyl, fluoro, chloro, $SO_2Me$, $SO_2Et$, $SO_2iPr$, $SO_2NR^3R^4$ or $CONR^3R^4$.

More preferably A is trifluoromethyl, methyl, fluoro or chloro.

More preferably E is $SO_2Me$, $SO_2Et$, $SO_2iPr$, $SO_2NR^3R^4$ where $R^3$ and $R^4$ together form a morpholine ring or E is $CONR^3R^4$ where $R^3$ and $R^4$ together form a pyrrolidine, piperidine, azetidine or isoxazoline ring, each optionally substituted by halogen or $C_1$-$C_3$ alkyl, or E is $CONR^3R^4$ where $R^3$ and $R^4$ independently represent hydrogen, $C_3$-$C_7$ cycloalkyl or $C_{1-6}$alkyl. The alkyl groups may be linear or branched.

Most preferably E is $SO_2Me$, $SO_2Et$, $SO_2NR^3R^4$ where $R^3$ and $R^4$ together form a morpholine ring or E is $CONR^3R^4$ where $R^3$ and $R^4$ together form a pyrrolidine, piperidine, azetidine or isoxazoline ring, each optionally substituted by fluoro or methyl, or E is $CONR^3R^4$ where $R^3$ and $R^4$ independently represent hydrogen, $C_3$-$C_7$ cycloalkyl or $C_{3-6}$ alkyl. The alkyl groups may be linear or branched.

Preferably $R^1$ and $R^2$ are independently hydrogen or $C_{1-3}$ alkyl, more preferably $R^1$ and $R^2$ are both hydrogen or one is hydrogen and the other is methyl.

Preferably D is hydrogen or fluorine, more preferably hydrogen.

Preferred substituents A, D, E, X, $R^1$ and $R^2$ are those exemplified herein. Preferred compounds of the invention include:

(2S)-2-[[4'-(methylsulfonyl)-3',5-bis(trifluoromethyl)[1,1'-biphenyl]-2-yl]oxy]-propanoic acid;

[[3',5-Dichloro-4'-(methylsulfonyl)[1,1'-biphenyl]-2-yl]oxy]acetic acid;

[[3',5-Dichloro-4'-(methylsulfinyl)[1,1'-biphenyl]-2-yl]oxy]acetic acid;

(2S)-2-[[3',5-Dichloro-4'-(methylsulfonyl)[1,1'-biphenyl]-2-yl]oxy]propanoic acid;

(2S)-2-[4-chloro-2-[2,5-difluoro-4-(4-morpholinylsulfonyl)phenoxy]phenoxy]-propanoic acid;

[[3'-Fluoro-4'-[(1-methylethyl)sulfonyl]-5-(trifluoromethyl)[1,1'-biphenyl]-2-yl]oxy]acetic acid;

[[5-Chloro-4'-(methylsulfonyl)-3'-(trifluoromethyl)[1,1'-biphenyl]-2-yl]oxy]-acetic acid;

[[5-Fluoro-4'-(methylsulfonyl)-3'-(trifluoromethyl)[1,1'-biphenyl]-2-yl]oxy]-acetic acid;

[[4'-(Ethylsulfonyl)-3',5-bis(trifluoromethyl)[1,1'-biphenyl]-2-yl]oxy]acetic acid;

(2S)-2-[[4'-(Ethylsulfonyl)-3',5-bis(trifluoromethyl)[1,1'-biphenyl]-2-yl]oxy]propanoic acid;
[[5-Chloro-4'-(4-morpholinylsulfonyl)-3'-(trifluoromethyl)[1,1'-biphenyl]-2-yl]oxy]acetic acid;
(2S)-2-[[5-Chloro-4'-(4-morpholinylsulfonyl)-3'-(trifluoromethyl)[1,1'-biphenyl]-2-yl]oxy]propanoic acid;
[[5-Chloro-4'-(1-pyrrolidinylcarbonyl)-3'-(trifluoromethyl)[1,1'-biphenyl]-2-yl]oxy]-acetic acid;
(2S)-2-[[5-Chloro-4'-(1-pyrrolidinylcarbonyl)-3'-(trifluoromethyl)[1,1'-biphenyl]-2-yl]oxy]propanoic acid;
[[5-Chloro-4'-(ethylsulfonyl)-3'-(trifluoromethyl)[1,1'-biphenyl]-2-yl]oxy]acetic acid;
(2S)-2-[[5-Chloro4'-(methylsulfonyl)-(3'-trifluoromethyl)-[1,1'-biphenyl]-2-yl]oxy]propanoic acid;
(2S)-2-[[5-Chloro-3'-fluoro-4'-(methylsulfonyl)[1,1'-biphenyl]-2-yl]oxy]propanoic acid;
[[3',5-dichloro-4'-(1-pyrrolidinylcarbonyl)[1,1'-biphenyl]-2-yl]oxy]-acetic acid;
[[3',5-dichloro-4'-(4-morpholinylcarbonyl)[1,1'-biphenyl]-2-yl]oxy]-acetic acid;
[[4'-(1-azetidinylcarbonyl)-3',5-dichloro[1,1'-biphenyl]-2-yl]oxy]-acetic acid;
[[3',5-dichloro-4'-[[(2R,6S)-2,6-dimethyl-1-piperidinyl]carbonyl][1,1'-biphenyl]-2-yl]oxy]-acetic acid;
[[3',5-dichloro-4'-[(2-methyl-1-pyrrolidinyl)carbonyl][1,1'-biphenyl]-2-yl]oxy]-acetic acid;
[[3',5-dichloro-4'-(2-isoxazolidinylcarbonyl)[1,1'-biphenyl]-2-yl]oxy]-acetic acid;
[[5-chloro-3'-fluoro-4'-(1-pyrrolidinylcarbonyl)[1,1'-biphenyl]-2-yl]oxy]-acetic acid;
(2S)-2-[[5-chloro-3'-fluoro-4'-(1-pyrrolidinylcarbonyl)[1,1'-biphenyl]-2-yl]oxy]-propanoic acid;
[[3'-methyl-4'-(1-piperidinylcarbonyl)-5-(trifluoromethyl)[1,1'-biphenyl]-2-yl]oxy]-acetic is acid;
[[3'-methyl-4'-(1-pyrrolidinylcarbonyl 1)-5-(trifluoromethyl)[1,1'-biphenyl]-2-yl]oxy]-acetic acid;
(2S)-2-[[4'-[[bis(1-methylethyl)amino]carbonyl]-5-chloro-3'-fluoro[1,1'-biphenyl]-2-yl]oxy]-propanoic acid;
(2S)-2-[[5-chloro-4'-[(ethylmethylamino)carbonyl]-3'-fluoro[1,1'-biphenyl]-2-yl]oxy]-propanoic acid;
(2S)-2-[[5-chloro-3'-fluoro-4'-[[methyl(1-methylethyl)amino]carbonyl][1,1'-biphenyl]-2-yl]oxy]-propanoic acid;
(2S)-2-[[5-chloro-4'-[(diethylamino)carbonyl]-3'-fluoro[1,1'-biphenyl]-2-yl]oxy]-propanoic acid;
(2S)-2-[[5-chloro-4'-[(3,3-difluoro-1-pyrrolidinyl)carbonyl]-3'-fluoro[1,1'-biphenyl]-2-yl]oxy]-propanoic acid;
(2S)-2-[[4'-[[(1,1-dimethylethyl)amino]carbonyl]-3'-fluoro-5-(trifluoromethyl) [1,1'-biphenyl]-2-yl]oxy]-propanoic acid;
(2S)-2-[[5-chloro-3'-fluoro-4'-[[(1-methylethyl)amino]carbonyl][1,1'-biphenyl]-2-yl]oxy]-propanoic acid;
(2S)-2-[[5-chloro-3'-fluoro-4'-[[(2-methylpropyl)amino]carbonyl][1,1'-biphenyl]-2-yl]oxy]-propanoic acid;
(2S)-2-[[3'-fluoro-4'-(1-pyrrolidinylcarbonyl)-5-(trifluoromethyl)[1,1'-biphenyl]-2-yl]oxy]-propanoic acid;
(2S)-2-[[3',5-dichloro-4'-(1-pyrrolidinylcarbonyl)[1,1'-biphenyl]-2-yl]oxy]-propanoic acid;
(2S)-2-[[5-chloro-3'-methyl-4'-(1-pyrrolidinylcarbonyl)[1,1'-biphenyl]-2-yl]oxy]-propanoic acid;
[[5-chloro-3'-methyl-4'-(1-pyrrolidinylcarbonyl)[1,1'-biphenyl]-2-yl]oxy]-acetic acid;
[[3'-fluoro-4'-(1-pyrrolidinylcarbonyl)-5-(trifluoromethyl)[1,1'-biphenyl]-2-yl]oxy]-acetic acid;
(2S)-2-[[3'-methyl-4'-(1-pyrrolidinylcarbonyl)-5-(trifluoromethyl)[1,1'-biphenyl]-2-yl]oxy]-propanoic acid;

[[3',5-difluoro-4'-(1-pyrrolidinylcarbonyl)[1,1'-biphenyl]-2-yl]oxy]-acetic acid;
(2S)-2-[[3',5-difluoro-4'-(1-pyrrolidinylcarbonyl)[1,1'-biphenyl]-2-yl]oxy]-propanoic acid;
(2S)-2-[[5-chloro-3'-fluoro-4'-[(2-methyl-1-pyrrolidinyl)carbonyl][1,1'-biphenyl]-2-yl]oxy]-propanoic acid;
(2S)-2-[[5-chloro-3'-fluoro-4'-[[(2S)-2-methyl-1-pyrrolidinyl]carbonyl][1,1'-biphenyl]-2-yl]oxy]-propanoic acid;
(2S)-2-[[5-chloro-3'-fluoro-4'-[[(2R)-2-methyl-1-pyrrolidinyl]carbonyl][1,1'-biphenyl]-2-yl]oxy]-propanoic acid;
(2S)-2-[[4'-[(cyclopentylamino)carbonyl]-3'-fluoro-5-(trifluoromethyl)[1,1'-biphenyl]-2-yl]oxy]-propanoic acid;
(2S)-2-[[3'-fluoro-4'-[[(1-methylethyl)amino]carbonyl]-5-(trifluoromethyl)[1,1'-biphenyl]-2-yl]oxy]-propanoic acid;
(2S)-2-[[4'-[(ethylamino)carbonyl]-3'-fluoro-5-(trifluoromethyl)[1,1'-biphenyl]-2-yl]oxy]-propanoic acid;
(2S)-2-[[5-chloro-4'-[[(1,1-dimethylethyl)amino]carbonyl]-3'-fluoro[1,1'-biphenyl]-2-yl]oxy]-propanoic acid;
(2S)-2-[[5-chloro-4'-[(cyclopentylamino)carbonyl]-3'-fluoro[1,1'-biphenyl]-2-yl]oxy]-propanoic acid;
(2S)-2-[[5-chloro-4'-[(cyclopropylamino)carbonyl]-3'-fluoro[1,1'-biphenyl]-2-yl]oxy]-propanoic acid;
(2S)-2-[[5-chloro-4'-[[(1-ethylpropyl)amino]carbonyl]-3'-fluoro[1,1'-biphenyl]-2-yl]oxy]-propanoic acid;
(2S)-2-[[5-chloro-3'-fluoro-4'-[(methylamino)carbonyl][1,1'-biphenyl]-2-yl]oxy]-propanoic acid;
(2S)-2-[[5-chloro-4'-[[(1,1-dimethylethyl)amino]carbonyl]-3'-methyl[1,1'-biphenyl]-2-yl]oxy]-propanoic acid;
[[5-chloro-4'-[[(1-ethylpropyl)amino]carbonyl]-3'-fluoro[1,1'-biphenyl]-2-yl]oxy]-acetic acid;
[[5-chloro-3'-fluoro-4'-[(methylamino)carbonyl][1,1'-biphenyl]-2-yl]oxy]-acetic acid;
(2S)-2-[[5-chloro-4'-[(ethylamino)carbonyl]-3'-fluoro[1,1'-biphenyl]-2-yl]oxy]-propanoic acid;
(2S)-2-[[5-chloro-4'-[(cyclobutylamino)carbonyl]-3'-fluoro[1,1'-biphenyl]-2-yl]oxy]-propanoic acid;
(2S)-2-[[5-chloro-4'-[[(1,1-dimethylpropyl)amino]carbonyl]-3'-fluoro[1,1'-biphenyl]-2-yl]oxy]-propanoic acid;
(2S)-2-[[5-chloro-3'-fluoro-4'-[[(3-methylbutyl)amino]carbonyl][1,1'-biphenyl]-2-yl]oxy]-propanoic acid;
and pharmaceutically acceptable salts thereof.

Certain compounds of formula (I) are capable of existing in stereoisomeric forms. It will be understood that the invention encompasses all geometric and optical isomers of the compounds of formula (I) and mixtures thereof including racemates. Tautomers and mixtures thereof also form an aspect of the present invention.

The compound of formula (I) above may be converted to a pharmaceutically acceptable salt or solvate thereof, preferably a basic addition salt such as sodium, potassium, calcium, aluminium, lithium, magnesium, zinc, benzathine, chloroprocaine, choline, diethanolamine, ethanolamine, ethyldiamine, meglumine, tromethamine or procaine, or an acid addition salt such as a hydrochloride, hydrobromide, phosphate, acetate, fumarate, maleate, tartrate, citrate, oxalate, methanesulphonate or p-toluenesulphonate.

It will be appreciated by those skilled in the art that in the processes of the present invention certain functional groups in the starting reagents or intermediate compound may need to be protected by protecting groups. Thus, the preparation of the compound of formula (I) may involve, at an appropriate stage, the removal of one or more protecting groups. The protection and deprotection of functional groups is fully described in 'Protective Groups in Organic Chemistry', edited by J. W. F. McOmie, Plenum Press (1973), and 'Protective Groups in Organic Synthesis', 3rd edition, T. W. Greene & P. G. M. Wuts, Wiley Interscience (1999).

Compounds of formula (I) can be prepared by reaction of a compound of formula (II):

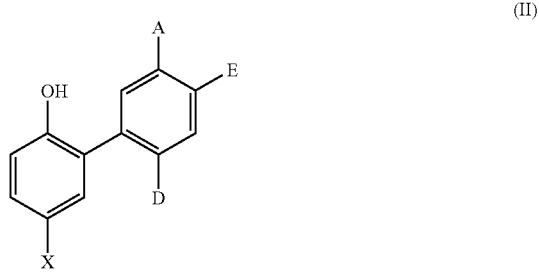

(II)

in which X, A, D and E are as defined in formula (I) or are protected derivatives thereof, with to a compound of formula (III):

(III)

Where $R^1$ and $R^2$ are as defined in formula (I) or are protected derivatives thereof, $R^9$ is H or $C_1$-$C_{10}$ alkyl group and L is a leaving group, and optionally thereafter in any order:
  removing any protecting group
  hydrolysing the ester group $R^9$ to the corresponding acid
  oxidation of sulphides to sulphoxides or sulphones
  forming a pharmaceutically acceptable salt.

The reaction can be carried out in a suitable solvent such as acetonitrile or DMF using a base such as potassium carbonate or the like. Suitable groups $R^9$ include $C_{1-6}$ alkyl groups such as methyl, ethyl or tert-butyl. Suitable L is a leaving group such as tosylate or halo, in particular chlorine or bromine. L may also be hydroxy so that a Mitsunobu reaction may be performed with compound (II) using for example triphenylphosphine and diethyl azodicarboxylate.

Hydrolysis of the ester group $R^9$ can be carried out using routine procedures, for example treatment of methyl and ethyl esters with aqueous sodium hydroxide, and treatment of tert-butyl esters with acids such as trifluoroacetic acid.

Compounds of formula (II) can be prepared by reaction of a compound of formula (IV) with a compound of formula (V) via a Suzuki coupling reaction followed by deprotection of $R^{10}$:

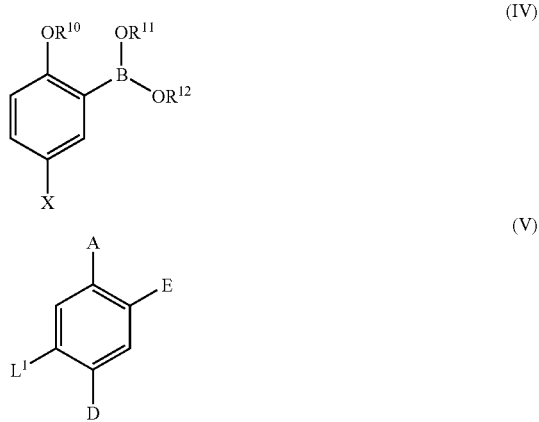

in which X, A, D and E are as defined in formula (I) or are protected derivatives thereof, $R^{10}$ is H or a suitable protecting group, for example benzyl or methyl, $L^1$ is iodide, bromide, chloride or triflate and $R^{11}$ and $R^{12}$ are H or $C_1$-$C_6$ alkyl groups or $R^{11}$ and $R^{12}$ together can form a 5 or 6 membered ring optionally substituted by one or more $C_1$-$C_3$ alkyl.

The reaction can be carried out in a suitable solvent such as dioxane using a palladium catalyst such as [1,1-bis(diphenylphosphino)ferrocene]dichloropalladium and a base such as cesium fluoride, preferably at elevated temperatures.

When $R^{10}$ is a protecting group such as benzyl it can be removed using hydrogen with a suitable catalyst for example platinum or palladium on charcoal. If the group $R^{10}$ is alkyl for example methyl, then it can be cleaved using borontribromide in a suitable solvent such as dichloromethane.

Some compounds of formula (IV) are commercially available. Certain compounds of formula (IV) can be prepared from a compound of formula (VI) by formation of an organometallic (VII) followed by reaction with a borate ester, as outlined in Scheme I.

Scheme I

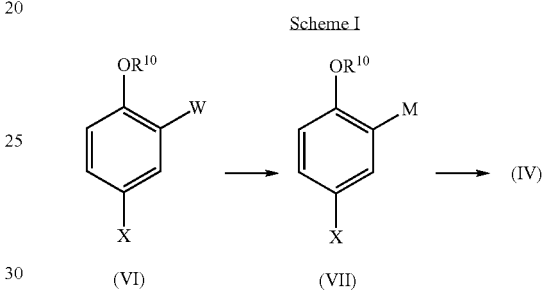

in which X, is as defined in formula (I) or are protected derivatives thereof, $R^{10}$ is as defined in formula (IV), W is hydrogen or halogen and M is a metal such as Na or Li. For example when $R^{10}$ is benzyl and E is bromine, butyl lithium can be used to form the intermediate (VII) where M=Li. The reaction is performed at −78° C. in diethylether, then quenched with a borate ester such as trimethylborate.

Compounds of formula (II) may also be prepared by reaction of a compound of formula (XI) with a compound of formula (XII) using Suzuki coupling methodology.

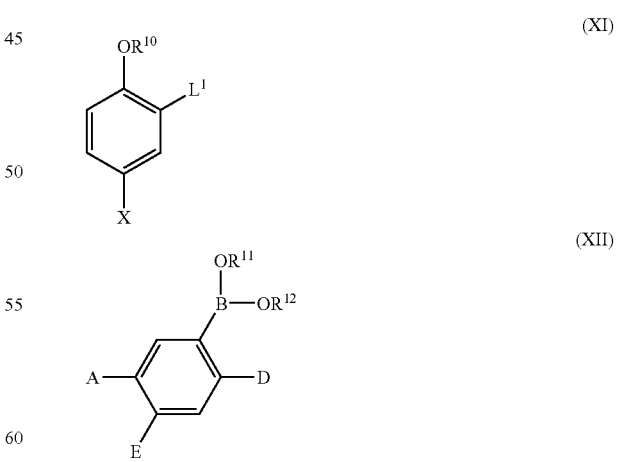

in which X, A, D, E, $R^{10}$, $L^1$, $R^{11}$ and $R^{12}$ are as defined above and compounds of formula (XI) and (XII) can be made using the same methodology as above.

The sequence of the steps above may be changed, for example a compound of formula (I) may be formed by the reaction of a compound of formula (XVI) with a compound of formula (XII) using a Suzuki coupling.

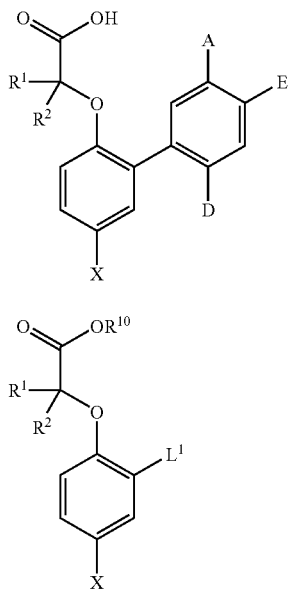

Or, compounds of formula (I) can be prepared by reaction of a compound of formula (XVII) with a compound of formula (V):

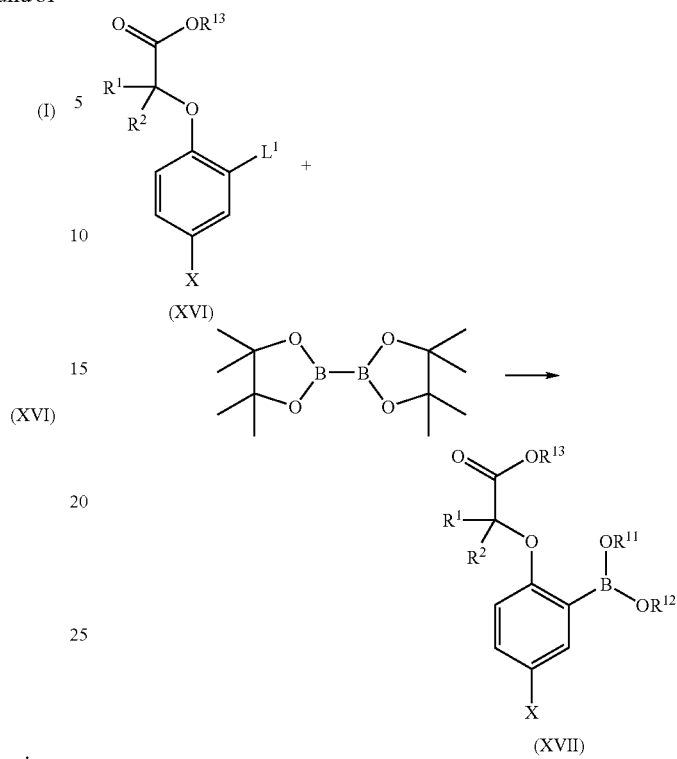

Where the groups A, D, E, $L^1$, X, $R^1$ and $R^2$ are as defined above or protected derivates thereof. $R^{13}$ is hydrogen or $C_1$-$C_6$ alkyl for example methyl ethyl or tertiary butyl. If $R^{13}$ is an ester group it is subsequently hydrolysed using either acidic or basic conditions, such as TFA or NaOH. Compounds of formula (XVII) can be prepared as outlined in WO2004089885 or by reacting a compound of formula (XVII) with bis(pinocolato)diboron using the Suzuki reaction.

A compound of formula (XII) may be prepared by methods A or B.

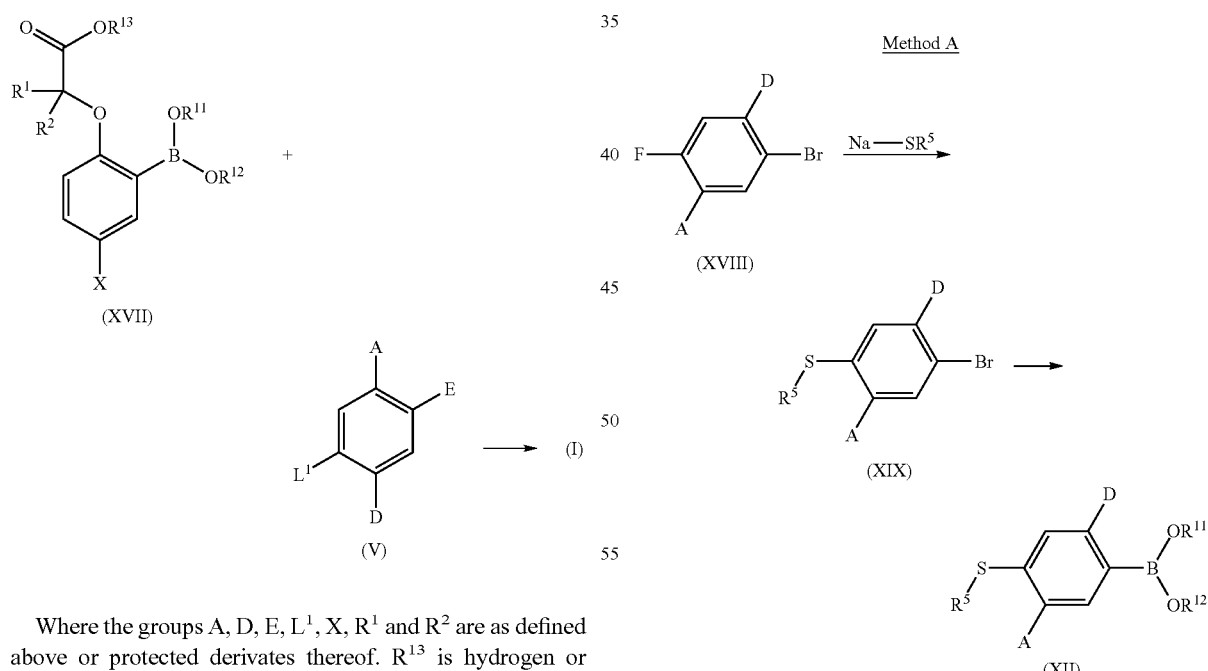

Compounds of formula (XII) where the group E is $SR^5$ can be synthesised by displacing the Fluorine with $R^5SNa$ in a suitable solvent such as DMF at 50° C. Compounds of formula (XIX) can be converted to the boronic acid using BuLi, then reacting with a borate ester as outlined previously. Alternatively the compounds of formula (XVII) can be prepared by a palladium catalysed coupling of compounds of formula (XIX) with a suitable boronic ester, for example bis(pinocolato)diboron.

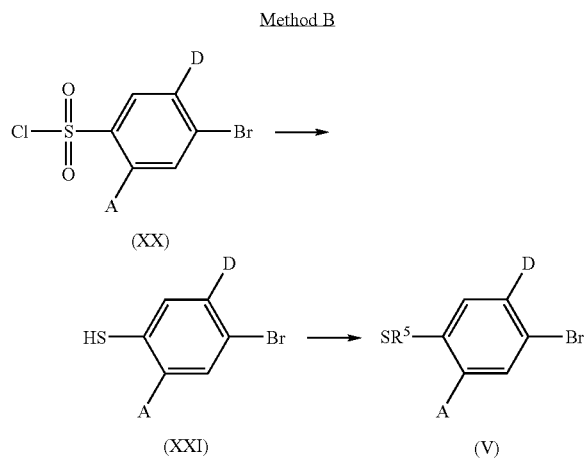

Compounds of formula (XIX) can also be prepared from compounds of formula (XX) where the chlorosulphonic acid is reduced to the thiol using triphenylphosphine, subsequently alkylated using an alkyl halide such as alkyl iodide or bromide.

Compounds of formula (V) where the group E is amide can be prepared by method C:

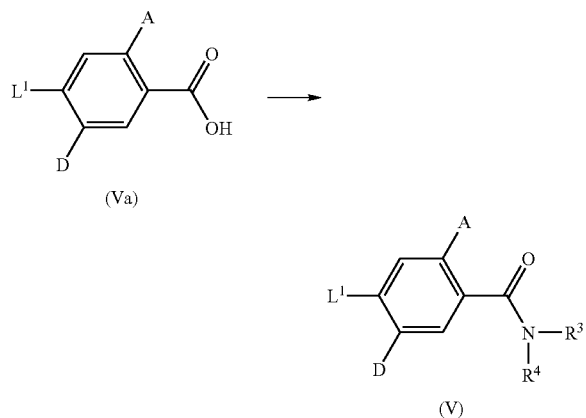

in which a compound of formula (Va) is converted to the acid chloride using a reagent such as oxalyl chloride and subsequently reacted with an amine in a suitable solvent such as dichloromethane. The groups A, D and $L^1$ are as defined for compounds of formula (V) or protected derivates thereof.

Compounds of formula (Va) are commercially available or can be readily synthesised using literature procedures by those skilled in the art.

Novel intermediates of the general formulae given above form a further aspect of the invention.

In a further aspect, the present invention provides the use of a compound of formula (I), a prodrug, pharmaceutically acceptable salt or solvate thereof for use in therapy.

The compounds of formula (I) have activity as pharmaceuticals, in particular as modulators of CRTh2 receptor activity, and may be used in the treatment (therapeutic or prophylactic) of conditions/diseases in human and non-human animals which are exacerbated or caused by excessive or unregulated production of $PGD_2$ and its metabolites. Examples of such conditions/diseases include:

1. respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus;

2. bone and joints: arthritides associated with or including osteoarthritis/osteoarthrosis, both primary and secondary to, for example, congenital hip dysplasia; cervical and lumbar spondylitis, and low back and neck pain; rheumatoid arthritis and Still's disease; seronegative spondyloarthropathies including ankylosing spondylitis, psoriatic arthritis, reactive arthritis and undifferentiated spondarthropathy; septic arthritis and other infection-related arthopathies and bone disorders such as tuberculosis, including Potts' disease and Poncet's syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositis and polymyositis; polymalgia rheumatica; juvenile arthritis including idiopathic inflammatory arthritides of whatever joint distribution and associated syndromes, and rheumatic fever and its systemic complications; vasculitides including giant cell arteritis, Takayasu's arteritis, Churg-Strauss syndrome, polyarteritis nodosa, microscopic polyarteritis, and vasculitides associated with viral infection, hypersensitivity reactions, cryoglobulins, and paraproteins; low back pain; Familial Mediterranean fever, Muckle-Wells syndrome, and Familial Hibernian Fever, Kikuchi disease; drug-induced arthalgias, tendonititides, and myopathies;

3. pain and connective tissue remodelling of musculoskeletal disorders due to injury [for example sports injury] or disease: arthitides (for example rheumatoid arthritis, osteoarthritis, gout or crystal arthropathy), other joint disease (such as intervertebral disc degeneration or temporomandibular joint degeneration), bone remodelling disease (such as osteoporosis, Paget's disease or osteonecrosis), polychondritis, scleroderma, mixed connective tissue disorder, spondyloarthropathies or periodontal disease (such as periodontitis);

4. skin: psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous to eosinophilias, alopecia greata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions;

5. eyes: blepharitis; conjunctivitis, including perennial and vernal allergic conjunctivitis; iritis; anterior and posterior uveitis; choroiditis; autoimmune; degenerative or inflammatory disorders affecting the retina; ophthalmitis including sympathetic ophthalmitis; sarcoidosis; infections including viral, fungal, and bacterial;

6. gastrointestinal tract: glossitis, gingivitis, periodontitis; oesophagitis, including reflux; eosinophilic gastro-enteritis, mastocytosis, Crohn's disease, colitis including ulcerative colitis, proctitis, pruritis ani; coeliac disease, irritable bowel syndrome, and food-related allergies which may have effects remote from the gut (for example migraine, rhinitis or eczema);

7. abdominal: hepatitis, including autoimmune, alcoholic and viral; fibrosis and cirrhosis of the liver; cholecystitis; pancreatitis, both acute and chronic;

8. genitourinary: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female);

9. allograft rejection: acute and chronic following, for example, transplantation of kidney, heart, liver, lung, bone marrow, skin or cornea or following blood transfusion; or chronic graft versus host disease;

10. CNS: Alzheimer's disease and other dementing disorders including CJD and nvCJD; amyloidosis; multiple sclerosis and other demyelinating syndromes; cerebral atherosclerosis and vasculitis; temporal arteritis; myasthenia gravis; acute and chronic pain (acute, intermittent or persistent, whether of central or peripheral origin) including visceral pain, headache, migraine, trigeminal neuralgia, atypical facial pain, joint and bone pain, pain arising from cancer and tumor invasion, neuropathic pain syndromes including diabetic, post-herpetic, and HIV-associated neuropathies; neurosarcoidosis; central and peripheral nervous system complications of malignant, infectious or autoimmune processes;

11. other auto-immune and allergic disorders including Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome;

12. other disorders with an inflammatory or immunological component; including acquired immune deficiency syndrome (AIDS), leprosy, Sezary syndrome, and paraneoplastic syndromes;

13. cardiovascular: atherosclerosis, affecting the coronary and peripheral circulation; pericarditis; myocarditis, inflammatory and auto-immune cardiomyopathies including myocardial sarcoid; ischaemic reperfusion injuries; endocarditis, valvulitis, and aortitis including infective (for example syphilitic); vasculitides; disorders of the proximal and peripheral veins including phlebitis and thrombosis, including deep vein thrombosis and complications of varicose veins;

14. oncology: treatment of common cancers including prostate, breast, king, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes; and, 15. gastrointestinal tract: Coeliac disease, proctitis, eosinopilic gastro-enteritis, mastocytosis, Crohn's disease, ulcerative colitis, microscopic colitis, indeterminant colitis, irritable bowel disorder, irritable bowel syndrome, non-inflammatory diarrhea, food-related allergies which have effects remote from the gut, e.g., migraine, rhinitis and eczema.

16. Diseases associated with raised levels of $PGD_2$ or its metabolites.

Thus, the present invention provides a compound of formula (I), or a pharmaceutically-acceptable salt or solvate thereof, as hereinbefore defined for use in therapy.

Preferably the compounds of the invention are used to treat diseases in which the chemokine receptor belongs to the CRTh2 receptor subfamily.

Particular conditions which can be treated with the compounds of the invention are asthma, rhinitis and other diseases in which raised levels of $PGD_2$ or its metabolites. It is preferred that the compounds of the invention are used to treat asthma.

In a further aspect, the present invention provides the use of a compound of formula (I), or a pharmaceutically acceptable salt or solvate thereof, as hereinbefore defined in the manufacture of a medicament for use in therapy.

In a further aspect, the present invention provides the use of a compound or formula (I), or a pharmaceutically acceptable salt or solvate thereof, as hereinbefore defined in the manufacture of a medicament for use in therapy in combination with drugs used to treat asthma and rhinitis (such as inhaled and oral steroids, inhaled β2-receptor agonists and oral leukotriene receptor antagonists).

The invention further relates to combination therapies wherein a compound of the invention, or a pharmaceutically acceptable salt thereof, or a pharmaceutical composition or formulation comprising a compound of the invention, is administered concurrently or sequentially or as a combined preparation with another therapeutic agent or agents, for the treatment of one or more of the conditions listed.

In particular, for the treatment of the inflammatory diseases such as (but not restricted to) rheumatoid arthritis, osteoarthritis, asthma, allergic rhinitis, chronic obstructive pulmonary disease (COPD), psoriasis, and inflammatory bowel disease, the compounds of the invention may be combined with agents listed below.

Non-steroidal anti-inflammatory agents (hereinafter NSAIDs) including non-selective cyclo-oxygenase COX-1/COX-2 inhibitors whether applied topically or systemically (such as piroxicam, diclofenac, propionic acids such as naproxen, flurbiprofen, fenoprofen, ketoprofen and ibuprofen, fenamates such as mefenamic acid, indomethacin, sulindac, azapropazone, pyrazolones such as phenylbutazone, salicylates such as aspirin); selective COX-2 inhibitors (such as meloxicam, celecoxib, rofecoxib, valdecoxib, hunarocoxib, parecoxib and etoricoxib); cyclo-oxygenase inhibiting nitric oxide donors (CINODs); glucocorticosteroids (whether administered by topical, oral, intramuscular, intravenous, or intra-articular routes); methotrexate; leflunomide; hydroxychloroquine; d-penicillamine; auranofin or other parenteral or oral gold preparations; analgesics; diacerein; intra-articular therapies such as hyaluronic acid derivatives; and nutritional supplements such as glucosamine.

The present invention still further relates to the combination of a compound of the invention, or a pharmaceutically acceptable salt thereof, together with a cytokine or agonist or antagonist of cytokine function, (including agents which act on cytokine signalling pathways such as modulators of the SOCS system) including alpha-, beta-, and gamma-interferons; insulin-like growth factor type I (IGF-1); interleukins (IL) including IL1 to 17, and interleukin antagonists or inhibitors such as anakinra; tumour necrosis factor alpha (TNF-α) inhibitors such as anti-TNF monoclonal antibodies (for example infliximab; adalimumab, and CDP-870) and TNF receptor antagonists including immunoglobulin molecules (such as etanercept) and low-molecular-weight agents such as pentoxyfylline.

In addition the invention relates to a combination of a compound of the invention, or a pharmaceutically acceptable salt thereof, with a monoclonal antibody targeting B-Lymphocytes (such as CD20 (rituximab), MRA-aIL16R and T-Lymphocytes, CTLA4-Ig, HuMax Il-15).

The present invention still further relates to the combination of a compound of the invention, or a pharmaceutically acceptable salt thereof, with a modulator of chemokine receptor function such as an antagonist of CCR1, CCR2, CCR2A, CCR2B, CCR3, CCR4, CCR5, CCR6, CCR7, CCR8, CCR9, CCR10 and CCR11 (for the C—C family); CXCR1, CXCR2, CXCR3, CXCR4 and CXCR5 (for the C—X—C family) and $CX_3CR1$ for the C—$X_3$—C family.

The present invention further relates to the combination of a compound of the invention, or a pharmaceutically acceptable salt thereof, with an inhibitor of matrix metalloprotease (MMPs), i.e., the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-11) and MMP-9 and MMP-12, including agents such as doxycycline.

The present invention still further relates to the combination of a compound of the invention, or a pharmaceutically acceptable salt thereof, and a leukotriene biosynthesis inhibitor, 5-lipoxygenase (5-LO) inhibitor or 5-lipoxygenase activating protein (FLAP) antagonist such as; zileuton; ABT-761; fenleuton; tepoxalin; Abbott-79175: Abbott-85761; a N-(5-substituted)-thiophene-2-alkylsulfonamide; 2,6-di-tert-butylphenolhydrazones; a methoxytetrahydropyrans such as Zeneca ZD-2138; the compound SB-210661; a pyridinyl-substituted 2-cyanonaphthalene compound such as L-739,010; a 2-cyanoquinoline compound such as L-746,530; or an indole or quinoline compound such as MK-591, MK-886, and BAY x 1005.

The present invention further relates to the combination of a compound of the invention, or a pharmaceutically acceptable salt thereof, and a receptor antagonist for leukotrienes (LT) B4, LTC4, LTD4, and LTE4. selected from the group consisting of the phenothiazin-3-1s such as L-651,392; amidino compounds such as CGS-25019c; benzoxalamines such as ontazolast; benzenecarboximidamides such as BEL 284/260; and compounds such as zafirlukast, ablukast, montelukast, pranlukast, verlukast (MK-679), RG-12525, Ro-245913, iralukast (CGP 45715A), and BAY x 7195.

The present invention still further relates to the combination of a compound of the invention, or a pharmaceutically acceptable salt thereof, and a phosphodiesterase (PDE) inhibitor such as a methylxanthanine including theophylline and aminophylline; a selective PDE isoenzyme inhibitor including a PDE4 inhibitor an inhibitor of the isoform PDE4D, or is an inhibitor of PDE5.

The present invention further relates to the combination of a compound of the invention, or a pharmaceutically acceptable salt thereof, and a histamine type 1 receptor antagonist such as cetirizine, loratadine, desloratadine, fexofenadine, acrivastine, terfenadine, astemizole, azelastine, levocabastine, chlorpheniramine, promethazine, cyclizine, or mizolastine; applied orally, topically or parenterally.

The present invention still further relates to the combination of a compound of the invention, or a pharmaceutically acceptable salt thereof, and a proton pump inhibitor (such as omeprazole) or a gastroprotective histamine type 2 receptor antagonist.

The present invention further relates to the combination of a compound of the invention, or a pharmaceutically acceptable salt thereof, and an antagonist of the histamine type 4 receptor.

The present invention still further relates to the combination of a compound of the invention, or a pharmaceutically acceptable salt thereof, and an alpha-1/alpha-2 adrenoceptor agonist vasoconstrictor sympathomimetic agent, such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride or ethylnorepinephrine hydrochloride.

The present invention further relates to the combination of a compound of the invention, or a pharmaceutically acceptable salt thereof, and an anticholinergic agents including muscarinic receptor (M1, M2, and M3) antagonist such as atropine, hyoscine, glycopyrrrolate, ipratropium bromide, tiotropium bromide, oxitropium bromide, pirenzepine or telenzepine.

The present invention still further relates to the combination of a compound of the invention, or a pharmaceutically acceptable salt thereof, and a beta-adrenoceptor agonist (including beta receptor subtypes 1-4) such as isoprenaline, salbutamol, formoterol, salmeterol, terbutaline, orciprenaline, bitolterol mesylate, or pirbuterol, or a chiral enantiomer thereof.

The present invention further relates to the combination of a compound of the invention, or a pharmaceutically acceptable salt thereof, and a chromone, such as sodium cromoglycate or nedocromil sodium.

The present invention still further relates to the combination of a compound of the is invention, or a pharmaceutically acceptable salt thereof, with a glucocorticoid, such as flunisolide, triamcinolone acetonide, beclomethasone dipropionate, budesonide, fluticasone propionate, ciclesonide or mometasone furoate.

The present invention further relates to the combination of a compound of the invention, or a pharmaceutically acceptable salt thereof, with an agent that modulates a nuclear hormone receptor such as PPARs.

The present invention still further relates to the combination of a compound of the invention, or a pharmaceutically acceptable salt thereof, together with an immunoglobulin (Ig) or Ig preparation or an antagonist or antibody modulating Ig function such as anti-IgE (for example omalizumab).

The present invention further relates to the combination of a compound of the invention, or a pharmaceutically acceptable salt thereof, and another systemic or topically-applied anti-inflammatory agent, such as thalidomide or a derivative thereof, a retinoid, dithranol or calcipotriol.

The present invention still further relates to the combination of a compound of the invention, or a pharmaceutically acceptable salt thereof, and combinations of aminosalicylates and sulfapyridine such as sulfasalazine, mesalazine, balsalazide, and olsalazine; and immunomodulatory agents such as the thiopurines, and corticosteroids such as budesonide.

The present invention further relates to the combination of a compound of the invention, or a pharmaceutically acceptable salt thereof, together with an antibacterial agent such as a penicillin derivative, a tetracycline, a macrolide, a beta-lactam, a fluoroquinolone, metronidazole, an inhaled aminoglycoside; an antiviral agent including acyclovir, famciclovir, valaciclovir, ganciclovir, cidofovir, amantadine, rimantadine, ribavirin, zanamavir and oseltamavir; a protease inhibitor such as indinavir, nelfinavir, ritonavir, and saquinavir; a nucleoside reverse transcriptase inhibitor such as didanosine, lamivudine, stavudine, zalcitabine or zidovudine; or a non-nucleoside reverse transcriptase inhibitor such as nevirapine or efavirenz.

The present invention still further relates to the combination of a compound of the invention, or a pharmaceutically acceptable salt thereof, and a cardiovascular agent such as a calcium channel blocker, a beta-adrenoceptor blocker, an angiotensin-converting enzyme (ACE) inhibitor, an angiotensin-2 receptor antagonist; a lipid lowering agent such as a statin or a fibrate; a modulator of blood cell morphology such as pentoxyfylline; thrombolytic, or an anticoagulant such as a platelet aggregation inhibitor.

The present invention further relates to the combination of a compound of the invention, or a pharmaceutically acceptable salt thereof, and a CNS agent such as an antidepressant (such as sertraline), an anti-Parkinsonian drug (such as deprenyl, L-dopa, ropinirole, pramipexole, a MAOB inhibitor such as selegine and rasagiline, a comP inhibitor such as tasmar, an A-2 inhibitor, a dopamine reuptake inhibitor, an NMDA antagonist, a nicotine agonist, a dopamine agonist or an inhibitor of neuronal nitric oxide synthase), or an anti-Alzheimer's drug such as donepezil, rivastigmine, tacrine, a COX-2 inhibitor, propentofylline or metrifonate.

The present invention still further relates to the combination of a compound of the invention, or a pharmaceutically acceptable salt thereof, and an agent for the treatment of acute or chronic pain, such as a centrally or peripherally-acting analgesic (for example an opioid or derivative thereof), carbamazepine, phenyloin, sodium valproate, amitryptiline or other anti-depressant agent-s, paracetamol, or a non-steroidal anti-inflammatory agent.

The present invention further relates to the combination of a compound of the invention, or a pharmaceutically acceptable salt thereof, together with a parenterally or topically-applied (including inhaled) local anaesthetic agent such as lignocaine or a derivative thereof.

A compound of the present invention, or a pharmaceutically acceptable salt thereof, can also be used in combination with an anti-osteoporosis agent including a hormonal agent such as raloxifene, or a biphosphonate such as alendronate.

The present invention still further relates to the combination of a compound of the invention, or a pharmaceutically acceptable salt thereof, together with a: (i) tryptase inhibitor; (ii) platelet activating factor (PAF) antagonist; (iii) interleukin converting enzyme (ICE) inhibitor; (iv) IMPDH inhibitor; (v) adhesion molecule inhibitors including VLA-4 antagonist; (vi) cathepsin; (vii) kinase inhibitor such as an inhibitor of tyrosine kinase (such as Btk, Itk, Jak3 or MAP, for example Gefitinib or Imatinib mesylate), a serine/threonine kinase (such as an inhibitor of a MAP kinase such as p38, JNK, protein kinase A, B or C, or IKK), or a kinase involved in cell cycle regulation (such as a cylin dependent kinase); (viii) glucose-6 phosphate dehydrogenase inhibitor; (ix) kinin-B.sub1.- or B.sub2.-receptor antagonist; (x) anti-gout agent, for example colchicine; (xi) xanthine oxidase inhibitor, for example allopurinol; (xii) uricosuric agent, for example probenecid, sulfinpyrazone or benzbromarone; (xiii) growth hormone secretagogue; (xiv) transforming growth factor (TGFβ); (xv) platelet-derived growth factor (PDGF); (xvi) fibroblast growth factor for example basic fibroblast growth factor (bFGF); (xvii) granulocyte macrophage colony stimulating factor (GM-CSF); (xviii) capsaicin cream; (xix) tachykinin NK.sub1. or NK.sub3. receptor antagonist such as NKP-608C, SB-233412 (talnetant) or D-4418; (xx) elastase inhibitor such as UT-77 or ZD-0892; (xxi) TNF-alpha converting enzyme inhibitor (TACE); (xxii) induced nitric oxide synthase (iNOS) inhibitor; (xxiii) chemoattractant receptor-homologous molecule expressed on TH2 cells, (such as a CRTH2 antagonist); (xxiv) inhibitor of P38; (xxv) agent modulating the function of Toll-like receptors (TLR), (xxvi) agent modulating the activity of purinergic receptors such as P2X7; or (xxvii) inhibitor of transcription factor activation such as NFkB, API, or STATS.

A compound of the invention, or a pharmaceutically acceptable salt thereof, can also be used in combination with an existing therapeutic agent for the treatment of cancer, for example suitable agents include:

(i) an antiproliferative/antineoplastic drug or a combination thereof, as used in medical oncology, such as an alkylating agent (for example cis-platin, carboplatin, cyclophosphamide, nitrogen mustard, melphalan, chlorambucil, busulphan or a nitrosourea); an antimetabolite (for example an antifolate such as a fluoropyrimidine like 5-fluorouracil or tegafur, raltitrexed, methotrexate, cytosine arabinoside, hydroxyurea, gemcitabine or paclitaxel); an antitumour antibiotic (for example an anthracycline such as adriamycin, bleomycin, doxorubicin, daunomycin, epirubicin, idarubicin, mitomycin-C, dactinomycin or mithramycin); an antimitotic agent (for example a vinca alkaloid such as vincristine, vinblastine, vindesine or vinorelbine, or a taxoid such as taxol or taxotere); or a topoisomerase inhibitor (for example an epipodophyllotoxin such as etoposide, teniposide, amsacrine, topotecan or a camptothecin);

(ii) a cytostatic agent such as an antioestrogen (for example tamoxifen, toremifene, raloxifene, droloxifene or iodoxyfene), an oestrogen receptor down regulator (for example fulvestrant), an antiandrogen (for example bicalutamide, flutamide, nilutamide or cyproterone acetate), a LHRH antagonist or LHRH agonist (for example goserelin, leuprorelin or buserelin), a progestogen (for example megestrol acetate), an aromatase inhibitor (for example as anastrozole, letrozole, vorazole or exemestane) or an inhibitor of 5α-reductase such as finasteride;

(iii) an agent which inhibits cancer cell invasion (for example a metalloproteinase inhibitor like marimastat or an inhibitor of urokinase plasminogen activator receptor function);

(iv) an inhibitor of growth factor function, for example: a growth factor antibody (for example the anti-erbb2 antibody trastuzumab, or the anti-erbb1 antibody cetuximab [C225]), a farnesyl transferase inhibitor, a tyrosine kinase inhibitor or a serine/threonine kinase inhibitor, an inhibitor of the epidermal growth factor family (for example an EGFR family tyrosine kinase inhibitor such as N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI-774) or 6-acrylamido-N-(3-chloro-4-fluorophenyl)-7-(3-molpholinopropoxy)quinazolin-4-amine (CI 1033)), an inhibitor of the platelet-derived growth factor family, or an inhibitor of the hepatocyte growth factor family;

(v) an antiangiogenic agent such as one which inhibits the effects of vascular endothelial growth factor (for example the anti-vascular endothelial cell growth factor antibody bevacizumab, a compound disclosed in WO 97/22596, WO 97/30035, WO 97/32856 or WO 98/13354), or a compound that works by another mechanism (for example linomide, an inhibitor of integrin αvβ3 function or an angiostatin);

(vi) a vascular damaging agent such as combretastatin A4, or a compound disclosed in WO 99/02166, WO 00/40529, WO 00/41669, WO 01/92224, WO 02/04434 or WO 02/08213;

(vii) an agent used in antisense therapy, for example one directed to one of the targets listed above, such as ISIS 2503, an anti-ras antisense;

(viii) an agent used in a gene therapy approach, for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; or (ix) an agent used in an immunotherapeutic approach, for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

In a still further aspect, the present invention provides the use of a compound of formula (I), or a pharmaceutically acceptable salt or solvate thereof, as hereinbefore defined in the manufacture of a medicament for the treatment of human diseases or conditions in which modulation of CRTh2 receptor activity is beneficial.

In the context of the present specification, the term "therapy" also includes "prophylaxis" unless there are specific indications to the contrary. The terms "therapeutic" and "therapeutically" should be construed accordingly.

The invention still further provides a method of treating diseases mediated by PGD2 or its metabolites wherein the prostanoid binds to its receptor (especially CRTh2) receptor, which comprises administering to a patient a therapeutically effective amount of a compound of formula (I), or a pharmaceutically acceptable salt, solvate or prodrug thereof, as hereinbefore defined.

The invention also provides a method of treating an inflammatory disease, especially psoriasis, in a patient suffering from, or at risk of, said disease, which comprises administering to the patient a therapeutically effective amount of a compound of formula (I), or a pharmaceutically acceptable salt or solvate thereof, as hereinbefore defined.

For the above-mentioned therapeutic uses the dosage administered will, of course, vary with the compound employed, the mode of administration, the treatment desired and the disorder indicated.

For the above-mentioned therapeutic uses the dosage administered will, of course, vary with the compound employed, the mode of administration, the treatment desired and the disorder indicated.

The compound of formula (I), prodrugs and pharmaceutically acceptable salts and solvates thereof may be used on their own but will generally be administered in the form of a pharmaceutical composition in which the formula (I) compound/salt/solvate (active ingredient) is in association with a pharmaceutically acceptable adjuvant, diluent or carrier. Depending on the mode of administration, the pharmaceutical composition will preferably comprise from 0.05 to 99% w (percent by weight), more preferably from 0.05 to 80% w, still to more preferably from 0.10 to 70% w, and even more preferably from 0.10 to 50% w, of active ingredient, all percentages by weight being based on total composition.

The present invention also provides a pharmaceutical composition comprising a compound of formula (I), or a pharmaceutically acceptable salt or solvate thereof, as herein before defined, in association with a pharmaceutically acceptable adjuvant, diluent or carrier.

The pharmaceutical compositions may be administered topically (e.g. to the lung and/or airways or to the skin) in the form of solutions, suspensions, heptafluoroalkane aerosols and dry powder formulations; or systemically, e.g. by oral administration in the form of tablets, capsules, syrups, powders or granules, or by parenteral administration in the form of solutions or suspensions, or by subcutaneous administration or by rectal administration in the form of suppositories or transdermally. Preferably the compound of the invention is administered orally.

The invention will now be illustrated by the following non-limiting examples in which, unless stated otherwise:

(i) when given, $^1$H NMR data is quoted in the form of delta values for major diagnostic protons, given in parts per million (ppm) relative to tetramethylsilane (TMS) as an internal standard;

(ii) mass spectra (MS): generally only ions which indicate the parent mass are reported, and unless otherwise stated the mass ion quoted is the positive mass ion—(M+H)$^+$;

(iii) the title compounds of the examples and methods were named using the ACD/name and ACD/name batch (version 6.0) from Advanced Chemical Development Inc, Canada;

(iv) unless stated otherwise, reverse phase HPLC was conducted using a Symmetry, NovaPak or Ex-Terra reverse phase silica column;

(v) solvents were dried with MgSO$_4$ or Na$_2$SO$_4$ (vi) the following abbreviations are used:

| | |
|---|---|
| EtOAc | Ethylacetate |
| Ether | diethyl ether |
| DCM | Dichloromethane |
| HCl | Hydrochloric acid |
| NaOH | Sodium hydroxide |
| NMP | N-methylpyrrolidine |
| DMF | N,N-dimethylformamide |
| THF | tetrahydrofuran |
| mcpba | 3-chloroperoxybenzoic acid (Aldrich 77% max) |
| | Pd(dppf)Cl$_2$ [1,1'-Bis(diphenylphosphino)ferrocene]dichloropalladium(II), complex with dichloromethane |
| RT | room temperature |

EXAMPLE 1

(2S)-2-[[4'-(methylsulfonyl)-3',5-bis(trifluoromethyl)
[1,1'-biphenyl]-2-yl]oxy]-propanoic acid

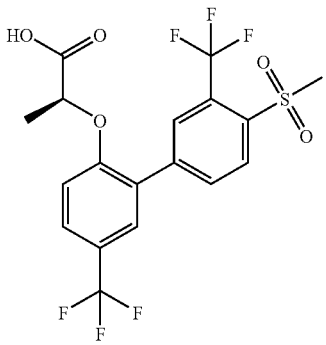

a) 4-bromo-1-(methylthio)-2-(trifluoromethyl)-benzene

A mixture of sodium thiomethoxide (317 mg) and 5-bromo-2-fluorobenzotrifluoride (1.0 g) in DMF (4 ml) was heated at 50° C. for 1 h then poured into water and extracted with isohexane. The organics were washed with brine, dried and concentrated in vacuo to give the tip sub-title compound (762 mg).

$^1$H NMR DMSO-d6: δ 7.74 (1H, d) 7.59 (1H, dd); 7.22 (1H, d); 2.51 (3H, s)

b) [4-(methylthio)-3-(trifluoromethyl)phenyl]-boronic acid n-BuLi (2.7 ml, 2.5M in hexane) was added dropwise to the product of step a) and tri-isopropyl borate (1.6 ml) in THF at −78° C. Stirred for 5 min, then quenched with 2M HCl (50 ml) and extracted with diethyl ether (50 ml). The organic layer was washed with water, brine, dried (Na$_2$SO$_4$) and evaporated in vacuo. The resulting solid was triturated with isohexane (100 ml), filtered and dried to give the product (0.83 g). NMR indicated a 2:1 mixture of product, monomer and trimer of boronic acid.

$^1$H NMR CDCl$_3$: δ 8.03 (1H, d), 7.51 (1H, dd), 6.7 (1H, d), 4.71 (1H, q), 1.69 (3H, d) and 1.43 (9H, s).

c) 4,4,5,5-tetramethyl-2-[4-(methylthio)-3-(trifluoromethyl)phenyl]-1,3,2-dioxaborolane The product of step b) (0.25 g) was heated in dioxan (2 ml) with pinacol (2 equiv) for 3 h. The solution was treated with diethyl ether and water. The organic layer was separated, washed with brine, dried (Na$_2$SO$_4$) and concentrated in vacuo. Yield 85 mg.

$^1$H NMR CDCl$_3$: δ 8.03 (1H, d), 7.86 (1H, d), 7.31 (1H, d), 2.53 (3H, s) and 1.35 (12H, s).

d) 2-iodo-4-(trifluoromethyl)-phenol 4-(trifluoromethyl)-phenol (8 g) in anhydrous DMF (80 ml) was cooled to 0° C. NaI (9.06 g) and chloroamine-T (16.1 g) was added portionwise and stirred at room temperature overnight. Then diluted with 2M HCl and extracted with ethylacetate. The organic phase was washed with sodium thiosulfate solution, dried (MgSO$_4$) and concentrated in vacuo. The residue was purified by chromatography (silica, eluting with isohexane:ethyl acetate) to give the sub-title compound as a yellow oil (13 g).

MS: APCI (−ve): 287 (M−H)

e) 1,1-Dimethylethyl (2S)-2-[2-iodo-4-(trifluoromethyl)phenoxy]propanoate

DIAD (2.9 ml) was added to the product of step e) (3.5 g), triphenyl phosphine (3.87 g) and tert-butyl (R)-(+) lactate (1.96 g) in THF (35 ml) at 0° C. and stirred for 18 h. The solvent was evaporated in vacuo and the residue purified by flash column chromatography eluting with petroleum ether:dichloromethane (4:1) to give the product as a colourless oil. Yield**

$^1$H NMR CDCl$_3$: δ 8.03 (1H, d), 7.51 (1H, dd), 6.7 (1H, d), 4.71 (1H, q), 1.69 (3H, d) and 1.43 (9H, s).

f) 1,1-Dimethylethyl (2S)-2-[[4'-(methylthio)-3',5-bis(trifluoromethyl)[1,1'-biphenyl]-2-yl]oxy propanoate The products of step e) (0.3 g), the product of step c) (230 mg), sodium carbonate (170 mg), Pd(dppf)Cl$_2$ (50 mg), dioxan (10 ml) and methanol (1 ml) were heated at 90° C. for 24 h, then concentrated in vacuo. The residue was purified by flash column chromatography eluting with ethyl acetate:isohexane (2:8) to give the product (0.35 g), which was used directly without further characterisation.

g) (2S)-2-[[4'-(methylthio)-3',5-bis(trifluoromethyl) [1,1'-biphenyl]-2-yl]oxy]-propanoic acid The product of step f) (0.34 g) in dichloromethane (6 ml) and TFA (3 ml) was stirred for 2 h at room temperature, then concentrated in vacuo. The residue was diluted with dichloromethane, washed with water, dried (MgSO$_4$) then concentrated in vacuo. The residue was then dissolved in acetonitrile (10 ml) and water (10 ml) and treated with oxone (0.6 g).

The reaction mixture was stirred for 2 h, further oxone (0.6 g) was added and the reaction stirred for 2 days. The solution was washed with dichloromethane (×3). The combined extracts were dried (MgSO$_4$) then concentrated in vacuo. Further purified by reverse phase HPLC, then trituration with dichloromethane and isohexane to give the title compound as a white solid (100 mg).

MS: APCI (−ve): 455 (M−H)

$^1$H NMR DMSO-D6: δ 8.49 (1H, s), 8.31 (1H, d), 8.12 (1H, d), 7.84-7.76 (2H, m), 7.23 (1H, d), 5.13 (1H, q) and 1.46 (3H, d).

EXAMPLE 2

[[3',5-Dichloro-4-(methylsulfonyl)[1,1'-biphenyl]-2-yl]oxy]acetic Acid

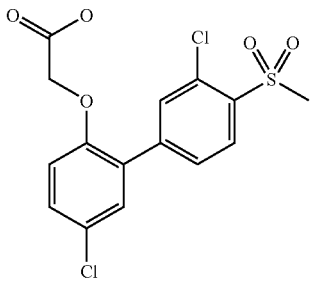

a) 1,1-Dimethylethyl (4-chloro-2-iodophenoxy)acetate

A mixture of 5-chloro-2-iodophenol (4.75 g), 1,1-dimethylethyl bromoacetate (3.05 ml) and potassium carbonate (2.58 g) in acetonitrile (20 ml) was heated under reflux for 2 h. Water was added and the mixture was extracted with ether (three times). The organic extracts were dried (MgSO$_4$), evaporated and purified by chromatography (silica, petrol—ether as eluent) to give the sub-title compound (6.88 g).

$^1$H NMR CDCl$_3$: δ 7.77 (1H, d), 7.45 (1H, dd), 6.61 (1H, d), 4.55 (2H, s), 1.48 (9H, s).

b) 4-Bromo-2-chloro-1-(methylthio)benzene

A mixture of 4-bromo-2-chloro-1-fluorobenzene (8.04 g) and sodium methylthiolate (3.05 g) in DMF (25 ml) was heated at 50° C. for 2.5 h. Water was added and the mixture was extracted with ether (three times). The organic extracts were washed with water (twice), dried (MgSO$_4$), and evaporated to give the sub-title compound (8.93 g).

$^1$H NMR CDCl$_3$: δ 7.54 (1H, d), 7.34 (1H, dd), 7.02 (1H, dd), 2.47 (3H, s).

c) [3-Chloro-4-(methylthio)phenyl]boronic acid

Butyl lithium (15 ml, 1.9M in hexanes) was added over 40 min to a solution of the product from step b) (6.82 g) and triisopropylborate (8.0 ml) in THF (30 ml) at −78° C. and stirred for a further 1 h. 2M HCl (20 ml) was added, the mixture was warmed to 20° C. and extracted with ether (three times). The organic extracts were dried (MgSO$_4$), evaporated and purified by chromatography (silica, petrol—ether as eluent) to give the sub-title compound (1.82 g).

MS: ESI (−ve): 201 [M−H]$^-$ 100% d) 1,1-Dimethylethyl [[3',5-dichloro-4'-(methylsulfonyl)[1,1'-biphenyl]-2-yl]oxy]acetate A mixture of the product of step a) (390 mg) and the product of step c) (239 mg), sodium carbonate (220 mg) and Pd(dppf)Cl$_2$ (74 mg) in dioxan (5 ml) and methanol (3 ml) was heated at 100° C. for 24 h, then concentrated in vacuo and dissolved in acetone (10 ml). A solution of oxone (2.0 g) in water and aq K$_2$CO$_3$ (to keep the mixture at ca. pH 8) were added and stirred for 2 days. The mixture was extracted with ether (three times) and the organic extracts were dried (MgSO$_4$), evaporated and purified by chromatography (silica, petrol—ether as eluent) to give the sub-title compound (73 mg).

$^1$H NMR CDCl$_3$: δ 8.18 (1H, d), 7.80 (1H, d), 7.70 (1H, dd), 7.34-7.31 (2H, m), 6.79 (1H, d), 4.54 (2H, s), 3.30 (3H, s), 1.47 (9H, s).

Further elution with ether gave 1,1-dimethylethyl [[3',5-dichloro-4'-(methylsulfinyl)[1,1'-biphenyl]-2-yl]oxy]acetate (35 mg)

$^1$H NMR CDCl$_3$: δ 7.99 (1H, d), 7.82 (1H, d), 7.66 (1H, dd), 7.35-7.28 (2H, m), 6.79 (1H, d), 4.53 (2H, s), 2.87 (2H, s), 1.47 (9H, s).

e) [[3',5-Dichloro-4'-(methylsulfonyl)[1,1'-biphenyl]-2-yl]oxy]acetic acid

A solution of the product from step d) (73 mg) in TFA (3 ml) was stirred for 2 h. The solvent was removed in vacuo, water was added and the mixture was extracted with dichloromethane (three times). The organic extracts were dried (MgSO$_4$), evaporated and triturated with ether to give the title compound (46 mg) as a white solid. M.p. 140-2° C.

MS: ESI (+ve): 393 [M+NH$_4$]$^+$ 100%

$^1$H NMR DMSO-d6: δ 8.06 (1H, d), 8.02 (1H, d), 7.83 (1H, dd), 7.51 (1H, d), 7.46 (1H, dd), 7.13 (1H, d), 4.81 (3H, s), 3.41 (3H, s).

EXAMPLE 3

[[3',5-Dichloro-4'-(methylsulfinyl)[1,1'-biphenyl]-2-yl]oxy]acetic acid

A solution of the more polar product from Example 2 step d) (35 mg) in TFA (2 ml) was stirred for 24 h. The solvent was removed in vacuo, the mixture was azeotroped with toluene and purified by chromatography (silica, CH$_2$Cl$_2$-MeOH—AcOH as eluent) to give the title compound (22 mg) as a white solid.

MS: ESI (+ve): 359 [M+H]$^+$ 100%

$^1$H NMR DMSO-d6: δ 7.86 (3H, s), 7.47 (1H, d), 7.43 (1H, dd), 7.11 (1H, d), 4.80 (2H, s), to 2.85 (3H, s).

EXAMPLE 4

(2S)-2-[[3',5-Dichloro-4'-(methylsulfonyl)[1,1'-biphenyl]-2-yl]oxy]propanoic acid

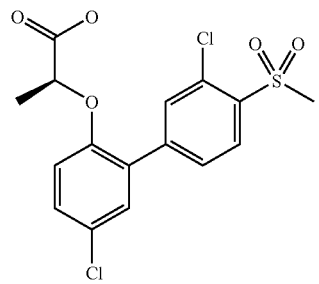

a) 1,1-Dimethylethyl (2S)-2-(4-chloro-2-iodophenoxy)propanoate

DIAD (1.64 ml) was added to a solution of 5-chloro-2-iodophenol 1.76 g), triphenyl phosphine (2.17 g) and tert butyl (R) lactate (1.02 g) in THF (8 ml) at 0° C. and stirred at 20° C. for 18 h. The solvent was removed in vacuo and the residue purified by (silica, petrol—ether as eluent) to give the sub-title compound (2.01 g).

$^1$H NMR CDCl$_3$: δ 7.76 (1H, d), 7.21 (1H, dd), 6.61 (1H, d), 4.61 (1H, q), 1.65 (3H, d), 1.42 (9H, s).

b) 1,1-Dimethylethyl (2S)-2-[[3',5-dichloro-4'-(methylsulfonyl)[1,1'-biphenyl]-2-yl]oxy]propanoate A mixture of the product of step a) (412 mg) and the product of Example 2 step c) (246 mg), palladium acetate (22 mg), trisorthotoluenephosphine (49 mg) and sodium carbonate (220 mg) in dioxane (5 ml) and methanol (3 ml) was heated at 100° C. for 12 h, then concentrated in vacuo and dissolved in acetone (10 ml). A solution of oxone (2.0 g) in water and aq K$_2$CO$_3$ (to keep the mixture at ca. pH 8) were added and stirred for 2 days. The mixture was extracted with ether (three times) and the organic extracts were dried (MgSO$_4$), evaporated and purified by chromatography (silica, petrol—ether as eluent) to give the sub-title compound (319 mg).

$^1$H NMR CDCl$_3$: δ 8.17 (1H, d), 7.86 (1H, d), 7.71 (1H, dd), 7.32-7.27 (2H, m), 6.78 (1H, d), 4.67 (1H, q), 3.31 (3H, s), 1.52 (3H, d), 1.44 (9H, s).

c) (2S)-2-[[3',5-Dichloro-4'-(methylsulfonyl)[1,1'-biphenyl]-2-yl]oxy]propanoic acid The title compound was prepared by the method of Example 2 step e) using the to product of step b).

MS: EST (+ve): 407 [M+NH$_4$]$^+$ 100%

$^1$H NMR. DMSO-d6: δ 13.23 (1H, s), 8.07 (1H, d), 8.06 (1H, s), 7.87 (1H, dd), 7.52 (1H, d), 7.45 (1H, dd), 7.06 (1H, d), 5.03 (1H, q), 3.41 (3H, s), 1.46 (3H, d).

EXAMPLE 5

(2S)-2-[4-chloro-2-[2,5-difluoro-4-(4-morpholinylsulfonyl)phenoxy]phenoxy]-propanoic acid

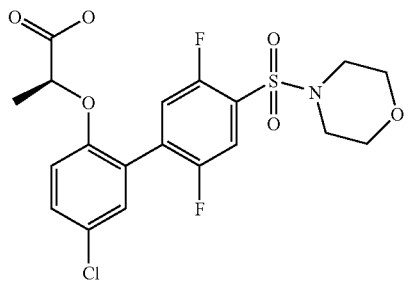

a) 4-[(4-bromo-2,5-difluorophenyl)sulfonyl]-morpholine

Morpholine (0.16 ml) was added to a stirred solution of 4-bromo-2,5-difluoro-benzenesulfonyl chloride (0.18 g) in dichloromethane (6 ml) under nitrogen. The reaction mixture was stirred overnight and then quenched with water. The organic phase was dried (MgSO$_4$) and concentrated in vacuo to give the sub-title compound as a white solid (200 mg).

$^1$H NMR CDCl$_3$: δ 7.62 (1H, dd), 7.52 (1H, dd), 3.77-3.7 (4H, m) and 3.23-3.2 (4H, m).

b) Benzyl 2-bromo-4-chlorophenyl ether

Benzyl bromide (13.1 ml) was added to a stirred mixture of 2-bromo-4-chlorophenol (20.7 g) and potassium carbonate (27.6 g) in DMF (200 ml). After 72 h, the mixture was partitioned between diethylether and water, the organic layer washed with water, dried and the solvent evaporated under reduced pressure. The residue was purified by chromatography (silica, EtOAc/isohexane as eluent). to give the sub-title compound (18.1 g).

$^1$H NMR CDCl$_3$: δ 7.55 (1H, s); 7.46-7.18 (6H, m); 6.84 (1H, d); 5.14 (2H, s)

c) [2-(Benzyloxy)-5-chlorophenyl]boronic acid

A solution of butyl lithium (1.6 M in hexane) (50 ml) was added dropwise to a stirred solution of the product from step a) (23 g) in diethylether (300 ml) at −70° C. After 1 h a further 18 ml of butyl lithium was added, left for 0.75 h, then trimethylborate (10 ml) added and the mixture warmed to RT and left for 16 h. 2 M Hydrochloric acid (100 ml) was added, stirred for 1 h then the organic layer separated and extracted with aqueous sodium hydroxide solution. The basic layer was acidified with 2 M hydrochloric acid solution, extracted with diethylether which was dried and evaporated under reduced pressure. The residue was triturated with iso-hexane and filtered to give the sub-title compound (10.8 g)

$^1$H NMR CDCl$_3$: δ 7.82 (1H, d); 7.44-7.34 (6H, m); 6.90 (1H, d); 5.99 (2H, s); 5.12 (2H, s)

d) 2-[5-Chloro-2-(phenylmethoxy)phenyl]-4,4,5,5-tetramethyl-1,3,2-dioxaboralane The sub-title compound was prepared from the product of step b) (5 g), pinacol (2.7 g) in anhydrous diethyl ether (200 ml). The reagents were stirred under nitrogen overnight. A further 1.2 g of pinacol and molecular serves were added and stirred overnight. The reaction mixture was washed with water, dried (MgSO$_4$) and concentrated in vacuo to give the sub-title compound (5.6 g).

$^1$H NMR DMSO-d6: δ 7.27-7.64 (m, 7H), 6.85 (d, 1H), 5.09 (s, 2H), 1.36 (s, 12H)

e) 4-Chloro-2-(4,4,5,5-tetramethyl-1,3,2-dioxaborolan-2-yl)phenol

The product from step d) was dissolved in ethanol (100 ml) and treated with palladium on activated carbon (5%), the suspension was stirred for 30 min under hydrogen (1 bar). The mixture was then filtered, and the filtrate was concentrated in vacuo to give the subtitle compound (4.2 g).

$^1$H NMR DMSO-d6: δ 7.76-7.79 (s, 1H), 6.79-7.62 (m, 3H), 1.36 (s, 12H)

f) 1,1-Dimethylethyl 2-[4-Chloro-2-(4,4,5,5-tetramethyl-1,3,2-dioxaborolan-2-yl)phenoxy]-(2S)-propanoate The subtitle compound was prepared by the method of Example 2 step a) using the product from step e) and tert-butyl (R)-(+) lactate.

g) 2-(2-Borono-4-chlorophenoxy)-(2S)-propanoic acid

The subtitle compound was prepared by the method of Example 4 step a) using the product from step (f). Yield 2.5 g. The crude material was carried forward to step h).

h) (2S)-2-[4-chloro-2-[2,5-difluoro-4-(4-morpholinylsulfonyl)phenoxy]phenoxy]-propanoic acid The product of step g) (0.1 g), the product of step a) (0.15 g), tetrakis palladiumtriphenylphosphine (O), sodium carbonate (2M solution, 4 ml), ethanol (4 ml) and toluene (8 ml) were heated at 90° C. for 18 h. The reaction mixture was cooled to room temperature, then concentrated in vacuo and further purified by reverse phase HPLC to give the title compound (0.1 g).

$^1$H NMR DMSO-d6: δ 8.17-8.15 (1H, m), 7.63 (1H, t), 7.4 (2H, s), 7.0 (1H, s), 4.56 (1H, d), 3.6 (4H, m), 3.11 (4H, s) and 1.3 (3H, d).

EXAMPLE 6

[[3'-Fluoro-4'-[(1-methylethyl)sulfonyl]-5-(trifluoromethyl)[1,1'-biphenyl]-2-yl]oxy]acetic acid

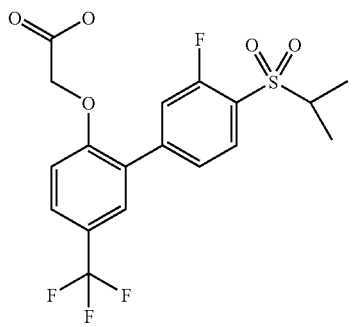

a) 4-Bromo-2-fluorobenzenethiol

Triphenylphosphine was added portionwise to a solution of 4-bromo-2-fluorobenzenesulfonyl chloride (8.44 g) in THF (30 ml) at 0° C. After 15 min water was added and the colourless solution was stirred at 20° C. for 18 h. The solvent was removed in vacuo, the residues dissolved in DCM and extracted with 2M sodium hydroxide (twice). The aqueous layers were washed with DCM, combined, acidified (4M HCl) and extracted with ethyl acetate (thrice). These organic extracts were dried (MgSO$_4$) and evaporated to give the sub-title compound (5.89 g).

MS: ESI (−ve): 206 [M−H]$^−$ 94% b) 4-Bromo-2-fluoro-[(1-methylethyl)thio]benzene

A mixture of the product from step a) (2.77 g), isopropyliodide (1.7 ml) and K$_2$CO$_3$ (2.0 g) in acetone (10 ml) was stirred for 3 h. Water was added and the mixture was extracted with ether (three times). The organic extracts were dried (MgSO$_4$) and, evaporated and to give the sub-title compound (3.22 g).

$^1$H NMR CDCl$_3$: δ 7.44-7.21 (3H, m), 3.41 (1H, heptet), 1.27 (6H, d).

c) [3-Fluoro-4-[(1-methylethyl)thio]phenyl]boronic acid

The sub-title compound was prepared by the method of Example 2 step c) using the product of step b).

MS: ESI (−ve): 213 [M−H]$^−$ 100% d) Methyl [2-bromo-4-(trifluoromethyl)phenoxy]acetate

The sub-title compound was prepared by the method of Example 2 step a) using methyl bromoacetate and 2-bromo-4-(trifluoromethyl)phenol.

$^1$H NMR CDCl$_3$: δ 7.82 (1H, d), 7.48 (1H, dd), 6.81 (1H, d), 3.77 (3H, s).

e) Methyl [[3'-fluoro-4'-[(1-methylethyl)sulfonyl]-5-(trifluoromethyl)[1,1'-biphenyl]-2-yl]oxy]acetate The sub-title compound was prepared by the method of Example 2 step d) using the products of step c) and step d).

MS: ESI (+ve): 452 [M+NH$_4$]$^+$ 100% f) [[3'-Fluoro-4'-[(1-methylethyl)sulfonyl]-5-(trifluoromethyl)[1,1'-biphenyl]-2-yl]oxy]acetic acid A solution of the product from step e) (140 mg) in NaOH (0.35 ml, 1 M), THY (2 ml) and MeOH (1 ml) was stirred for 2 h. The solvent was removed in vacuo and the residue was washed with ether, acidified (2M HCl) and extracted with DCM (thrice). The organic extracts were dried (MgSO$_4$), evaporated and crystallised from isohexane—DCM to give the title compound (105 mg). M.p. 170-1° C.

MS: ESI (+ve): 438 [M+NH$_4$]$^+$ 100%

$^1$H NMR DMSO-d6: δ 13.22 (1H, s), 7.90-7.78 (4H, m), 7.74 (1H, dd), 7.30 (1H, d), 4.92 (2H, s), 3.54 (1H, heptet), 1.25 (6H, d).

EXAMPLE 7

[[5-Chloro-4'-(methylsulfonyl)-3'-(trifluoromethyl)[1,1'-biphenyl]-2-yl]oxy]-acetic acid

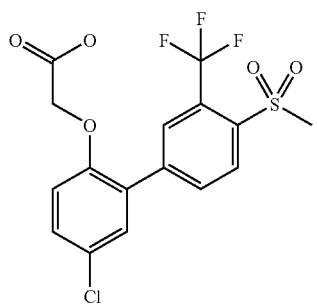

a) Methyl (4-chloro-2-iodophenoxy)acetate

A mixture of 5-chloro-2-iodophenol (4.95 g), methyl bromoacetate (1.85 ml) and potassium carbonate (2.79 g) in acetonitrile (20 ml) was heated under reflux for 2 h. Aq HCl was added and the mixture was extracted with ether (three times). The organic extracts were dried (MgSO$_4$), evaporated and purified by chromatography (silica, petrol—ether as eluent) to give the sub-title compound (5.75 g).

$^1$H NMR CDCl$_3$: δ 7.77 (1H, d), 7.25 (1H, dd), 6.64 (1H, d), 4.68 (2H, s), 3.81 (3H, s).

b) Methyl [[5-chloro-4'-(methylsulfonyl)-3'-(trifluoromethyl)[1,1'-biphenyl]-2-yl]oxy]-acetate The sub-title compound was prepared by the method of Example 2 step d) using the products from step a) and Example 1 step b).
$^1$H NMR DMSO-d6: δ 11.69 (1H, s), 8.30-8.27 (2H, m), 8.15 (1H, d), 7.58 (1H, d), 7.50 (1H, dd), 7.19 (1H, d), 4.82 (3H, s).

c) [[5-Chloro-4'-(methylsulfonyl)-3'-(trifluoromethyl)[1,1'-biphenyl]-2-yl]oxy]-acetic acid The sub-title compound was prepared by the method of Example 6 step f) using the product from step b).
MS: EPCI (+ve): 407 [M+NH$_4$]$^+$ 100%
$^1$H NMR DMSO-d6: δ 11.69 (1H, s), 8.33 (1H, d), 8.26 (1H, d), 8.15 (1H, dd), 7.57 (1H, d), 7.48 (1H, dd), 7.17 (1H, d), 4.82 (2H, s), 3.33 (3H, s).

EXAMPLE 8

[[5-Fluoro-4'-(methylsulfonyl)-3'-(trifluoromethyl)[1,1'-biphenyl]-2-yl]oxy]-acetic acid

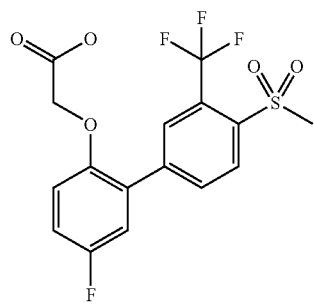

a) Ethyl (2-bromo-4-fluorophenoxy)acetate

The sub-title compound was prepared by the method of Example 2 step a) using 2-bromo-4-fluorophenol and ethyl bromoacetate.
MS: ESI (+ve): 277 [M+H]$^+$ 100% b) Ethyl [[5-fluoro-4'-(methylsulfonyl)-3'-(trifluoromethyl)[1,1'-biphenyl]-2-yl]oxy]-acetate The sub-title compound was prepared by the method of Example 2 step d) (but in dioxane-ethanol) using the products from step a) and Example 1 step b).
$^1$H NMR CDCl$_3$: δ 8.35 (1H, d), 8.17 (1H, d), 8.01 (1H, dd), 7.14-7.06 (2H, m), 6.90-6.64 (1H, d), 4.63 (2H, s), 4.25 (2H, q), 3.23 (2H, s), 1.28 (3H, t).

c) [[5-Fluoro-4'-(methylsulfonyl)-3'-(trifluoromethyl)[1,1'-biphenyl]-2-yl]oxy]acetic acid The title compound was prepared by the method of Example 6 step f) using the product from step b).
MS: EPCI (+ve): 407 [M+NH$_4$]$^+$ 100%
$^1$H NMR DMSO-d6: δ 8.35 (1H, d), 8.27 (1H, d), 8.17 (1H, dd), 7.40 (1H, dd), 7.28 (1H, d), 7.16 (1H, dd), 4.79 (2H, s), 3.32 (3H, s).

EXAMPLE 9

[[4'-(Ethylsulfonyl)-3',5-bis(trifluoromethyl)[1,1'-biphenyl]-2-yl]oxy]acetic acid

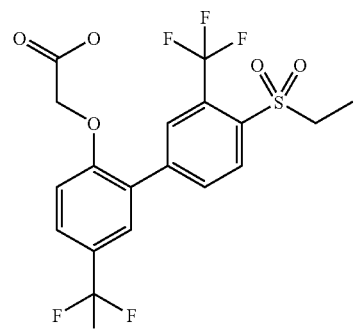

a) 4-Bromo-1-(ethylthio)-2-(trifluoromethyl)benzene

The sub-title compound was prepared by the method of Example 2 step b) using sodium ethylthiolate and 4-bromo-1-fluoro-2-(trifluoromethyl)benzene.
$^1$H NMR CDCl$_3$: δ 7.76 (1H, d), 7.58 (1H, dd), 7.32 (1H, d), 2.96 (2H, q), 1.31 (3H, t).

b) 1-(Ethylthio)-2-(trifluoromethyl))phenyl]boronic acid

The sub-title compound was prepared by the method of Example 2 step c) using the product from step a)
MS: ESI (−ve): 213 [M−H]$^-$ 100% c) Methyl [2-bromo-4-(trifluoromethyl)phenoxy]acetate

The sub-title compound was prepared by the method of Example 2 step a) using methyl bromoacetate and 2-bromo-4-(trifluoromethyl)phenol.
$^1$H NMR CDCl$_3$: δ 7.82 (1H, d), 7.48 (1H, dd), 6.81 (1H, d), 3.77 (3H, s).

d) Methyl [[4'-(ethylsulfonyl)-3',5-bis(trifluoromethyl)[1,1'-biphenyl]-2-yl]oxy]acetate The sub-title compound was prepared by the method of Example 2 step d) using the products from steps b) and c).
MS: APCI (−ve): 469 [M−H]$^-$ 100% e) [[4'-(Ethylsulfonyl)-3',5-bis(trifluoromethyl)[1,1'-biphenyl]-2-yl]oxy]acetic acid The title compound was prepared by the method of Example 5 step f) using the product from step d). M.p. 174-5° C.
MS: ESI (−ve): 455 [M−H]$^-$ 100%

¹H NMR DMSO-d6: δ 8.38 (1H, d), 8.24 (1H, d), 8.18 (1H, dd), 7.84-7.80 (2H, m), 7.33 (1H, d), 4.91 (2H, s), 3.41 (2H, q), 1.21 (3H, t).

EXAMPLE 10

(2S)-2-[[4'-(Ethylsulfonyl)-3',5-bis(trifluoromethyl)[1,1'-biphenyl]-2-yl]oxy]propanoic acid

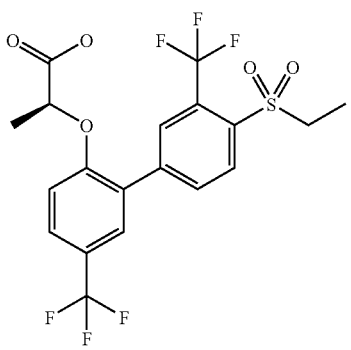

a) 1,1-Dimethylethyl (2S)-2-[[4'-(ethylsulfonyl)-3',5-bis(trifluoromethyl)[1,1'-biphenyl]-2-yl]oxy]propanoate The sub-title compound was prepared by the method of Example 2 step d) using the products from step b) and Example 1 step b).
MS: APCI (−ve): 525 [M−H]⁻ 100% b) (2S)-2-[[4'-(Ethylsulfonyl)-3',5-bis(trifluoromethyl)[1,1'-biphenyl]-2-yl]oxy]propanoic acid The sub-title compound was prepared by the method of Example 2 step e) using the product from step a). M.p. 124-6° C.
MS: ESI (−ve): 469 [M−H]⁻ 100%
¹H NMR DMSO-d6: δ 8.47 (1H, d), 8.26-8.19 (2H, m), 8.18 (1H, dd), 7.82 (1H, dd), 7.25 (1H, d), 5.20 (1H, q), 3.41 (2H, q), 1.48 (3H, d), 1.21 (3H, t).

EXAMPLE 11

5-Chloro-4'-4-morpholinylsulfonyl)-3'-trifluoromethyl)[1,1'-biphenyl]-2-yl]oxy]acetic acid

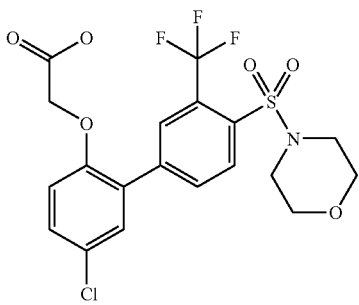

a) 4-[[4-Bromo-2-(trifluoromethyl)phenyl]sulfonyl]morpholine

Morpholine (1.1 ml) was added to a solution of [4-bromo-2-(trifluoromethyl)phenyl]sulfonyl chloride (2.03 g) in DCM (7 ml) at 0° C. and stirred at 20° C. for 16 h. Water was added and the mixture was extracted with DCM. The organic extracts were dried (MgSO₄), evaporated and purified by chromatography (silica, petrol—ether as to eluent) to give the sub-title compound 2.10 g).
¹H NMR CDCl₃: δ 8.04 (1H, d), 7.97 (1H, d), 7.85 (1H, dd), 3.73 (4H, t), 3.23 (4H, t).

b) 4-[[5'-Chloro-2'-(phenylmethoxy)-3-(trifluoromethyl)[1,1'-biphenyl]-4-yl]sulfonyl-morpholine A mixture of the product of step a) (450 mg) and [5-chloro-2-(phenylmethoxy)phenyl]boronic acid (351 mg), sodium carbonate (277 mg) and Pd(dppf)Cl₂ (93 mg) in dioxan (3 ml) and methanol (0.5 ml) was heated at 85° C. for 16 h. Water was added and the mixture was extracted with ether (three times), the organic extracts were dried (MgSO₄), evaporated and purified by chromatography (silica, petrol—ether as eluent) to give the sub-title compound (538 mg).
M.p. 118-9° C.
¹H NMR CDCl₃: δ 8.13-8.04 (2H, m), 7.83 (1H, dd), 7.37-7.26 (7H, m), 7.04 (1H, d), 5.09 (2H, s), 3.74 (4H, t), 3.25 (4H, t).

c) 4-[[5'-Chloro-2'-hydroxy-3-(trifluoromethyl)[1,1'-biphenyl]-4-yl]sulfonyl]morpholine Boron tribromide (2.5 ml, 1.0 M in DCM) was added to a solution of the product from step b) (1.16 g) in DCM (15 ml) at 0° C. The solution was stirred for 15 min then quenched with water. The mixture was extracted with DCM (three times), the organic extracts were dried (MgSO₄), evaporated and purified by chromatography (silica, petrol—ether as eluent) to give the sub-title compound (851 mg).
MS: ESI (−ve): 420 [M−H]⁻ 100% d) Ethyl [[5-chloro-4'-(4-morpholinylsulfonyl)-3'-(trifluoromethyl)[1,1'-biphenyl]-2-yl]oxy]acetate The sub-title compound was prepared by the method of Example 2 step a) using the product from steps c) and ethyl bromoacetate.
MS: ESI (+ve): 508 [M+H]⁺ 100% e) [[5-Chloro-4'-(4-morpholinylsulfonyl)-3'-(trifluoromethyl)[1,1'-biphenyl]-2-yl]oxy]acetic acid The sub-title compound was prepared by the method of Example 5 step f) using the product from step d). M.p. 208-9° C.
MS: ESI (−ve): 478 [M−H]⁻ 100%

¹H NMR DMSO-d6: δ 8.31 (1H, d), 8.11 (2H, d), 7.56 (1H, d), 7.41 (1H, dd), 7.16 (1H, d), 4.80 (2H, s), 3.66 (4H, t), 3.19 (4H, t).

EXAMPLE 12

(2S)-2-[[5-Chloro-4'-(4-morpholinylsulfonyl)-3'-(trifluoromethyl)[1,1'-biphenyl]-2-yl]oxy]propanoic acid

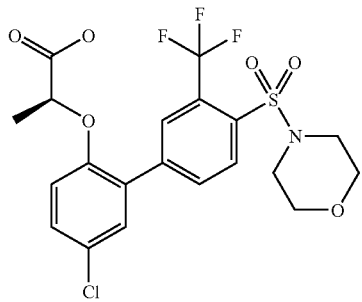

a) 1,1-Dimethylethyl (2S)-2-[[5-chloro-4'-(4-morpholinylsulfonyl)-3'-(trifluoromethyl)[1,1'-biphenyl]-2-yl]oxy]propanoate The sub-title compound was prepared by the method of Example 4 step a) using the product from Example 11 step c).
¹H NMR CDCl₃: δ 8.27 (1H, d), 8.14 (1H, d), 7.93 (1H, dd), 7.35 (1H, d), 7.30 (1H, dd), 6.80 (1H, d), 4.70 (1H, q), 3.76 (4H, t), 3.28 (4H, t), 1.52 (3H, d), 1.42 (9H, s).

b) (2S)-2-[[5-Chloro-4'-(4-morpholinylsulfonyl)-3'-(trifluoromethyl)[1,1'-biphenyl]-2-yl]oxy]propanoic acid The sub-title compound was prepared by the method of Example 2 step e) using the product from step a). M.p. 148-9° C.
MS: ESI (−ve): 492 [M−H]⁻ 100%
¹H NMR DMSO-d6: δ 13.26 (1H, s), 8.44 (1H, d), 8.12 (2H, s), 7.58 (1H, d), 7.47 (1H, dd), 7.08 (1H, d), 5.07 (1H, q), 3.66 (41-1, t), 3.20 (4H, t), 1.45 (3H, d).

EXAMPLE 13

[[5-Chloro-4'(1-pyrrolidinylcarbonyl)-3'-(trifluoromethyl)[1,1'-biphenyl]-2-yl]oxy]-acetic acid

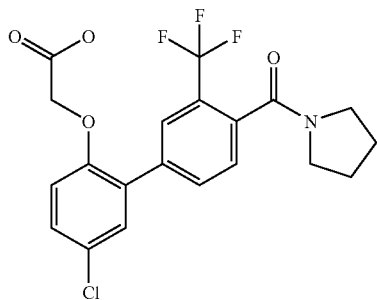

a) 4-Bromo-2-(trifluoromethyl)-benzoic acid

A mixture of 1-bromo-4-fluoro-3-(trifluoromethyl)benzene (5.02 g) and potassium cyanide (1.38 g) in DMSO (20 ml) was heated at 80° C. for 14 h. Water was added and the mixture was extracted ether, the organic extracts were dried (MgSO₄) and evaporated to give a brown oil. This was dissolved in DMSO (10 ml) and 4 M NaOH (10 ml) and heated at 100° C. for 16 h. 2 M Hcl (20 ml) was added and the mixture was extracted with DCM (three times), the organic extracts were dried (MgSO₄), evaporated and purified by chromatography (silica, CH₂Cl₂-MeOH—AcOH as eluent) to give the sub-title compound (1.99 g).
MS: ESI (−ve): 268 [M−H]⁻ 100%.

b) 1-[4-Bromo-2-(trifluoromethyl)benzoyl pyrrolidine

EDCI (1.70 g) was added to a solution of the product from step a) (1.97 g), pyrrolidine (1.2 ml) and DMAP (1.43 g) in DCM (10 ml) and THF (2 ml) and the resultant solution was stirred for 16 h. Aq HCl was added and the mixture was extracted with DCM (three times), the organic extracts were dried (MgSO₄), evaporated and purified by chromatography (silica, petrol—ether as eluent) to give the sub-title compound (616 mg).
¹H NMR CDCl₃: δ 8.27 (1H, d), 7.93 (1H, d), 7.74 (1H, dd), 7.25 (1H, d), 3.64 (2H, t), 3.11 (2H, t), 1.98 (2H, hex), 1.88 (2H, hex).

c) 1-[[5'-Chloro-2'-(phenylmethoxy)-3-(trifluoromethyl)[1,1'-biphenyl]-4-yl]carbonyl]-pyrrolidine The sub-title compound was prepared by the method of Example 11 step b) using the product of step b) and [5-chloro-2-(phenylmethoxy)phenyl]boronic acid. M.p. 143-4° C.
MS: ESI (+ve): 460 [M+H]⁺ 100% d) 1-[[5'-Chloro-2'-hydroxy-3-(trifluoromethyl)[1,1'-biphenyl]-4-yl]carbonyl]pyrrolidine The sub-title compound was prepared by the method of Example 11 step c) using the product of step c). M.p. 220-1° C.
MS: ESI (−ve): 368 [M−H]⁻ 100%.

e) Ethyl [[5-chloro-4'-(1-pyrrolidinylcarbonyl)-3'-(trifluoromethyl)[1,1'-biphenyl]-2-yl]oxy]-acetate The sub-title compound was prepared by the method of Example 2 step a) using the product from steps d) and ethyl bromoacetate.
¹H NMR CDCl₃: δ 7.92 (1H, s), 7.81 (1H, dd), 7.41 (1H, d), 7.33-7.28 (2H, m), 6.82 (1H, d), 4.61 (2H, s) 4.24 (2H, q), 3.68 (2H, t), 3.20 (2H, t), 1.98 (2H, hex), 1.90 (2H, hex), 1.26 (3H, t).

f) [[5-Chloro-4'-(1-pyrrolidinylcarbonyl)-3'-(trifluoromethyl)[1,1'-biphenyl]-2-yl]oxy]-acetic acid The title compound was prepared by the method of Example 5 step f) using the product from step e). M.p. 197-8° C.

MS: ESI (–ve): 426 [M–H]⁻ 100%

¹H NMR DMSO-D6: δ 8.09 (1H, s), 8.01 (1H, d), 7.51 (1H, d), 7.41 (1H, d), 7.32 (1H, dd), 6.97 (1H, d), 4.42 (2H, s), 3.47 (21-1, t), 3.10 (2H, t), 1.93-1.78 (4H, m).

EXAMPLE 14

(2S)-2-[[5-Chloro-4'-(1-pyrrolidinylcarbonyl)-3'-(trifluoromethyl)[1,1'-biphenyl]--yl]oxy]propanoic acid

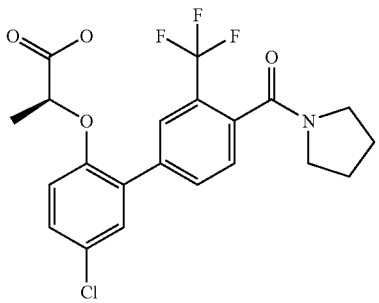

a) 1,1-Dimethylethyl (2S)-2-[[5-Chloro-4'-(1-pyrrolidinylcarbonyl)-3'-(trifluoromethyl)-[1,1'-biphenyl]-2-yl]oxy]propanoate The sub-title compound was prepared by the method of Example 4 step a) using the product from Example 13 step d).

¹H NMR CDCl₃: δ 8.03 (1H, s), 7.80 (1H, d), 7.40 (1H, dd), 7.31 (1H, d), 7.26-7.24 (1H, m), 6.77 (1H, d), 4.64 (1H, q), 3.68 (2H, t), 3.20 (2H, t), 1.99 (2H, hex), 1.90 (2H, hex), 1.49 (3H, d), 1.41 (9H, s).

b) (2S)-2-[[5-Chloro-4'-(1-pyrrolidinylcarbonyl)-3'-(trifluoromethyl)[1,1'-biphenyl]-2-yl]oxy]propanoic acid The sub-title compound was prepared by the method of Example 2 step e) using the product from step a). M.p. 164-5° C.

MS: ESI (–ve): 440 [M–H]⁻ 100%

¹H NMR DMSO-d6: δ 13.26 (1H, s), 8.44 (1H, d), 8.12 (2H, s), 7.58 (1H, d), 7.47 (1H, dd), 7.08 (1H, d), 5.07 (1H, q), 3.66 (4H, t), 3.20 (4H, t), 1.45 (3H, d).

EXAMPLE 15

[[5-Chloro-4'-(ethylsulfonyl)-3'-(trifluoromethyl)[1,1'-biphenyl]-2-yl]oxy]acetic acid

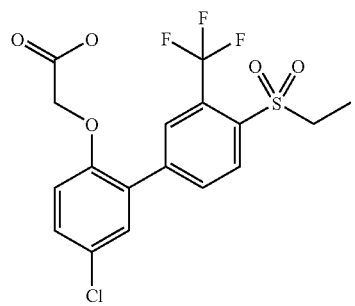

a) Methyl [[5-chloro-4'-(ethylsulfonyl)-3'-(trifluoromethyl)[1,1'-biphenyl]-2-yl]oxy]acetate The sub-title compound was prepared by the method of Example 2 step d) using the products from Example 7 step a) and Example 9 step b).

MS: APCI (–ve): 435 [M–H]⁻ 100% b) [[5-Chloro-4'-(ethylsulfonyl)-3'-(trifluoromethyl)[1,1'-biphenyl]-2-yl]oxy]acetic acid The title was prepared by the method of Example 6 step f) using the product from step a).

MS: ESI (–ve): 421 [M–H]⁻ 100%

¹H NMR DMSO-D6: δ 8.35 (1H, d), 8.21 (1H, d), 8.15 (1H, dd), 7.58 (1H, d), 7.48 (1H, dd), 7.17 (1H, d), 4.82 (2H, s) 3.42 (2H, q), 1.21 (3H, t).

EXAMPLE 16

(2S)-2-[[5-Chloro-4'-(methylsulfonyl)-(3'-trifluoromethyl)-[1,1'-biphenyl]-2-yl]oxy]propanoic acid

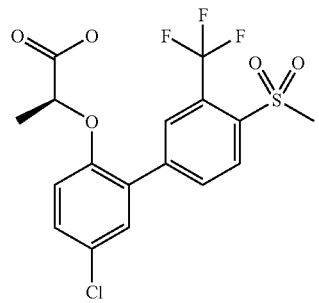

Methyl (2S)-2-[[5-chloro4'-(methylsulfonyl)-(3'-trifluoromethyl)-[1,1'-biphenyl]-2-yl]oxy]propanoate The sub-title compound was prepared by the method of Example 2 step d) using the products from Example 4 step b)

and Example 1 step b). Extensive saponification occurred during this reaction and the product was re-esterified using trimethylsilyldiazomethane in methanol.

MS: APCI (−ve): 435 [M−H]⁻ 100%

(2S)-2-[[5-Chloromethylsulfonyl)-(3'-trifluoromethyl)-[1,1'-biphenyl]-2-yl]oxy]propanoic acid The sub-title compound was prepared by the method of Example 6 step f) using the product from step a). M.p. 77-9° C.

MS: ESI (−ve): 421 [M−H]⁻ 100%

$^1$H NMR DMSO-d6) δ 8.48 (s, 1H), 8.28 (d, 1H), 8.18 (d, 1H), 7.58 (s, 1H), 7.47 (d, 1H), 7.09 (d, 1H), 5.06 (q, 1H), 3.40 (s, 3H), 1.45 (d, 3H)

EXAMPLE 17

(2S)-2-[[5-Chloro-3-fluoro-4'-(methylsulfonyl)[1,1'-biphenyl]-2-yl]oxy]propanoic acid

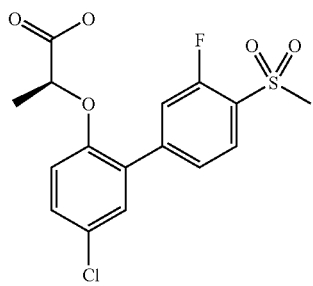

a) [3-Fluoro-4-(methylthio)phenyl]boronic acid

The sub-title compound was prepared by the method of Example 1 step c) using the product of step b).

MS: ESI (−ve): 185 [M−H]⁻ 100% b) 1,1-Dimethylethyl (2S)-2-[[5-Chloro-3'-fluoro-4'-(methylsulfonyl)[1,1'-biphenyl]-2-yl]oxy]propanoate The sub-title compound was prepared by the method of Example 2 step d) using the products from step a) and Example 4 step a).

$^1$H NMR DMSO-d6: δ 7.91 (1H, t), 7.82 (1H, dd), 7.73 (1H, dd), 7.52 (1H, d), 7.47 (1H, dd), 7.03 (1H, d), 4.99 (1H, q), 3.38 (3H, s), 1.44 (3H, d), 1.38 (9H, s).

c) (2S)-2-[[5-Chloro-3'-fluoro-4'-(methylsulfonyl)[1,1'-biphenyl]-2-yl]oxy]propanoic acid The sub-title compound was prepared by the method of Example 2 step e) using the product from step a). M.p. 190-2° C.

MS: ESI (−ve): 371 [M−H]⁻ 100%

$^1$H NMR DMSO-d6: δ 7.92-7.82 (2H, m), 7.74 (1H, dd), 7.50 (1H, d), 7.46 (1H, dd), 7.05 (1H, d), 5.02 (1H, q), 3.38 (3H, s), 1.46 (3H, d).

EXAMPLE 18

[[3',5-dichloro-4'-(1-pyrrolidinylcarbonyl) [1,1'-biphenyl]-2-yl]oxy]-acetic acid

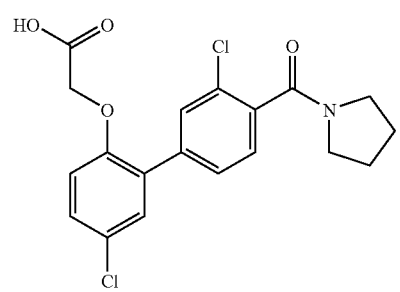

a) 1-(4-bromo-2-chlorobenzoyl)-pyrrolidine

Oxalyl chloride (0.56 ml) was added to a stirred suspension of 4-bromo-2-chloro-benzoic acid (0.5 g) in dichloromethane (10 ml). DMF (1 drop was added) and stirred for 1 h, then evaporated in vacuo. The product was dissolved in DCM (10 ml), triethylamine (0.21 ml) was added, followed by pyrrolidine (0.27 ml) and stirred overnight. Water was added and the organic layer separated, then washed with 1M HCl, dried (MgSO₄) and evaporated in vacuo. Yield 0.6 g MS: ESI (−ve): 249 (M−H)

b) 1-[(3,5'-dichloro-2'-methoxy[1,1'-biphenyl]-4-yl)carbonyl]-pyrrolidine

The product of step a) (0.6 g), 4-chloro-2-methoxy boronic acid (0.69 g), toluene (10 ml), ethanol (4 ml) and 2M Na₂CO₃ (2 ml) were charged to a flask and stirred. Tetrakistriphenylphospine palladium (0) (0.09 g) was added and the mixture stirred at reflux for 16 h. The mixture was concentrated in vacuo. The residue was purified by flash column chromatography eluting with isohexane:ethyl acetate (6:4) to give the sub-title compound.

Yield 0.68 g.
MS: ESI (+ve): 350 (M+H)

c) 1-[(3,5'-dichloro-2'-hydroxy[1,1'-biphenyl]-4-yl)carbonyl]-pyrrolidine

The product from step b) (0.6 g) was dissolved in DCM (20 ml) and treated with boron tribromide (7 ml) and stirred for 1 h. Ice was added and a solid formed, which was filtered to give the sub-title compound. Yield 0.46 g.

MS: ESI (−ve): 335 (M−H)

d) [[3',5-dichloro-4'-(1-pyrrolidinylcarbonyl)[1,1'-biphenyl]-2-yl]oxy]-acetic acid The product from step c) (180 mg), tert-butyl bromoacetate (0.07 ml), potassium carbonate (0.1 g) and DMF (10 ml) were charged to a flask and stirred for 16 h. Water was added and then washed with ethyl acetate. The organic extracts were dried (MgSO₄) and evaporated in vacuo. The residue was purified by flash column chromatography eluting with isohexane:ethyl acetate (8:2). The sub-title compound was dissolved in DCM (8 ml) and TFA (2 ml) was added, stirred for 1 h, then concentrated in vacuo. Trituration with a mixture of ether and isohexane gave a solid, which was further purified by reverse phase HPLC to give the title compound. Yield (48 mg)

$^1$H NMR DMSO-D6: δ 7.81 (1H, s), 7.64 (1H, d), 7.42-7.35 (3H, m), 7.02 (1H, d), 4.6 (2H, s), 3.58-3.01 (6H, m) and 1.86 (2H, d).

MS: APCI (−ve): 392 (M−H)

EXAMPLE 19

[[3',5-dichloro-4'-(4-morpholinylcarbonyl)[1,1'-biphenyl]-2-yl]oxy]-actic acid

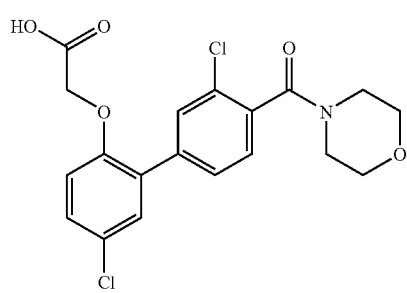

a) 4-(4-bromo-2-chlorobenzoyl)-morpholine

The sub-title compound was prepared by the method of example 18 part a) using morpholine MS: ESI (−ve): 306 (M−H)

b) 4-[(3,5'-dichloro-2'-hydroxy[1,1'-biphenyl]-4-yl)carbonyl]-morpholine

The sub-title compound was prepared by the methods of example 18 step b) and c) using the product from step a) and 4-chloro-2-methoxy boronic acid.

MS: ESI (−ve): 351 (M−H)

c) [[3',5-dichloro-4'-(4-morpholinylcarbonyl)[1,1'-biphenyl]-2-yl]oxy]-acetic acid The title compound was prepared by the method of example 18 step d) using the product of step b).

$^1$H NMR DMSO-D6: δ 7.81 (1H, s), 7.67 (1H, d), 7.73-7.30 (3H, m), 7.04 (1H, d), 4.64 (2H, s), 3.72-3.50 (6H, m) and 3.22 (2H, t).

MS: APCI (−ve): 408 (M−H)

EXAMPLE 20

[[4'-(1-azetidinylcarbonyl)-3',5-dichloro[1,1'-biphenyl]-2-yl]oxy]-acetic acid

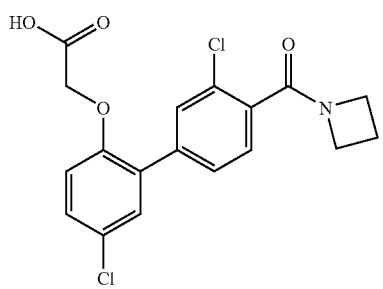

a) 1-(4-bromo-2-chlorobenzoyl)-azetidine

The sub-title compound was prepared by the method of example 18 part a) using azetidine hydrochloride MS: ESI (−ve): 273 (M−H)

b) 1-[(3,5'-dichloro-2'-methoxy[1,1'-biphenyl]-4-yl)carbonyl]-azetidine

The sub-title compound was prepared by the method of example 18 steps b) and c) using the product from step a) and 4-chloro-2-methoxy boronic acid.

MS: ESI (+ve): 322 (M+H)

c) [[4'-(1-azetidinylcarbonyl)-3',5-dichloro[1,1'-biphenyl]-2-yl]oxy]-acetic acid The title compound was prepared by the method of example 18 step d) using the product of step b).

$^1$H NMR DMSO-D6: δ 7.82 (1H, s), 7.7 (1H, d), 7.43 (1H, d), 7.38-7.29 (2H, m), 6.93 (1H, d), 4.36 (2H, s), 4.16 (2H, t), 3.96 (2H, t) and 2.3 (2H, q).

MS: APCI (−ve): 378 (M−H)

EXAMPLE 21

[[3',5-dichloro-4'-[[(2R,6S)-2,6-dimethyl-1-piperidinyl]carbonyl][1,1'-biphenyl]-2-yl]oxy]-acetic acid

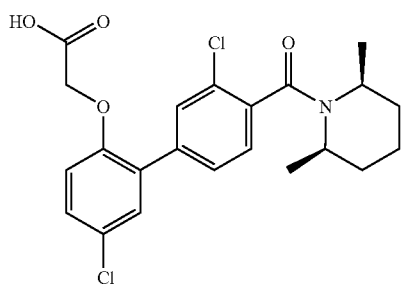

a) 3,5'-dichloro-2'-methoxy-[1,1'-biphenyl]-4-carboxylic acid 4-bromo-2-chlorobenzoic acid (0.4 g), 5-chloro-2-methoxybenzoic acid (0.4 g), Pd(dppf)Cl$_2$ (0.12 g), sodium carbonate (0.9 g), dioxan (15 ml) and methanol (5 ml) were charged to a flask and heated at reflux for 16 h. Cooled to room temp and filtered (hyflo). The filtrate was concentrated in vacuo, then dissolved in ethyl acetate. The suspension was made basic by addition of dilute NaOH. The aqueous layer was separated and acidified using 2M HCl, extracted with EtOAc, dried (MgSO$_4$) and evaporated in vacuo to give the sub-title compound Yield 0.4 g
$^1$H NMR DMSO-D6: δ 13.37 (1H, s), 7.86 (1H, m), 7.64 (1H, s), 7.41-7.38 (3H, m), 7.2 (1H, d) and 3.8 (3H, s).

b) (2R,6S)-1-[(3,5'-dichloro-2'-methoxy[1,1'-biphenyl]-4-yl)carbonyl]-2,6-dimethylpiperidine The sub-title compound was prepared by the method of example 18 step a) using the product of step a) and 2,6-dimethyl cis-piperazine.
MS: ESI (+ve): 393 (M+H)

c) (2R,6S)-1-[(3,5'-dichloro-2'-hydroxy[1,1'-biphenyl]-4-yl)carbonyl]-2,6-dimethyl piperidine The sub-title compound was prepared by the method of example 18 step c) using the product of step b).
MS: ESI (+ve): 378 (M+H)

d) [[3',5-dichloro-4'-[[(2R,6S)-2,6-dimethyl-1-piperidinyl]carbonyl][1,1'-biphenyl]-2-yl]oxy]-acetic acid The title compound was prepared by the method of example 18 step d) using the product of step c).
$^1$H NMR DMSO-D6: δ 7.78 (1H, dd), 7.64-7.57 (1H, m), 7.43-7.3 (3H, m), 7.1-7.02 (1H, m), 4.97 (2H, s), and 1.96-1.04 (14H, m).
MS: APCI (–ve): 436 (M–H)

EXAMPLE 22

[[3',5-dichloro-4'-[(2-methyl-1-pyrrolidinyl)carbonyl][1,1'-biphenyl]-2-yl]oxy]-acetic acid

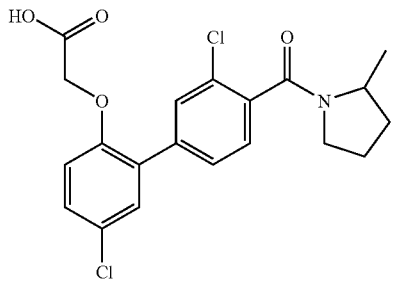

a) 1-[(3,5'-dichloro-2'-methoxy[1,1'-biphenyl]-4-yl)carbonyl]-2-methyl-pyrrolidine The sub-title compound was prepared by the method of example 18 step a) using the product of step example 21 step a) and 2-methylpyrrolidine.
MS: ESI (+ve): 364 (M+H)

b) 1-[(3,5'-dichloro-2'-hydroxy[1,1'-biphenyl]-4-yl)carbonyl]-2-methyl-pyrrolidine The sub-title compound was prepared by the method of example 18 step c) using the product of step a).
MS: ESI (+ve): 350 (M+H)

c) [[3',5-dichloro-4'-[(2-methyl-1-pyrrolidinyl)carbonyl][1,1'-biphenyl]-2-yl]oxy]-acetic acid The title compound was prepared by the method of example 18 step d) using the product of step b).
$^1$H NMR DMSO-D6: δ 7.73 (1H, s), 7.6 (1H, d), 7.42-7.35 (3H, m), 7.06 (1H, d), 4.68 (2H, s), 4.2-4.13 (1H, m), 3.24-2.82 (2H, m, +DMSO), 2.17-1.51 (4H, m) 1.23 (3H, d) and 0.98-0.86 (1H, m).
MS: APCI (–ve): 378 (M–H)

EXAMPLE 23

[[3',5-dichloro-4'-(2-isoxazolidinylcarbonyl)[1,1'-biphenyl]-2-yl]oxy]-acetic acid

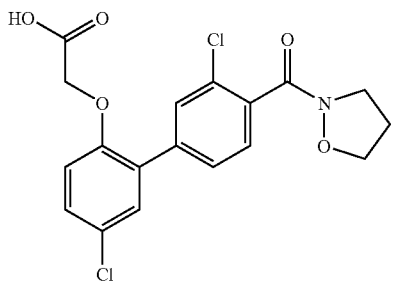

a) 2-[(3,5'-dichloro-2'-methoxy[1,1'-biphenyl]-4-yl)carbonyl]-isoxazolidine

The sub-title compound was prepared by the method of example 21 step b) using the product of example 21 step a) and isoxazolidine.
MS: ESI (+ve): 352 (M+H)

b) 2-[(3,5'-dichloro-2'-hydroxy(1,1'-biphenyl]-4-yl)carbonyl]-isoxazolidine

The sub-title compound was prepared by the method of example 18 part c) using the product of step a).
MS: ESI (+ve): 338 (M+H)

c) [[3',5-dichloro-4'42-isoxazolidinylcarbonyl)(1,1'-biphenyl]-2-yl]oxy]-acetic acid The title compound was prepared by the method of example 18 step d) using the product of step b).
$^1$H NMR DMSO-D6: δ 7.84 (1H, s), 7.62 (1H, dd), 7.42 (1H, d), 7.38-7.29 (2H, m), 6.93 (1H, d), 4.32 (2H, s), 3.93 (2H, t), 3.7 (2H, t, broad) and 2.39-2.22 (2H, m).
MS: APCI (+ve): 396 (M+H)

EXAMPLE 24

[[5-chloro-3'-fluoro-4'4l-pyrrolidinylcarbonyl)[1,1'-biphenyl]-2-yl]oxy]-acetic acid a) 1-(4-bromo-2-fluorobenzoyl)-pyrrolidine

The sub-title compound was prepared by the method of example 18 step a) using 4-bromo-2-fluoro-benzoic acid and pyrrolidine.

b) 1-[(5'-chloro-3-fluoro-2'-methoxy[1,1'-biphenyl]-4-yl)carbonyl]-pyrrolidine The sub-title compound was prepared by the method of example 18 step b) using the product from step a) and 4-chloro-2-methoxy boronic acid.
MS: ESI (−ve): 333 (M+H)

c) 1-[(5'-chloro-3-fluoro-2'-hydroxy[1,1'-biphenyl]-4-yl)carbonyl]-pyrrolidine The sub-title compound was prepared by the method of example 18 step c) using the product of step b).
MS: ESI (+ve): 320 (M+H)

d) [[5-chloro-3'-fluoro-4'-(1-pyrrolidinylcarbonyl)[1,1'-biphenyl]-2-yl]oxy]-acetic acid, ethyl ester The product of step c) (0.11 g) was dissolved in DMF (5 ml), ethylbromoacetate (0.04 ml) and potassium carbonate (0.1 g) were added. The reaction mixture was stirred for 16 h at RT. Water and ethyl acetate were added. The organic layer was removed, dried (MgSO$_4$) and evaporated in vacuo. The residue was purified by flash column chromatography eluting with isohexane:ethyl acetate (1:1) to give the sub-title compound. Yield 0.12 g.
MS: ESI (+ve): 406 (M+H)

e) [[5-chloro-3'-fluoro-4'-(1-pyrrolidinylcarbonyl)[1,1'-biphenyl]-2-yl]oxy]-acetic acid The title compound was prepared by the method of example 6 step f) using the product of step d).
$^1$H NMR DMSO-D6: δ 13.12 (1H, s), 7.6-7.4 (5H, m), 7.08 (1H, d), 4.8 (2H, s), 3.48-3.46 (2H, m), 3.38-3.13 (2H, m), 1.91-1.84 (4H, m).
MS: APCI (−ve): 376 (M−H)

EXAMPLE 25

(2S)-2-[[5-chloro-3'-fluoro-4'-(1-pyrrolidinylcarbonyl)[1,1'-biphenyl]-2-yl]oxy]-1,1-propanoic acid a) (2S)-2-[[5-chloro-3'-fluoro-4'-(1-pyrrolidinylcarbonyl)[1,1'-biphenyl]-2-yl]oxy]-1,1-dimethylethyl ester, propanoic acid The sub-title compound was prepared by the method of example 1 step e) using the product of example 24 step c)
MS: ESI (+ve): 448 (M+H)

b) (2S)-2-[[5-chloro-3'-fluoro-4'-(1-pyrrolidinylcarbonyl)[1,1'-biphenyl]-2-yl]oxy]-propanoic acid The product of step a) (0.23 g) was dissolved in dichloromethane (6 ml) and TFA (1.5 ml) was added, the solution was stirred for 2 hours, then concentrated in vacuo, diluted with 1M NaOH and ethyl acetate. The aqueous layer was separated and acidified using 2M HCl, then extracted with ethyl acetate (×2). The organic layers were dried (MgSO$_4$) and evaporated in vacuo to give the title compound. Yield 0.18 g.
$^1$H NMR DMSO-D6: δ 7.67-7.44 (5H, m), 7.07 (1H, d), 5.03 (1H, q), 3.58 (2H, t), 3.25 (2H, t), 2.02-1.83 (4H, m), 1.5 (3H, d).
MS: APCI (−ve): 390 (M−H)

EXAMPLE 26

[[3'-methyl-4'-(1-piperidinylcarbonyl)-5-(trifluoromethyl)[1,1'-biphenyl]-2-yl]oxy]-acetic acid a) [2-borono-4-(trifluoromethyl)phenoxy]-acetic acid, 1,1-dimethylethyl ester To a flask, purged with nitrogen, was charged bis(dibenzylideneacetone)palladium(0) (1.4 g), tricyclohexylphosphine (0.57 g), potassium acetate (4.14 g), [2-bromo-4-(trifluoromethyl)phenoxy]-acetic acid, 1,1-dimethylethyl ester [WO2004089885] (10 g), dioxane (80 ml) and bis(pinacolato)diboron (7.86 g). The mixture was heated to 100° C. for 3 hours, cooled and then filtered before water (50 ml) was added to the filtrates which were stirred overnight at room temperature. The mixture was poured into water (300 ml), extracted with ethylacetate, washed with brine, dried (MgSO$_4$) and concentrated in vacuo to give crude material. Purification using flash column chromatography (eluent 10% ethylacetate/hexane increasing to 20% ethylacetate/hexane) gave the sub-title compound as a solid (4.1 g).

$^1$H NMR DMSO-d6: δ 8.03 (2H, s), 7.91 (1H, d), 7.76 (1H, t), 7.13 (1H, d), 4.83 (2H, s), 1.47 (9H, s).

b) 1-(4-bromo-2-methylbenzoyl)-piperidine

The sub-title compound was prepared by the method of example 18 step a) using 4-bromo-2-methyl benzoic acid and piperidine.

MS: ESI (+ve): 282 (M+H)

c) [[3'-methyl-4'-(1-piperidinylcarbonyl)-5-(trifluoromethyl)[1,1'-biphenyl]-2-yl]oxy]-acetic acid The title compound was prepared by the method of example 21 step a) using the products of step a) and step b).

$^1$H NMR DMSO-D6: δ 7.67-(1H, d), 7.6 (1H, s), 7.45-7.41 (2H, m), 7.19-7.13 (2H, m), 4.72 (2H, s), 3.65-3.6 (2H, m), 3.17 (2H, t), 2.25 (3H, s), 1.62-1.39 (6H, m).

MS: APCI (−ve): 420 (M−H)

EXAMPLE 27

[[3'-methyl-4'-(1-pyrrolidinylcarbonyl 1)-5-(trifluoromethyl)(1,1'-biphenyl]-2-yl]oxy]-acetic acid

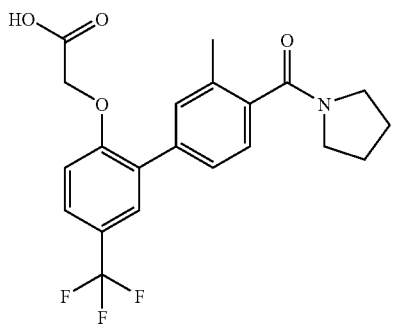

a) 1-(4-bromo-2-methylbenzoyl)pyrrolidine

The sub-title compound was prepared by the method of example 18 step a) using 4-bromo-2-methyl benzoic acid and pyrrolidine.

MS: ESI (+ve): 268 (M+H)

b) [[3'-methyl-4'-(1-pyrrolidinylcarbonyl 1)-5-(trifluoromethyl)[1,1'-biphenyl]-2-yl]oxy]-acetic acid The title compound was prepared by the method of example 21 step a) using the product of step a) and the product of example 26 step a).

$^1$H NMR DMSO-D6: δ 13.08 (1H, s), 7.7-7.42 (4H, m), 7.31-7.18 (2H, m), 4.86 (2H, s), 3.49 (2H, t), 3.13 (2H, t), 2.26 (3H, s), 1.91-1.8 (4H, m).

MS: APCI (−ve): 407 (M−H)

EXAMPLE 28

(2S)-2-[[4'-[[bis(1-methylethyl)amino]carbonyl]-5-chloro-3'-fluoro[1,1'-biphenyl]-2-yl]oxy]-propanoic acid

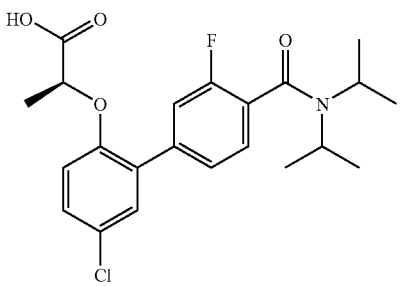

a) 2-[5-chloro-2-(phenylmethoxy)phenyl]-4,4,5,5-tetramethyl-1,3,2-dioxaborolane Pinacol (3.24 g) was added to a solution of [5-chloro-2-(phenylmethoxy)phenyl]-boronic acid (6 g) in diethyl ether, and stirred for 24 h. 4A molecular sieves and pinacol (1.5 g) were added, stirred for a further 24 h. The sieves were filtered and the filtrate was washed with water and brine, then dried (MgSO$_4$) and concentrated in vacuo. Yield 6.8 g.

$^1$H NMR DMSO-D6: δ 7.6-7.25 (7H, m), 7.08 (1H, d), 5.13 (2H, s), 1.32 (12H, s)

b) 4-chloro-2-(4,4,5,5-tetramethyl-1,3,2-dioxaborolan-2-yl)-phenol

10% Palladium on activated carbon was added to a solution of the product from step a) (4 g) in ethanol (100 ml), and stirred under 1 bar hydrogen for 30 min. The mixture was filtered and the filtrate was concentrated in vacuo to give the sub-title compound. Yield 3.51 g. Used without characterisation.

c) (2S)-2-(2-borono-4-chlorophenoxy)-propanoic acid

DIAD (3 ml) was added to a mixture of the product from step b) (3.51 g), triphenyl phosphine (3.98 g), tert-butyl (R)-(+) lactate (2.02 g) and THF (80 ml) at 0° C. overnight. The mixture was concentrated in vacuo. The residue was purified by flash column chromatography eluting with isohexane: ethyl acetate (7:3) to give the sub-title compound (4 g). The intermediate obtained was dissolved in acetone and 1M HCl (15 ml) was added, stirred for 20 min, then concentrated in vacuo. Redissolved in dichloromethane (10 ml) and added TFA (5 ml). Stirred for 2 h, then added water (1 ml), stirred for 1 h. The reaction mixture was then diluted (water) and made alkaline by adding dilute NaOH. The organic layer was separated and discarded. The aqueous phase was acidified with concentrated HCl to pH 1, then washed with dichloromethane (×2). These organic extracts were dried (MgSO$_4$) then concentrated in vacuo to give the sub-title compound. Yield 1.4 g MS: ESI (−ve): 244 (M−H)

d) 4-bromo-2-fluoro-N,N-bis(1-methylethyl)-benzamide

The sub-title compound was prepared by the method of example 18 step a) using 4-bromo-2-fluorobenzoic acid and diisopropylamine.

MS: ESI (+ve): 304 (M+H)

e) (2S)-2-[[4'-[[bis(1-methylethyl)amino]carbonyl]-5-chloro-3'-fluoro[1,1'-biphenyl]-2-yl]oxy]-propanoic acid The product of step c) (200 mg), the product of step d) (200 mg), Pd(dppf)Cl$_2$ (60 mg), sodium carbonate (350 mg) and dioxan (5 ml) were charged to a flask and heated at reflux for 24 h, then cooled to room temp and filtered (hyflo). The filtrate was concentrated in vacuo, then purified by reverse phase HPLC to give the title compound. Yield 22 mg $^1$H NMR DMSO-D6: δ 13.19 (1H, s), 7.62-7.21 (5H, m), 6.92 (1H, m), 4.97 (1H, q), 3.8-3.46 (2H, m) 1.47 (12H, s), and 1.18 (3H, d).

EXAMPLE 29

(2S)-2-[[5-chloro-4'-[(ethylmethylamino)carbonyl]-3'-fluoro[1,1'-biphenyl]-2-yl]oxy]-propanoic acd

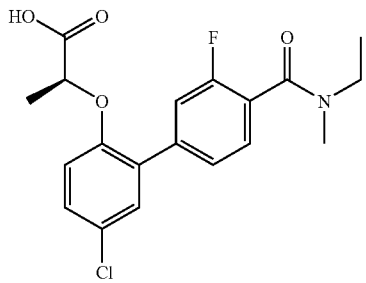

a) 4-bromo-N-ethyl-2-fluoro-N-methyl-benzamide

The sub-title compound was prepared by the method of example 18 step a) using 4-bromo-2-fluorobenzoic acid and N-methyl-ethanamine.

b) (2S)-2-[[5-chloro-4'-[(ethylmethylamino)carbonyl]-3'-fluoro[1,1'-biphenyl]-2-yl]oxy]-propanoic acid The title compound was prepared by the method of example 28 step e) using the product of step a) and the product of example 28 step c)

$^1$H NMR DMSO-D6: δ 7.7 (1H, d), 7.55 (1H, d), 7.4-7.19 (3H, m), 7.02-6.9 (1H, m), 4.62 (1H, q), 3.5-3.2 (2H, q), 2.3 (3H, d), 1.4 (3H, d) and 1.04-1.18 (3H, m).

MS: ESI (−ve): 378 (M−H)

EXAMPLE 30

(2S)-2-[[5-chloro-3'-fluoro-4'-[[methyl(1-methylethyl)amino]carbonyl][1,1'-biphenyl]-2-yl]oxy]-propanoic acid

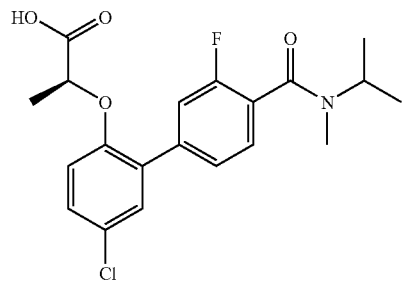

a) 4-bromo-2-fluoro-N-methyl-N-(1-methylethyl)-benzamide

The sub-title compound was prepared by the method of example 18 step a) using 4-bromo-2-fluorobenzoic acid and N-methyl-2-propanamine.

b) (2S)-2-[[5-chloro-3'-fluoro-4'-[[methyl(1-methylethyl)amino]carbonyl][1,1'-biphenyl]-2-yl]oxy]-propanoic acid The title compound was prepared by the method of example 28 step e) using the product of step a) and the product of example 28 step c)

$^1$H NMR DMSO-D6: δ 7.57-7.31 (5H, m), 7.02 (1H, d), 4.9 (1H, q), 3.8 (1H, s, broad), 3.19 (2H, s, broad+water), 2.52 (3H, s) and 1.43 (1H, d), 1.22-1.16 (6H, m)

MS: APCI (−ve): 392 (M−H)

EXAMPLE 31

(2S)-2-[[5-chloro-4'-[(diethylamino)carbonyl]-3'-fluoro[1,1'-biphenyl]-2-yl]oxy]-propanoic acid

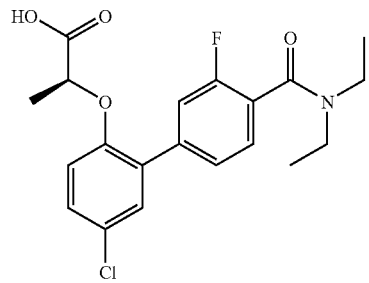

a) 4-bromo-N,N-diethyl-2-fluoro-benzamide

The sub-title compound was prepared by the method of example 18 step a) using 4-bromo-2-fluorobenzoic acid and N-ethyl-ethanamine.

b) (2S)-2-[[5-chloro-4'-[(diethylamino)carbonyl]-3'-fluoro[1,1'-biphenyl]-2-yl]oxy]-propanoic acid The title compound was prepared by the method of example 28 step e) using the product of step a) and the product of example 28 step c)

¹H NMR. DMSO-D6: δ 7.76-7.21 (5H, m), 6.96 (1H, s), 4.71 (1H, q, broad), 3.47 (2H, s, broad), 3.19 (2H, s, broad), 1.4 (3H, d), 1.16 (3H, t) and 1.04 (3H, t).

MS: ESI (–ve): 392 (M–H)

EXAMPLE 32

(2S)-2-[[5-chloro-4'-[(3,3-difluoro-1-pyrrolidinyl)carbonyl]-3'-fluoro[1,1'-biphenyl]-2-yl]oxy-propanoic acid

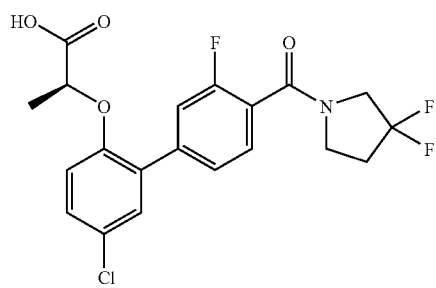

a) 1-(4-bromo-2-fluorobenzoyl)-3,3-difluoro-pyrrolidine

The sub-title compound was prepared by the method of example 18 step a) using 4-bromo-2-fluorobenzoic acid and 3,3-difluoropyrrolidine, hydrochloride salt and triethylamine (2 molar equivalent).

b) (2S)-2-[[5-chloro-4'-[(3,3-difluoro-1-pyrrolidinyl)carbonyl]-3'-fluoro[1,1'-biphenyl]-2-yl]oxy]-propanoic acid Tetrakispalladiumtriphenylphosphine (0) (0.14 g) was added to a mixture of the product of example 28 step c) (0.3 g), toluene (10 ml), 2M sodium carbonate solution (4 ml), ethanol (4 ml) and the product of step a). The reaction mixture was heated at 90° C. overnight, then concentrated in vacuo. The residue was filtered (hyflo) and the filtrate was purified by reverse phase HPLC to give the title compound. Yield 0.12 g.

¹H NMR DMSO-D6: δ 7.7-7.36 (5H, m), 6.9 (1H, d), 4.8 (1H, d), 3.9 (1H, t), 3.83-3.66 (1H, m), 3.6-3.45 (2H, m) 2.5 (1H, m), 2.07 (1H, s) and 1.44 (3H, d).

MS: ESI (–ve): 426 (M–H)

EXAMPLE 33

(2S)-2-[[4'-[[(1,1-dimethylethyl)amino]carbonyl]-3'-fluoro-5-(trifluoromethyl)[1,1'-biphenyl]-2-yl]oxy]-propanoic acid

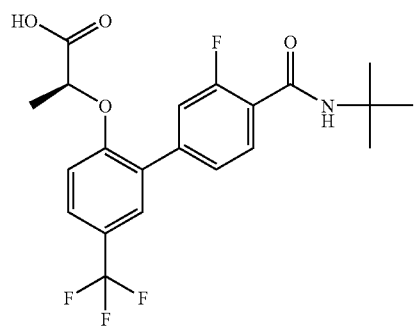

a) 4-bromo-N-(1,1-dimethylethyl)-2-fluoro-benzamide

The sub-title compound was prepared by the method of example 18 step a) and tertiary-butyl amine.

¹H NMR DMSO-D6: δ 7.6 (1H, t), 7.4 (1H, dd), 7.3 (1H, dd), 6.57-6.44 (1H, m) and 1.44 (9H, s).

b) (2S)-2-[[4'-[[(1,1-dimethylethyl)amino]carbonyl]-3'-fluoro-5-(trifluoromethyl) [1,1'-biphenyl]-2-yl]oxy]-propanoic acid The title compound was prepared using the product of step a) and (2S)-2-[2-borono-4-(trifluoromethyl)phenoxy]-propanoic acid [WO2004089885] by the method of example 32 step b).

¹H NMR DMSO-D6: δ 7.9 (1H, s), 7.9-7.53 (5H, m), 7.16 (1H, d), 5.05 (1H, d), 1.47-1.16 (12H, m).

MS: APCI (–ve): 374 (M–H)

EXAMPLE 34

(2S)-2-[[5-chloro-3'-fluoro-4'-[[(1-methylethyl)amino]carbonyl][1,1'-biphenyl]-2-yl]oxy]-propanoic acid

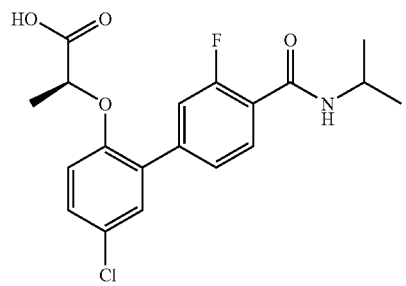

a) 4-bromo-2-fluoro-N-(1-methylethyl)-benzamide

The sub-title compound was prepared by the method of example 18 step a) using 4-bromo-2-fluorobenzoic acid and 2-propanamine.

¹H NMR CDCl₃: δ 7.97 (1H, t), 7.41 (1H, dd), 7.37 (1H, dd), 6.45 (1H, s), 4.33-4.25 (1H, m), 1.22 (6H, d), b) (2S)-2-[[5-chloro-3'-fluoro-4'-[[(1-methylethyl)amino]carbonyl][1,1'-biphenyl]-2-yl]oxy]-propanoic acid The title compound was prepared by the method of example 32 step b) using the product of step a) and the product of example 28 step c).

¹H NMR DMSO-D6: δ 8.21 (1H, d), 7.71-7.26 (4H, m), 6.97 (1H, d), 4.92 (1H, d), 4.07 (1H, d), 2.52 (broad peak, contains DMSO and 1H), 1.4 (3H, d) and 1.16 (6H, d), MS: APCI (+ve): 380 (M+H)

EXAMPLE 35

(2S)-2-[5-chloro-3'-fluoro-4'-[[(2-methylpropyl)amino]carbonyl][1,1'-biphenyl]-2-yl]oxy]-propanoic acid

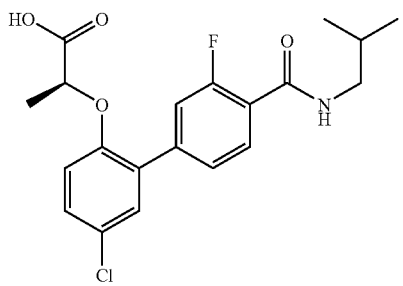

a) 4-bromo-2-fluoro-N-(2-methylpropyl)-benzamide

The sub-title compound was prepared by the method of example 18 step a) using 4-bromo-2-fluorobenzoic acid and 2-methyl-1-propanamine.

MS: ESI (+ve): 274 (M+H)

b) (2S)-2-[[5-chloro-3'-fluoro-4'-[[(2-methylpropyl)amino]carbonyl][1,1'-biphenyl]-2-yl]oxy]-propanoic acid The title compound was prepared by the method of example 32 step b) using the product of step a) and the product of example 28 step c).

¹H NMR DMSO-D6: δ 8.36 (1H, s), 7.7-7.42 (3H, m), 7.42-7.31 (2H, m), 6.96 (1H, d), 4.82 (1H, q), 3.08 (2H, t), 1.94-1.73 (1H, m), 1.4 (3H, d) and 0.9 (6H, m).

MS: APCI (+ve): 394 (M+H)

EXAMPLE 36

(2S)-2-[[3'-fluoro-4'-(1-pyrrolidinylcarbonyl)-5-(trifluoromethyl)[1,1'-biphenyl]-2-yl]oxy]-propanoic acid

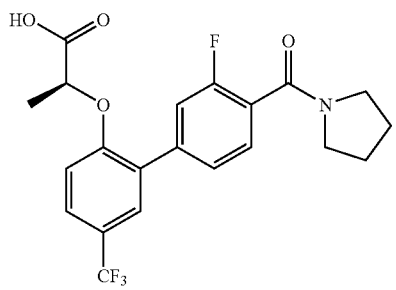

The title compound was prepared using the product of example 24 part a) and to (2S)-2-[2-borono-4-(trifluoromethyl)phenoxy]-propanoic acid [WO2004089885] by the method of example 32 step b).

¹H NMR DMSO-D6: δ 7.88 (1H, d), 7.7-7.51 (3H, m), 7.43 (1H, t), 7.05 (1H, d), 4.54 (1H, q), 3.58-3.06 (4H, m), 1.84 (4H, s) and 1.38 (3H, d).

MS: APCI (−ve): 424 (M−H)

EXAMPLE 37

(2S)-2-[[3',5-dichloro-4'-(1-pyrrolidinylcarbonyl)[1,1'-biphenyl]-2-yl]oxy]-propanoic acid

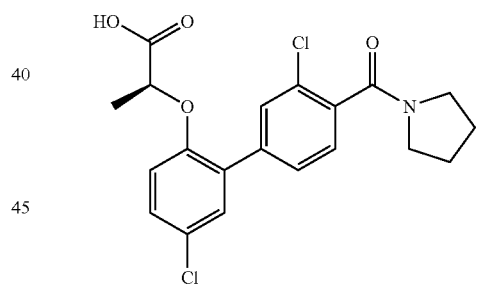

a) (2S)-2-[[3',5-dichloro-4'-(1-pyrrolidinylcarbonyl)[1,1'-biphenyl]-2-yl]oxy]-1,1-dimethylethyl ester propanoic acid The sub-title compound was prepared by the method of example 1 step e) using the product of example 18 step c).

b) (2S)-2-[[3',5-dichloro-4'-(1-pyrrolidinylcarbonyl)[1,1'-biphenyl]-2-yl]oxy]-propanoic acid The title compound was prepared by the method of example 25 step b) using the product of step a).

¹H NMR DMSO-D6: δ 7.82 (1H, s), 7.63 (1H, d), 7.45-7.39 (3H, m), 7.01 (1H, d), 4.96 (1H, q), 3.5 (2H, t), 1.97-1.81 (4H, m) and 1.42 (3H, d).

MS: APCI (−ve): 406 (M−H)

EXAMPLE 38

(2S)-2-[[5-chloro-3'-methyl-4'-(1-pyrrolidinylcarbonyl)[1,1'-biphenyl]-2-yl]oxy]-propanoic acid

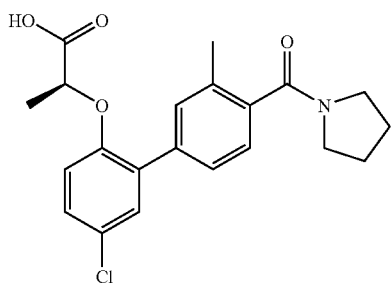

a) 1-[(5-chloro-2'-hydroxy-3-methyl[1,1'-biphenyl]-4-yl)carbonyl]-pyrrolidine

The sub-title compound was prepared by the method of example 18 step b) using the product of example 27 step a)
MS: ESI (−ve): 315 (M−H)

b) (2S)-2-[[5-chloro-3'-methyl-4'-(1-pyrrolidinylcarbonyl)[1,1'-biphenyl]-2-yl]oxy]-1,1-dimethylethyl ester propanoic acid The sub-title compound was prepared by the method of example 1 step e) using the product of step a)
MS: ESI (−ve): 442 (M−H)

c) (2S)-2-[[5-chloro-3'-methyl-4'-(1-pyrrolidinylcarbonyl)[1,1'-biphenyl]-2-yl]oxy]-propanoic acid The product of step b) (0.2 g) was dissolved in dichloromethane (3 ml) and TFA (3 ml) was added and stirred for 2 hours, then concentrated in vacuo. Purified by reverse phase HPLC to give the title compound.
$^1$H NMR DMSO-D6: δ 7.54 (2H, s), 7.37-7.21 (3H, m), 6.92 (1H, d), 4.76 (1H, d), 3.5 (2H, s), 3.11 (2H, s), 2.23 (3H, s), 1.98-1.77 (4H, m) and 1.4 (3H, d).
MS: APCI (+ve): 388 (M+H)

EXAMPLE 39

[[5-chloro-3'-methyl-4'-(1-pyrrolidinylcarbonyl)[1,1'-biphenyl]-2-yl]oxy]-acetic acid

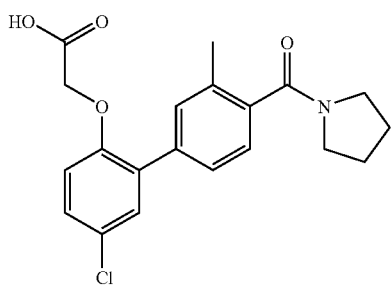

The title compound was prepared by the method of example 18 step d) using the ic, product of example 38 step a).
$^1$H NMR DMSO-D6: δ 7.57-7.18 (5H, m), 7.0 (1H, s), 4.63 (2H, s), 3.48 (2H, s), 3.12 (2H, s), 2.24 (3H, s) and 2.0-1.72 (4H, m).
MS: APCI (+ve): 374 (M+H)

EXAMPLE 40

[[3'-fluoro-4'-(1-pyrrolidinylcarbonyl)-5-(trifluoromethyl)[1,1'-biphenyl]-2-yl]oxy]-acetic acid

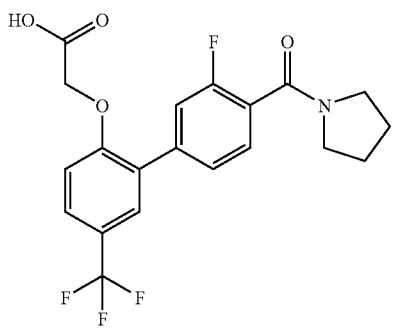

a) [[3'-fluoro-4'-(1-pyrrolidinylcarbonyl)-5-(trifluoromethyl)[1,1'-biphenyl]-2-yl]oxy]-acetic acid-1,1-dimethylethyl ester The sub-title compound was prepared by the method of example 32 step b) using the product of example 26 step a) and the product of example 24 step a).

b) [[3'-fluoro-4'-(1-pyrrolidinylcarbonyl)-5-(trifluoromethyl)[1,1'-biphenyl]-2-yl]oxy]-acetic acid The title compound was prepared by the method of example 38 step c) using the product of step a).
$^1$H NMR DMSO-D6: δ 7.73 (1H, dd), 7.70 (1H, d), 7.59 (1H, dd), 7.54-7.46 (2H, m), 7.26 (1H, d), 4.6 (2H, s), 3.49 (2H, t), 3.27 (2H, t), and 1.94-1.8 (4H, m).
MS: APCI (+ve): 412 (M+H)

EXAMPLE 41

(2S)-2-[[3'-methyl-4'-(1-pyrrolidinylcarbonyl)-5-(trifluoromethyl)[1,1'-biphenyl]-2-yl]oxy]-propanoic acid

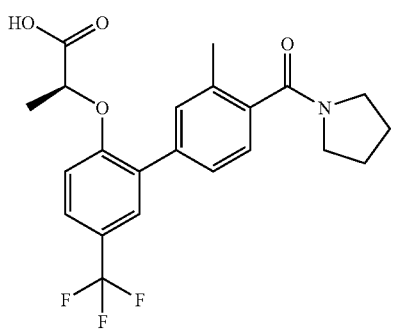

The title compound was prepared using the product of example 27 step a) and (2S)-2-[2-borono-4-(trifluoromethyl) phenoxy]-propanoic acid [WO2004089885] by the is method of example 32 step b).

$^1$H NMR DMSO-D6: δ 7.78-7.43 (4H, m), 7.23 (1H, d), 7.06 (1H, d), 5.04 (1H, d), 3.37 (2H, d), 3.08 (2H, m), 2.28 (3H, s), 1.96-1.72 (4H, m) and 1.45 (3H, d).

MS: APCI (+ve): 422 (M+H)

EXAMPLE 42

[[3',5-difluoro-4'-(1-pyrrolidinylcarbonyl)[1,1'-biphenyl]-2-yl]oxy]-acetic acid

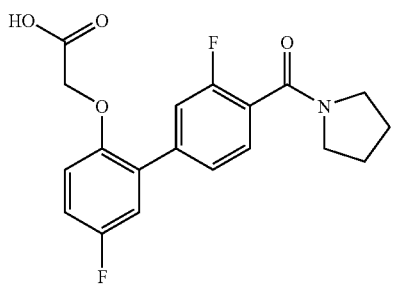

a) 3,5'-difluoro-2'-methoxy-[1,1'-biphenyl]-4-carboxylic acid 5-fluoro-2-methoxyboronic acid (1 g), 4-bromo-2-fluorobenzoic acid (1.29 g), tetrakis palladiumtriphenyphosphine (0) (0.6 g), toluene (40 ml), ethanol (16 ml) and 2M sodium carbonate (10 ml) were charged to a flask and heated at reflux overnight. The mixture was concentrated in vacuo then diluted with water and ethyl acetate. The aqueous layed was separated and acidified with 1N HCl, then extracted with ethyl acetate. The latter ethyl acetate layers were dried (MgSO$_4$) and concentrated in vacuo to give the sub-title compound as a beige solid. Yield 1.45 g.

$^1$H NMR CDCl$_3$: δ 8.08 (1H, t), 7.4 (2H, d), 7.11-7.04 (2H, m), 6.96-6.9 (1H, m), 3.81 (3H, s).

MS: ESI (-ve): 306 (M-H)

b) 1-[(3,5'-difluoro-2'-methoxy[1,1'-biphenyl]-4-yl) carbonyl]-pyrrolidine

The sub-title compound was prepared by the method of example 18 step a) using the product of step a) and pyrrolidine.

MS: ESI (+ve): 318 (M+H)

c) 1-[(3,5'-difluoro-2'-hydroxy[1,1'-biphenyl]-4-yl) carbonyl]-pyrrolidine

The sub-title compound was prepared by the method of example 18 step c) using the product of step b).

MS: ESI (-ve): 304 (M-H)

d) [[3',5-difluoro-4'-(1-pyrrolidinylcarbonyl)[1,1'-biphenyl]-2-yl]oxy]-acetic acid The title compound was prepared by the method of example 18 step d) using the product of step c).

MS: ESI (-ve): 362 (M-H)

$^1$H NMR DMSO-D6: δ 7.8-6.6 (6H, m), 4.49 (2H, s), 3.6-3.04 (4H, m) and 2-1.67 (4H, m).

EXAMPLE 43

(2S)-2-[3',5-difluoro-4'-(1-pyrrolidinylcarbonyl)[1,1'-biphenyl]-2-yl]oxy]-propanoic acid

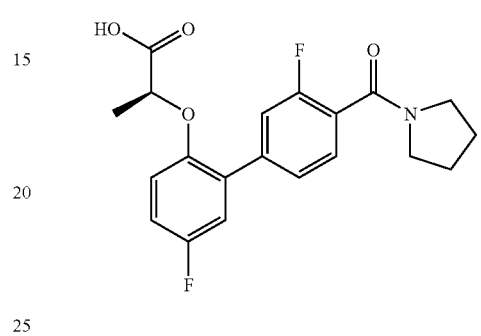

The title compound was prepared by the methods of example 1 step e) and example 38 step c) using the product of example 42 step c).

$^1$H NMR DMSO-D6: δ 7.76 (1H, d), 7.573 (1H, d), 7.39 (1H, t), 7.24 (1H, d), 7.17-7.01 (1H, m), 6.95-6.84 (1H, m), 4.67 (1H, m), 3.47 (2H, t), 3.4-3.1 (4H, m), 1.89-1.84 (2H, m) and 1.38 (3H, d).

MS: APCI (-ve): 374 (M-H)

EXAMPLE 44

(2S)-2-[[5-chloro-3'-fluoro-4'-[(2-methyl-1-pyrrolidinyl)carbonyl][1,1'-biphenyl]-2-yl]oxy]-propanoic acid

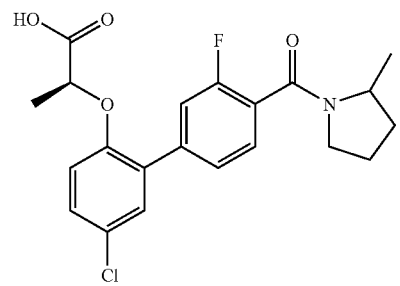

The title compound was prepared by the methods of example 32 step a) and example 32 step b) using the products of example 28 step c) and 2-methylpyrrolidine.

$^1$H NMR DMSO-D6: δ 7.74-7.65 (1H, m), 7.59-7.5 (1H, m), 7.42-7.31 (3H, m), 6.92 (1H, d), 4.7 (1H, q), 4.21-4.08 (1H, m), 3.6-3.5 (1H, m), 3.4-3.2 (1H, m), 2.1-1.7 (4H, m), 1.4 (3H, d), 1.23 (3H, d).

MS: APCI (-ve): 404 (M-H)

The compound was further purified by chiral HPLC to give:—

EXAMPLE 45

(2S)-2-[[5-chloro-3'-fluoro-4'-[[(2S)-2-methyl-1-pyrrolidinyl]carbonyl][1,1'-biphenyl]-2-yl]oxy]-propanoic acid MS: APCI (−ve): 404 (M−H)
and

EXAMPLE 46

(2S)-2-[[5-chloro-3'-fluoro-4'-[[(2R)-2-methyl-1-pyrrolidinyl]carbony][1,1'-biphenyl]-2-yl]oxy]-propanoic acid MS: APCI (−ve): 404 (M−H)

EXAMPLE 47

(2S)-2-[[4'-[(cyclopentylamino)carbonyl]-3'-fluoro-5-(trifluoromethyl)[1,1'-biphenyl]-2-yl]oxy]-propanoic acid

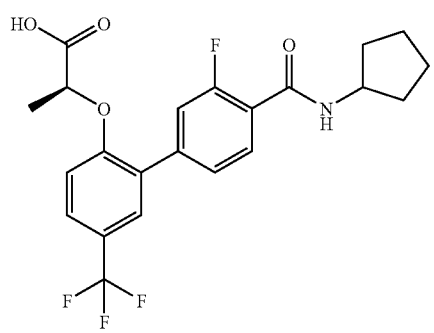

a) 4-bromo-N-cyclopentyl-2-fluoro-benzamide

The sub-title compound was prepared by the method of example 18 step a) using 4-bromo-2-fluorobenzoic acid and cyclopentanamine.
$^1$H NMR CDCl$_3$: δ 7.98 (1H, t), 7.4 (1H, d), 7.36-7.12 (1H, m), 6.65-6.43 (1H, m), 4.4 (1H, qd), 2.19-2 (2H, m), 1.8-1.43 (6H, m).

b) (2S)-2-[[4'-[(cyclopentylamino)carbonyl]-3'-fluoro-5-(trifluoromethyl)[1,1'-biphenyl]-2-yl]oxy]-propanoic acid The title compound was prepared using the product of step a) and (2S)-2-[2-borono-4-(trifluoromethyl)phenoxy]-propanoic acid [WO2004089885] by the method of example 32 step b).
$^1$H NMR DMSO-D6: δ 8.31 (1H, d), 7.78-7.43 (5H, m), 7.17 (1H, d), 5.03 (1H, q), 4.21 (1H, q), 1.9-1.8 (2H, m), 1.78-1.63 (2H, m) and 1.78-1.4 (7H, m).
MS: APCI (−ve): 438 (M−H)

EXAMPLE 48

(2S)-2-[[3'-fluoro-4'-[[(1-methylethyl)amino]carbonyl]-5-(trifluoromethyl)[1,1'-biphenyl]-2-yl]oxy]-propanoic acid

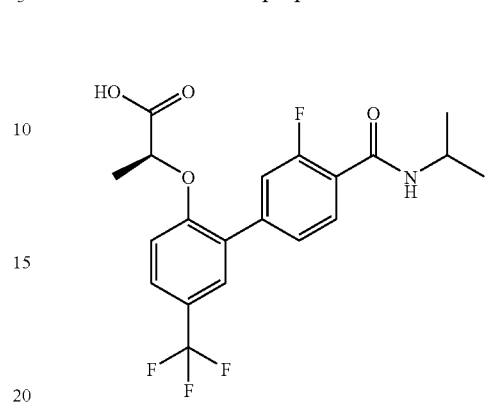

The title compound was prepared using the product of example 34 step a) and to (2S)-2-[2-borono-4-(trifluoromethyl)phenoxy]-propanoic acid [WO2004089885] by the method of example 32 step b).
$^1$H NMR DMSO-D6: δ 8.19 (1H, d), 7.73-7.54 (5H, m), 7.11 (1H, d), 4.83 (1H, q), 4.06 (1H, sept), 1.4 (3H, d), and 1.16 (6H, d).
MS: APCI (−ve): 412 (M−H)

EXAMPLE 49

(2S)-2-[[4'-[(ethylamino)carbonyl]-3'-fluoro-5-(trifluoromethyl)[1,1'-biphenyl]-2-yl]oxy]-propanoic acid

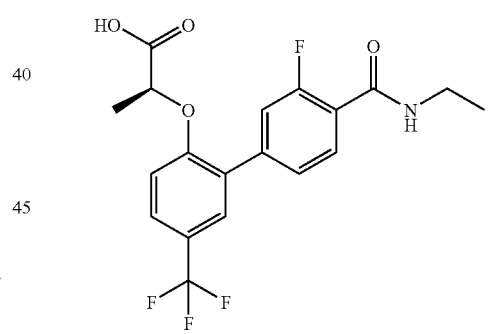

a) 4-bromo-N-ethyl-2-fluoro-benzamide

The sub-title compound was prepared by the method of example 18 step a) using 4-bromo-2-fluorobenzoic acid, ethylamine hydrochloride and triethylamine.
$^1$H NMR CDCl$_3$: δ 8.01 (1H, t), 7.41 (1H, d), 7.31 (1H, d), 6.62 (1H, s), 3.51 (2H, q) and 1.26 (3H, t).

b) (2S)-2-[[4'-[(ethylamino)carbonyl]-3'-fluoro-5-(trifluoromethyl)[1,1'-biphenyl]-2-yl]oxy]-propanoic acid The title compound was prepared using the product of step a) and (2S)-2-[2-borono-4-(trifluoromethyl)phenoxy]-propanoic acid [WO2004089885] by the method of example 32 step b).

¹H NMR DMSO-D6: δ 8.35 (1H, t), 7.73-7.5 (5H, m), 7.14 (1H, d), 5.03 (1H, m), 3.3 (2H, q), 1.43 (3H, d), and 1.1 (3H, t).

MS: APCI (+ve): 400 (M+H)

EXAMPLE 50

(2S)-2-[[5-chloro-4'-[[(1,1-dimethylethyl)amino]carbonyl]-3'-fluoro[1,1'-biphenyl]-2-yl]oxy]-propanoic acid

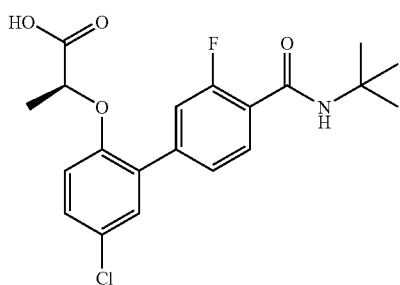

The title compound was prepared using the product of example 33 step a) and the product of example 28 step c) by the method of example 32 step b).

¹H NMR DMSO-D6: δ 7.89 (1H, s), 7.57-7.38 (5H, m), 6.99 (1H, d), 4.98 (1H, q), 1.43 (3H, d) and 1.39 (9H, s)

MS: APCI (-ve): 392 (M-H)

EXAMPLE 51

(2S)-2-[[5-chloro-4'-[(cyclopentylamino)carbonyl]-3'-fluoro[1,1'-biphenyl]-2-yl]oxy]-propanoic acid

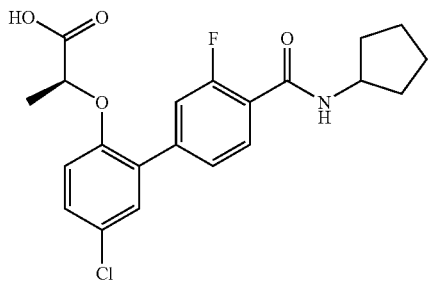

The title compound was prepared by the method of example 32 step b) using the products of example 28 step c) and example 47 step a).

¹H NMR DMSO-D6: δ 13.18 (1H, s), 8.32 (1H, d), 7.6-7.39 (5H, m), 7.01 (1H, d), 4.98 (1H, q), 4.24-4.19 (1H, m), 1.98-1.82 (2H, m), 1.81-1.59 (2H, m) and 1.78-1.41 (7H, m).

MS: APCI (-ve): 404 (M-H)

EXAMPLE 52

(2S)-2-[[5-chloro-4'-[(cyclopropylamino)carbonyl]-3'-fluoro[1,1'-biphenyl]-2-yl]oxy]-propanoic acid

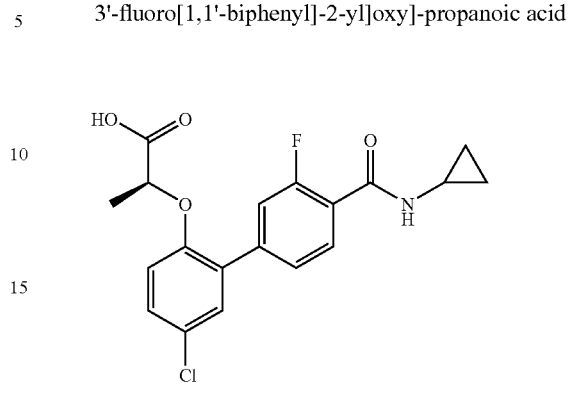

a) 4-bromo-N-cyclopropyl-2-fluoro-benzamide

The sub-title compound was prepared by the method of example 18 step a) using) 4-bromo-2-fluorobenzoic acid, and cyclopropylamine.

¹H NMR CDCl₃: δ 8.02 (1H, t), 7.42 (1H, d), 7.29 (1H, dd), 6.73-6.71 (1H, m), 2.96-2.94 (1H, m), 1.63-1.6 (2H, m) and 0.87-0.82 (2H, m).

b) (2S)-2-([5-chloro-4'-[(cyclopropylamino)carbonyl]-3'-fluoro[1,1-biphenyl]-2-yl]oxy]-propanoic acid The title compound was prepared by the method of example 32 step b) using the products of example 28 step c) and step a).

¹H NMR DMSO-D6: δ 8.40 (1H, d), 7.60-7.55 (2H, m), 7.50 (1H, dd), 7.42-7.38 (2H, m), 7.01 (1H, d), 4.98 (1H, q), 2.86 (1H, dsextet), 1.44 (3H, d), 0.73-0.68 (2H, m), 0.58-0.53 (2H, m).

MS: APCI (-ve): 376 (M-H)

EXAMPLE 53

(2S)-2-[[5-chloro-4'-[[(1-ethylpropyl)amino]carbonyl]-3'-fluoro[1,1'-biphenyl]-2-yl]oxy]-propanoic acid

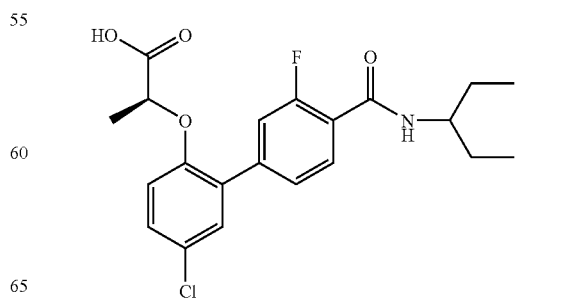

a) 4-bromo-N-(1-ethylpropyl)-2-fluoro-benzamide

The sub-title compound was prepared by the method of example 18 step a) using 4-bromo-2-fluorobenzoic acid and 3-pentanamine.

$^1$H NMR CDCl$_3$: δ 7.97 (1H, t), 7.42 (1H, dd), 7.31 (1H, dd), 6.4-6.33 (1H, m), 4.06-4.0 (1H, m), 1.7-1.62 (2H, m), 1.51-1.42 (2H, m) and 0.97 (6H, t).

b) 5'-chloro-N-(1-ethylpropyl)-3-fluoro-2'-methoxy-[1,1'-biphenyl]-4-carboxamide The sub-title compound was prepared by the method of example 18 step b) using the product of step a) and 4-chloro-2-methoxy boronic acid.

MS: ESI (+ve): 350 (M+H)

c) 5'-chloro-N-(1-ethylpropyl)-3-fluoro-2'-hydroxy-[1,1'-biphenyl]-4-carboxamide The sub-title compound was prepared by the method of example 18 step c) using the product of step b).

MS: ESI (−ve): 334 (M−H)

d) (2R)-2-(4-methylphenoxy)-propanoic acid, methyl ester

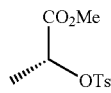

A solution of methyl (R)-(+)-lactate (6.66 g) in acetonitrile (33 ml) was cooled to 5° C. and triethylamine (9.8 ml) added followed by trimethylamine hydrochloride (0.62 g). A separate solution of p-toluenesulfonyl chloride (11.6 g) in acetonitrile (33 ml) was added dropwise over 20 mins maintaining the temperature below 5° C. The reaction mixture was filtered and concentrated. Diethyl ether and water were added and the organic fraction dried (MgSO$_4$) and concentrated in vacuo to give the sub-title compound as a yellow oil (13.71 g).

$^1$H NMR CDCl$_3$: δ 7.82 (2H, d), 7.35 (2H, d), 4.95 (1H, q), 3.67 (3H, s), 2.45 (3H, s), 1.51 (3H, d).

e) (2S)-2-[[5-chloro-4'-[[(1-ethylpropyl)amino]carbonyl]-3'-fluoro[1,1'-biphenyl]-2-yl]oxy]-propanoic acid The product of step c) (300 mg), the product of step d) (219 mg) and potassium carbonate (135 mg) in acetonitrile (10 ml) were charged to a flask and stirred at 50° C. for 16 h. The reaction mixture was cooled, diluted with water (20 ml) and extracted with diethyl ether (3×10 ml). The organic fractions were washed with brine, dried (MgSO$_4$) and concentrated in vacuo. The resulting yellow oil was dissolved in a 1:1 mixture of THF/methanol (10 ml) and 1M NaOH added (1.1 ml). The mixture was stirred at room temperature for 4 h and then concentrated in vacuo. The residue was purified by RPHPLC to give the title compound as a white solid (175 mg).

$^1$H NMR DMSO-D6: δ 8.02 (1H, d), 7.75 (1H, d), 7.59-7.48 (2H, m), 7.31 (2H, td), 6.93 (1H, d), 4.59 (1H, q), 3.75 (1H, quintet), 1.59-1.37 (4H, m), 1.34 (3H, d), 0.89 (6H, t).

MS: APCI (−ve): 406 (M−H)

EXAMPLE 54

(2S)-2-[[5-chloro-3'-fluoro-4'-[(methylamino)carbonyl][1,1'-biphenyl]-2-yl]oxy]-propanoic acid

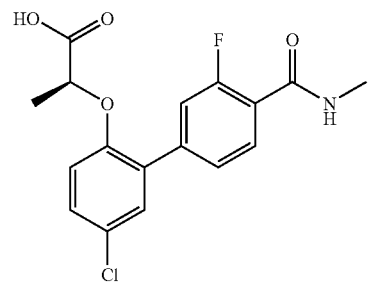

a) 4-bromo-2-fluoro-N-methyl-benzamide

The sub-title compound was prepared by the method of example 18 step a) using 4-bromo-2-fluorobenzoic acid and methylamine hydrochloride.

$^1$H NMR CDCl$_3$: δ 8.00 (1H, t), 7.42 (1H, dd), 7.32 (1H, dd), 6.66 (1H, s), 3.03 (3H, dd).

b) 5'-chloro-3-fluoro-2'-methoxy-N-methyl-[1,1'-biphenyl]-4-carboxamide

The sub-title compound was prepared by the method of example 18 step b) using the product of step a) and 4-chloro-2-methoxy boronic acid.

MS: ESI (+ve): 294 (M+H)

c) 5'-chloro-3-fluoro-2'-hydroxy-N-methyl-[1,1'-biphenyl]-4-carboxamide

The sub-title compound was prepared by the method of example 18 step c) using the product of step b).

MS: ESI (−ve): 278 (M−H)

d) (2S)-2-[[5-chloro-3'-fluoro-4'-[(methylamino)carbonyl][1,1'-biphenyl]-2-yl]oxy]-propanoic acid The title compound was prepared by the method of example 53 step e) using the product of step c). Purification by RPHPLC gave a white solid (170 mg).

$^1$H NMR DMSO-D6: δ 8.27 (1H, s), 7.85 (1H, d), 7.70-7.51 (2H, m), 7.34 (1H, d), 7.28 (1H, dd), 6.91 (1H, d), 4.50 (1H, q), 2.78 (3H, d), 1.33 (3H, d).

MS: APCI (−ve): 350 (M−H)

EXAMPLE 55

(2S)-2-[[5-chloro-4'-[[(1,1-dimethylethyl)amino]carbonyl]-3'-methyl[1,1'-biphenyl]-2-yl]oxy]-propanoic acid

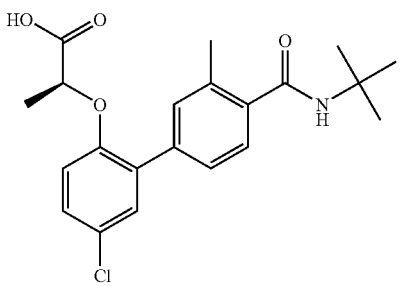

a) 4-bromo-N-(1,1-dimethylethyl)-2-methyl-benzamide

The sub-title compound was prepared by the method of example 18 step a) using 4-bromo-2-methylbenzoic acid and tertiarybutylamine.

$^1$H NMR CDCl$_3$: δ 7.36 (1H, d), 7.32 (1H, dd), 7.18 (1H, d), 5.50 (1H, s), 2.40 (3H, s), 1.46 (9H, s).

b) 5'-chloro-N-(1,1-dimethylethyl)-2'-methoxy-3-methyl-[1,1'-biphenyl]-4-carboxamide The sub-title compound was prepared by the methods of example 18 step b) using the product of step a) and 4-chloro-2-methoxy boronic acid.

MS: ESI (+ve): 332.0 (M+H)

c) 5'-chloro-N-(1,1-dimethylethyl)-2'-hydroxy-3-methyl-[1,1'-biphenyl]-4-carboxamide The sub-title compound was prepared by the method of example 18 step c) using the product of step b).

MS: ESI (−ve): 316.0 (M−H)

d) (2S)-2-[[5-chloro-4'-[[(1,1-dimethylethyl)amino]carbonyl]-3'-methyl][1,1'-biphenyl]-2-yl]oxy]-propanoic acid The title compound was prepared by the method of example 53 step e) using the product of step c). Purification by RPHPLC gave a white solid (230 mg).

$^1$H NMR DMSO-D6: δ 7.86 (1H, s), 7.56 (1H, d), 7.54 (1H, s), 7.25-7.19 (3H, m), 6.93-6.88 (1H, m), 4.39 (1H, m), 2.33 (3H, s), 1.36 (9H, s), 1.30 (3H, d).

MS: APCI (−ve): 388 (M−H)

EXAMPLE 56

[[5-chloro-4'-[[(1-ethylpropyl)amino]carbonyl]-3'-fluoro[1,1'-biphenyl]-2-yl]oxy]-acetic acid

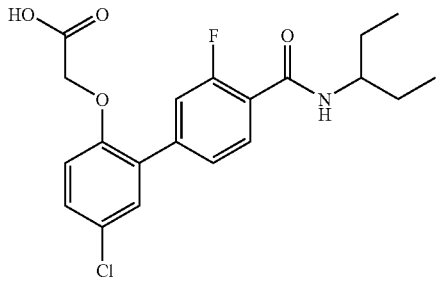

The title compound was prepared by the method of example 18 step d) using the product of example 53 step c). Purification by RPHPLC gave a white solid (81 mg).

$^1$H NMR DMSO-D6: δ 8.06 (1H, d), 7.66-7.48 (3H, m), 7.42-7.35 (2H, m), 7.04 (1H, d), 4.60 (2H, s), 3.85-3.69 (1H, m), 1.64-1.38 (4H, m), 0.91 (6H, t).

MS: APCI (−ve): 392 (M−H)

EXAMPLE 57

[[5-chloro-3'-fluoro-4'-[(methylamino)carbonyl][1,1'-biphenyl]-2-yl]oxy]-acetic acid

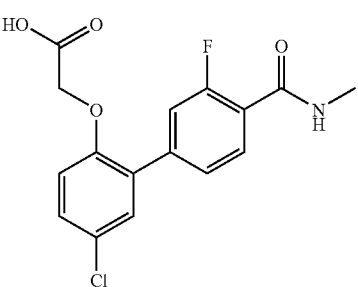

The title compound was prepared by the method of example 18 step d) using the product of example 54 step c). Purification by trituration from diethyl ether/isohexane gave a white solid (320 mg).

$^1$H NMR DMSO-D6: δ 13.11 (1H, s), 8.27 (1H, s), 7.65 (1H, t), 7.56 (1H, dd), 7.48 (1H, dd), 7.44-7.38 (2H, m), 7.09 (1H, d), 4.78 (2H, s), 3.79 (3H, d).

MS: APCI (−ve): 336 (M−H)

EXAMPLE 58

(2S)-2-[[5-chloro-4'-[(ethylamino)carbonyl]-3'-fluoro[1,1'-biphenyl]-2-yl]oxy]-propanoic acid

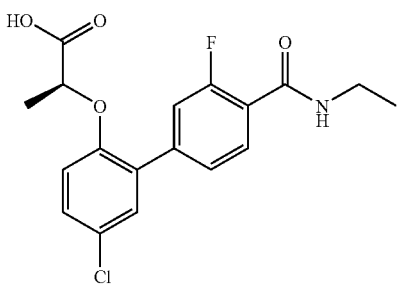

a) 5'-chloro-N-ethyl-3-fluoro-2'-methoxy-[1,1'-biphenyl]-4-carboxamide

The sub-title compound was prepared by the method of example 18 step a) using the product of example 21 step a) and ethylamine hydrochloride.
MS: ESI (+ve): 310 (M+H)

b) 5'-chloro-N-ethyl-3-fluoro-2'-hydroxy-[1,1'-biphenyl]-4-carboxamide

The sub-title compound was prepared by the method of example 18 step c) using the product of step a).
MS: ESI (−ve): 294 (M−H)

c) (2S)-2-[[5-chloro-4'-[(ethylamino)carbonyl]-3'-fluoro[1,1'-biphenyl]-2-yl]oxy]-propanoic acid The title compound was prepared by the methods of example 1 step e) and example 38 step c) using the product of step b). Purification by RPHPLC gave a white solid (28 mg).
$^1$H NMR CDCl$_3$: δ 7.93 (1H, t), 7.37 (1H, dd), 7.3 (1H, d), 7.23 (1H, d), 7.14 (1H, d), 6.79 (2H, m), 4.55 (1H, q), 3.48 (2H, m), 1.41 (3H, d) and 1.26 (3H, t).
MS: APCI (−ve): 364 (M−H)

EXAMPLE 59

(2S)-2-[[5-chloro-4'-[(cyclobutylamino)carbonyl]-3'-fluoro[1',1'-biphenyl]-2-yl]oxy]-propanoic acid

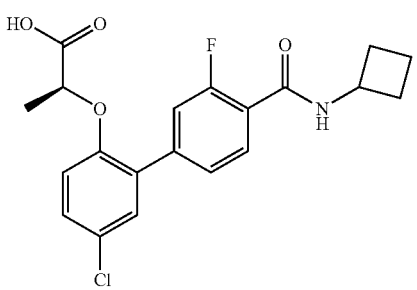

a) 5'-chloro-N-cyclobutyl-3-fluoro-2'-methoxy-[1,1'-biphenyl]-4-carboxamide

The sub-title compound was prepared by the method of example 18 step a) using the product of example 21 step a) and cyclobutanamine.
MS: ESI (+ve): 336 (M+H)

b) 5'-chloro-N-cyclobutyl-3-fluoro-2'-hydroxy-[1,1'-biphenyl]-4-carboxamide

The sub-title compound was prepared by the method of example 18 step c) using the product of step a).
MS: ESI (−ve): 320 (M−H)

c) (2S)-2-[[5-chloro-4'-[(ethylamino)carbonyl]-3'-fluoro[1,1'-biphenyl]-2-yl]oxy]-propanoic acid The title compound was prepared by the methods of example 1 step e) and example 38 step c) using the product of step b). Purification by RPHPLC gave a white solid (27 mg).
$^1$H NMR CDCl$_3$: δ 7.92 (1H, t), 7.35 (2H, m), 7.12 (1H, d), 6.99 (2H, m), 6.74 (1H, d), 4.95 (1H, m), 4.56 (1H, m), 2.4 (2H, s (broad)), 1.97 (2H, t), 1.77 (2H, s (broad) and 1.41 (3H, d).
MS: APCI (+ve): 392 (M+H)

EXAMPLE 60

(2S)-2-[[5-chloro-4'-[[(1,1-dimethylpropyl)amino]carbonyl]-3'-fluoro[1,1'-biphenyl]-2-yl]oxy]-propanoic acid

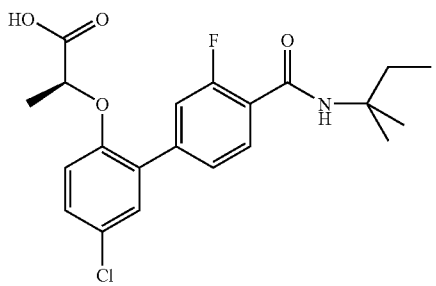

a) 5'-chloro-N-(1,1-dimethylpropyl)-3-fluoro-2'-methoxy-[1,1'-biphenyl]-4-carboxamide The sub-title compound was prepared by the method of example 18 step a) using the product of example 21 step a) and tert-amylamine.
MS: ESI (+ve): 352 (M+H)

b) 5'-chloro-N-(1,1-dimethylpropyl)-3-fluoro-2'-hydroxy-[1,1'-biphenyl]-4-carboxamide The sub-title compound was prepared by the method of example 18 step c) using the product of step a).
MS: ESI (−ve): 334 (M−H)

c) (2S)-2-[[5-chloro-4'-[(ethylamino)carbonyl]-3'-fluoro[1,1'-biphenyl]-2-yl]oxy]-propanoic acid The title compound was prepared by the method of example 53 step e) using the product of step b). Purification by RPHPLC gave a white solid (220 mg).

$^1$H NMR CDCl$_3$: δ 7.86 (1H, t), 7.35 (1H, d), 7.26 (1H, t), 7.18 (1H, d), 7.00 (1H, d), 6.66 (1H, d), 6.53 (1H, d), 4.41 (1H, d), 1.78 (2H, q), 1.38 (6H, s), 1.30 (3H, d), 0.89 (3H, t).
MS: APCI (−ve): 406 (M−H)

EXAMPLE 61

(2S)-2-[[5-chloro-3'-fluoro-4'-[[(3-methylbutyl)amino]carbonyl][1,1'-biphenyl]-2-yl]oxy]-propanoic acid

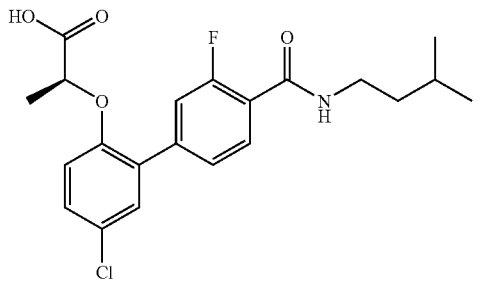

a) 5'-chloro-3-fluoro-2'-methoxy-N-(3-methylbutyl)-[1,1'-biphenyl]-4-carboxamide The sub-title compound was prepared by the method of example 18 step a) using the product of example 21 step a) and isoamylamine.
MS: ESI (+ve): 352 (M+H)

b) 5'-chloro-3-fluoro-2'-hydroxy-N-(3-methylbutyl)-[1,1'-biphenyl]-4-carboxamide The sub-title compound was prepared by the method of example 18 step c) using the product of step a).
MS: ESI (−ve): 334 (M−H)

c) (2S)-2-[[5-chloro-3'-fluoro-4'-[[(3-methylbutyl)amino]carbonyl][1,1'-biphenyl]-2-yl]oxy]-propanoic acid The title compound was prepared by the method of example 53 step e) using the product of step b).
$^1$H NMR CDCl$_3$: δ 7.75 (1H, t), 7.32 (1H, d), 7.23 (1H, d), 7.10 (1H, s), 6.90 (1H, d), 6.83 (1H, t), 6.61 (1H, d), 4.28 (1H, d), 3.37 (2H, d), 1.62 (1H, t), 1.44 (2H, d), 1.17 (3H, d), 0.90 (6H, d).
MS: APCI (−ve): 406 (M−H)

Pharmacological Data
Ligand Binding Assay

[$^3$H]PGD$_2$ was purchased from Perkin Elmer Life Sciences with a specific activity of 100-210 Ci/mmol. All other chemicals were of analytical grade.

HEK cells expressing rhCRTh2/Gα16 were routinely maintained in DMEM containing 10% Foetal Bovine Serum (HyClone), 1 mg/ml geneticin, 2 mM L-glutamine and 1% non-essential amino acids. For the preparation of membranes, the adherent transfected HEK cells were grown to confluence in two layer tissue culture factories (Fisher, catalogue number TKT-170-070E). Maximal levels of receptor expression were induced by addition of 500 mM sodium butyrate for the last 18 hours of culture. The adherent cells were washed once with phosphate buffered saline (PBS, 50 ml per cell factory) and detached by the addition of 50 ml per cell factory of ice-cold membrane homogenisation buffer [20 mM HEPES (pH 7.4), 0.1 mM dithiothreitol, 1 mM EDTA, 0.1 mM phenyl methyl sulphonyl fluoride and 100 μg/ml bacitracin]. Cells were pelleted by centrifugation at 220×g for 10 minutes at 4° C., re-suspended in half the original volume of fresh membrane homogenisation buffer and disrupted using a Polytron homogeniser for 2×20 second bursts keeping the tube in ice at all times. Unbroken cells were removed by centrifugation at 220×g for 10 minutes at 4° C. and the membrane fraction pelleted by centrifugation at 90000×g for 30 minutes at 4° C. The final pellet was re-suspended in 4 ml of membrane homogenisation buffer per cell factory used and the protein content determined. Membranes were stored at −80° C. in suitable aliquots.

All assays were performed in Corning clear bottomed, white 96-well NBS plates (Fisher). Prior to assay, the HEK cells membranes containing CRTh2 were coated onto SPA PVT WGA beads (Amersham). For coating membranes were incubated with beads at typically 25 μg membrane protein per mg beads at 4° C. with constant agitation overnight. (The optimum coating concentrations were determined for each batch of membranes) The beads were pelleted by centrifugation (800×g for 7 minutes at 4° C.), washed once with assay buffer (50 mM HEPES pH 7.4 containing 5 mM magnesium chloride) and finally re-suspended in assay buffer at a bead concentration of 10 mg/ml.

Each assay contained 20 μl of 6.25 nM [$^3$H]PGD$_2$, 20 μl membrane saturated SPA beads both in assay buffer and 100 of compound solution or 13,14-dihydro-15-keto prostaglandin D$_2$ (DK-PGD$_2$, for determination of non-specific binding, Cayman chemical company).

Compounds and DK-PGD$_2$ were dissolved in DMSO and diluted in the same solvent to 100× the required final concentration. Assay buffer was added to give a final concentration of 10% DMSO (compounds were now at 10× the required final concentration) and this was the solution added to the assay plate. The assay plate was incubated at room temperature for 2 hours and counted on a Wallac Microbeta liquid scintillation counter (1 minute per well).

Compounds of formula (I) have an IC$_{50}$ value of less than (<) 10 μM.

Specifically example 5 has a pIC$_{50}$ value of 8.75, example 11 has a pIC$_{50}$ value of 7.45 and example 13 has a pIC$_{50}$ of 8.15.

Shape Change Assay

DK-PGD$_2$ [13,14-dihydro-15-keto Prostaglandin D$_2$] was obtained from Cayman Chemical (Michigan, USA). Optilyse B was from Immunotech (Marseille, France). All other chemical reagents were of analytical grade from Fisher Scientific (Loughborough, UK) or Sigma (Poole, UK).

Human blood was taken by venipuncture from healthy volunteers into Monovette is tubes (Sarstedt) containing heparin as anticoagulant. The assays were carried out in deep 96-well polypropylene plate. The blood (90 μL) is incubated with tested compounds (10 μL) during 4 min at 37° C. Cells were fixed by the addition of 100 μl of optilyse B (Immunotech) followed by incubation at room temperature for 10 min. Next, red blood cells were lysed by the addition of 1 mL of water and further incubation at room temperature for 45 mM. The plate was centrifuged for 5 min at 375×g, the supernatant was discarded and cells were resuspended in 400 μL of assay buffer (Dulbecco's PBS without Ca$^{2+}$ and Mg$^{2+}$ supplemented with 10 mM HEPES, 10 mM glucose and 0.1% BSA; pH 7.4). The fixed cells were transferred to tubes suitable for use with the flow cytometer.

Shape change was determined using a Coulter FC500 flow cytometer, by measuring the ability of these cells to scatter light when illuminated. By gating the granulocyte region on the basis of their FS/SS profile, FL-2 was plotted against FL-1 identifying two populations of cells: neutrophils with low auto-fluorescence and eosinophils that showed higher natural autofluorescence. The eosinophil population is gated and changes in the median value in FS are recorded.

Compounds were tested at final concentrations of 1 and 10 μM. These were dissolved in DMSO to give a 10 mM solution. Further dilutions were performed in 96-well polypropylene plates in assay buffer to give a 100 μM solution containing 1% DMSO. An additional 1 in 10 dilution was made in assay buffer containing 1% DMSO. Both these solutions were diluted 1 in 10 into the assay mixture to give a final DMSO concentration of 0.1% (v/v). Concentration response curves for DK-PGD$_2$ were constructed as a control in each experiment. The efficacy of tested compounds was expressed as a fraction of the maximum response to PGD$_2$.

These compounds were considered antagonists when their efficacy ratio was lower than 0.25.

The invention claimed is:

1. A compound of formula (I) or a pharmaceutically acceptable salt thereof:

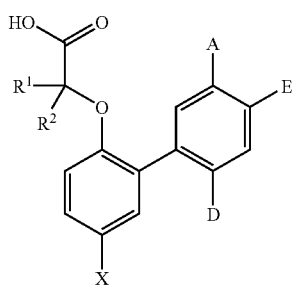

in which:
X is $C_{1-2}$ alkyl which is substituted by one or more halogen atoms;
A is independently selected from halogen, $SO_2NR^3R^4$, $SO_nR^5$ (n=1 or 2), $CONR^3R^4$, or $C_{1-3}$ alkyl which can be optionally substituted by one or more halogen atoms;
E is $CONR^3R^4$ where $R^3$ and $R^4$ together form a pyrrolidine, piperidine, azetidine or isoxazoline ring, each optionally substituted by halogen or $C_1$-$C_3$ alkyl;
D is hydrogen or fluorine;
$R^1$ and $R^2$ independently represent a hydrogen atom, or a $C_{1-3}$alkyl group; or
$R^1$ and $R^2$ together can form a 3-8 membered ring optionally containing one or more atoms selected from O, S, $NR^6$ and itself optionally substituted by one or more $C_1$-$C_3$ alkyl;
$R^3$ and $R^4$ independently represent hydrogen, $C_3$-$C_7$ cycloalkyl or $C_{1-6}$alkyl, the latter two groups being optionally substituted by one or more substituents independently selected from halogen, $C_3$-$C_7$ cycloalkyl, $OR^6$ and $NR^7R^8$; or $R^3$ and $R^4$ together with the nitrogen atom to which they are attached can form a 3-8 membered saturated heterocylic ring optionally containing one or more atoms selected from O, $S(O)_n$ (where n=0, 1 or 2), $NR^8$, and itself optionally substituted by halogen or $C_{1-3}$ alkyl;
$R^5$ is $C_1$-$C_6$ alkyl or $C_{3-7}$ cycloalkyl, which may be optionally substituted by halogen atoms;
$R^6$ is hydrogen or $C_1$-$C_6$ alkyl;
$R^7$ and $R^8$ independently represent hydrogen, $C_1$-$C_6$ alkyl or $C_{3-7}$ cycloalkyl or
$R^7$ and $R^8$ together with the nitrogen atom to which they are attached can form a 3-8 membered saturated heterocyclic ring as defined above for $R^3$ and $R^4$.

2. A compound according to claim 1 in which X is trifluoromethyl.

3. A compound according to claim 1 above in which A independently represents trifluoromethyl, $C_{1-3}$alkyl, halogen, $SOR^5$, $SO_2R^5$, $CONR^3R^4$ or $SO_2NR^3R^4$.

4. A compound according to claim 1 in which D is hydrogen.

5. A compound according to claim 1 in which $R^1$ and $R^2$ are both hydrogen.

6. A compound according to claim 1 in which one of $R^1$ and $R^2$ is hydrogen and the other is methyl.

7. A compound according to claim 1 selected from:
[[3'-methyl-4'-(1-piperidinylcarbonyl)-5-(trifluoromethyl)[1,1'-biphenyl]-2-yl]oxy]-acetic acid;
[[3'-methyl-4'-(1-pyrrolidinylcarbonyl 1)-5-(trifluoromethyl)[1,1'-biphenyl]-2-yl]oxy]-acetic acid;
(2S)-2-[[3'-fluoro-4'-(1-pyrrolidinylcarbonyl)-5-(trifluoromethyl)[1,1'-biphenyl]-2-yl]oxy]-propanoic acid;
[[3'-fluoro-4'-(1-pyrrolidinylcarbonyl)-5-(trifluoromethyl)[1,1'-biphenyl]-2-yl]oxy]-acetic acid; and
(2S)-2-[[3'-methyl-4'-(1-pyrrolidinylcarbonyl)-5-(trifluoromethyl)[1,1'-biphenyl]-2-yl]oxy]-propanoic acid;
and pharmaceutically acceptable salts thereof.

8. A method of treating a respiratory disease, selected from a group consisting of asthma and rhinitis, in a patient suffering from, or at risk of, said disease, which comprises administering to the patient a therapeutically effective amount of a compound of formula (I), or a pharmaceutically acceptable salt or solvate thereof, as defined in claim 1.

9. A compound of formula (II):

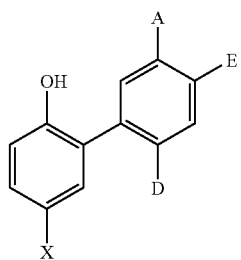

in which X, A, D and E are as defined in formula (I) in claim 1.

* * * * *